United States Patent
Ahmad

(10) Patent No.: US 11,769,580 B1
(45) Date of Patent: *Sep. 26, 2023

(54) HEALTH MONITORING AND COACHING SYSTEM

(71) Applicant: Invoy Holdings Inc., Irvine, CA (US)

(72) Inventor: Lubna M. Ahmad, Chandler, AZ (US)

(73) Assignee: Invoy Holdings Inc., Irvine, CA (US)

(*) Notice: Subject to any disclaimer, the term of this patent is extended or adjusted under 35 U.S.C. 154(b) by 64 days.

This patent is subject to a terminal disclaimer.

(21) Appl. No.: 17/343,516

(22) Filed: Jun. 9, 2021

Related U.S. Application Data

(63) Continuation of application No. 16/551,260, filed on Aug. 26, 2019, now Pat. No. 11,056,223, which is a continuation-in-part of application No. 16/232,975, filed on Dec. 26, 2018, now Pat. No. 11,250,942.

(60) Provisional application No. 62/659,668, filed on Apr. 18, 2018, provisional application No. 62/610,903, filed on Dec. 27, 2017.

(51) Int. Cl.
| | |
|---|---|
| *G16H 20/60* | (2018.01) |
| *G16H 20/30* | (2018.01) |
| *G06F 9/54* | (2006.01) |
| *A61B 5/08* | (2006.01) |
| *A61B 5/00* | (2006.01) |
| *G16H 10/20* | (2018.01) |

(52) U.S. Cl.
CPC .......... *G16H 20/60* (2018.01); *A61B 5/0022* (2013.01); *A61B 5/082* (2013.01); *G06F 9/542* (2013.01); *G16H 10/20* (2018.01); *G16H 20/30* (2018.01)

(58) Field of Classification Search
CPC ................. A61B 5/082; A61B 5/4866; A61B 2010/0087; A61B 5/0022; G16H 20/60; G16H 20/30; G16H 10/20; G06F 9/542
See application file for complete search history.

(56) References Cited

U.S. PATENT DOCUMENTS

| | | | | |
|---|---|---|---|---|
| 8,722,417 | B2* | 5/2014 | Ahmad | A61B 5/082 |
| | | | | 422/89 |
| 9,341,632 | B1 | 5/2016 | Ahmad et al. | |
| 9,486,169 | B1 | 11/2016 | Ahmad | |
| 9,643,186 | B1* | 5/2017 | Ahmad | G01N 33/542 |
| 10,068,494 | B2 | 9/2018 | Ahmad et al. | |
| 10,226,201 | B2 | 3/2019 | Ahmad et al. | |

(Continued)

*Primary Examiner* — Malina D. Blaise
(74) *Attorney, Agent, or Firm* — Knobbe, Martens, Olson & Bear, LLP

(57) ABSTRACT

A system is disclosed that monitors participants in health-related programs, such as weight loss or exercise programs, and that provides automated, personalized health coaching to the program participants. The system includes breath analysis devices that are used by the program participants to generate ketone measurements, and includes a mobile application that runs on mobile devices of the participants and communicates with corresponding breath analysis devices. The system operates generally by monitoring ketone levels (such as acetone levels) and other attributes of the participants and by making personalized, machine-generated changes or updates to such programs to maintain program effectiveness and engagement. In some embodiments the system uses primary and secondary process flows to collect from the participants information that is used to select or recommend health program modifications.

13 Claims, 39 Drawing Sheets

(56) References Cited

U.S. PATENT DOCUMENTS

| | | | |
|---|---|---|---|
| 10,285,642 B2* | 5/2019 | Ahmad | A61B 5/7405 |
| 2006/0241722 A1 | 10/2006 | Thacker et al. | |
| 2008/0161661 A1 | 7/2008 | Gizewski | |
| 2009/0311654 A1 | 12/2009 | Lopez | |
| 2011/0003665 A1 | 1/2011 | Burton et al. | |
| 2013/0102018 A1* | 4/2013 | Schentag | G01N 21/05 |
| | | | 435/25 |
| 2013/0150746 A1 | 6/2013 | Tao et al. | |
| 2014/0170735 A1* | 6/2014 | Holmes | G01N 21/76 |
| | | | 435/287.1 |
| 2014/0234949 A1* | 8/2014 | Wasson | B01L 3/50851 |
| | | | 422/519 |
| 2014/0276100 A1* | 9/2014 | Satterfield | A61B 5/7271 |
| | | | 600/476 |
| 2014/0288680 A1 | 9/2014 | Hoffman et al. | |
| 2014/0296089 A1* | 10/2014 | Holmes | G01N 35/0092 |
| | | | 435/7.1 |
| 2015/0132858 A1* | 5/2015 | Ahmad | A61B 5/097 |
| | | | 436/130 |
| 2015/0302156 A1 | 10/2015 | Parsadoust | |
| 2015/0310508 A1 | 10/2015 | Pattekar et al. | |
| 2015/0335267 A1* | 11/2015 | Cormier | A61B 5/0836 |
| | | | 600/532 |
| 2015/0339363 A1 | 11/2015 | Moldoveanu et al. | |
| 2016/0089038 A1 | 3/2016 | Chadderdon, III et al. | |
| 2016/0242674 A1 | 8/2016 | Ahmad et al. | |
| 2016/0245797 A1 | 8/2016 | Ahmad et al. | |
| 2016/0262657 A1* | 9/2016 | Ahmad | A61B 5/7271 |
| 2016/0270724 A1* | 9/2016 | Ahmad | A61B 5/082 |
| 2017/0039336 A1* | 2/2017 | Bitran | G16H 20/70 |
| 2017/0300628 A1 | 10/2017 | Laing et al. | |
| 2018/0108272 A1 | 4/2018 | Ahmad et al. | |
| 2018/0130076 A1 | 5/2018 | Celik et al. | |
| 2018/0190382 A1 | 7/2018 | Ramezani et al. | |
| 2019/0160460 A1* | 5/2019 | Keatch | H10N 30/2042 |

* cited by examiner

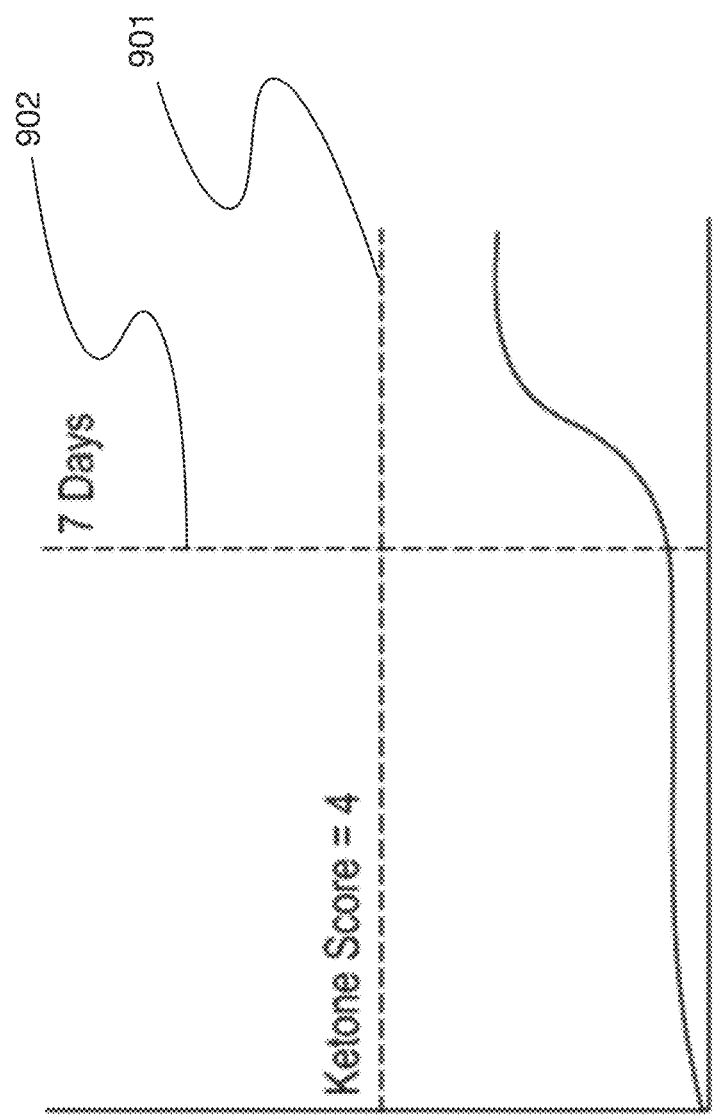

FIG. 10

Profile

Goal weight
170lbs — 1301

Height
1302 — 5' 4"

Artificial sweeteners
Yes — 1303

Alcohol
1304 — Yes

Email address
jpaul@gmail.com — 1305

Home | My week | My journey | Chat | Profile

HEALTH MONITORING AND COACHING SYSTEM

PRIORITY CLAIM

This application is a continuation U.S. application Ser. No. 16/551,260, filed Aug. 26, 2019, which is a continuation-in-part of U.S. application Ser. No. 16/232,975, filed Dec. 26, 2018, which claims the benefit of U.S. Provisional Application Nos. 62/610,903, filed Dec. 27, 2017, and 62/659,668, filed Apr. 18, 2018. The disclosures of the aforesaid applications are hereby incorporated by reference.

FIELD

The present disclosure relates to machine-based processes, including machine learning processes and human-machine interfaces, for automatically coaching participants in a weight loss or other health related program based on various factors, preferably including monitored ketone levels, of the participants. This coaching is preferably, but optionally, predictive. Although ketone levels are advantageous for several reasons described herein, other metabolic analytes may be used.

BACKGROUND

Obesity is a major individual and public health concern in the United States and throughout the world. In the United States alone, approximately 33% of the adult population is obese and another 33% are overweight. Treatment of obesity and other weight-related disorders involves a multi-factorial approach (typically a combination of diet, exercise, behavioral health modifications and sometimes medication or surgery) and commonly requires significant and sometimes permanent lifestyle modification. Especially in adults, the oft-required lifestyle changes can make obesity an extremely difficult condition to overcome.

The main goal of obesity management is reducing the amount of fat in the body. For various reasons (to motivate subjects, to enforce compliance and to troubleshoot/customize diets), it is useful and important to have a means to track and trend fat metabolism.

As an example, individuals suffering from other metabolic conditions, such as elevated cholesterol or high blood pressure, may benefit from improving their diet or changing exercise patterns. A growing number of individuals seek to reduce their carbohydrate intake to increase utilization of fat as an energy source, in hopes of reducing their overall insulin usage and thereby counteracting metabolic abnormalities (such as high blood pressure).

Athletes and fitness-conscious individuals are concerned about staying in peak physical condition, and are often actively engaged in structured sports activities (whether professional or not). Such individuals struggle with making data-driven decisions about how best to optimize their biochemical and physical condition. They often try to make "smart" decisions about how best to reach their fitness or health goals.

However, tracking and trending fat metabolism is useful beyond weight management and the treatment of obesity. Anorexia nervosa is a psychiatric disorder having substantial implications and is oftentimes a lifelong illness. The disorder is most prevalent in adolescents and young adults, and is 90% more common in young women than men. Because of the complex nature of the disorder and the significant level of mental health treatment, treatment of anorexia nervosa is most effective in-center and is correspondingly expensive. Improving patient outcomes requires considerable counseling and monitoring.

SUMMARY

A system is disclosed that uses profiles of users, including monitored ketone levels of the users, to assess effectiveness levels of health programs (such as weight loss programs) assigned to the users, and to select health program modifications for the users. The system may use a machine learning (artificial intelligence) algorithm to adaptively learn how to classify users and to select messaging and behavioral modifications for the users. For example, in some embodiments the system classifies the users and provides associated health program recommendations using a computer model trained with expert-classified user data records. As another example, a set of rules may be used to generate the health program recommendations and related messaging, and the set of rules may automatically be modified over time based on feedback data reflective of health program effectiveness levels produced by such rules. In some embodiments the system includes a mobile application that runs on mobile devices of users and communicates wirelessly with breath analysis devices of the users. The mobile application may also communicate with a server-based system that generates the health program recommendations.

In some embodiments, the mobile application presents two different types of screen flows or user interface flows to the user. The first type of UI flow is preferably presented each time the user takes a ketone measurement. This first flow seeks information from the user regarding conditions and behaviors that may have affected the measurement. The second type of UI flow is presented less frequently, such as on a weekly basis and/or when the user finishes use of a multi-day (e.g., 7-day) disposable. This second type of flow collects information from the user that is not specific to any particular measurement (e.g., information regarding the user's satisfaction with the current program, preferences, goals, travel plans, etc.). The system uses the information collected from the two types of flows to generate recommendations for the next multi-day cycle (e.g., one week), or to otherwise assist the user in planning for that cycle. The combined use of these two different types of UI flows enables the system to efficiently collect information from the user while minimizing the burden placed on the user.

BRIEF DESCRIPTION OF THE DRAWINGS

FIGS. 9A-9D illustrate examples of how ketone levels (scores) of users can be used to select health programs for the user.

FIG. 10 illustrates an example screen display of one embodiment of a mobile application's test initiation page.

FIG. 13 illustrates an example screen display of the "profile" page of the mobile application of FIG. 8.

DETAILED DESCRIPTION OF SPECIFIC EMBODIMENTS

Figure 1:
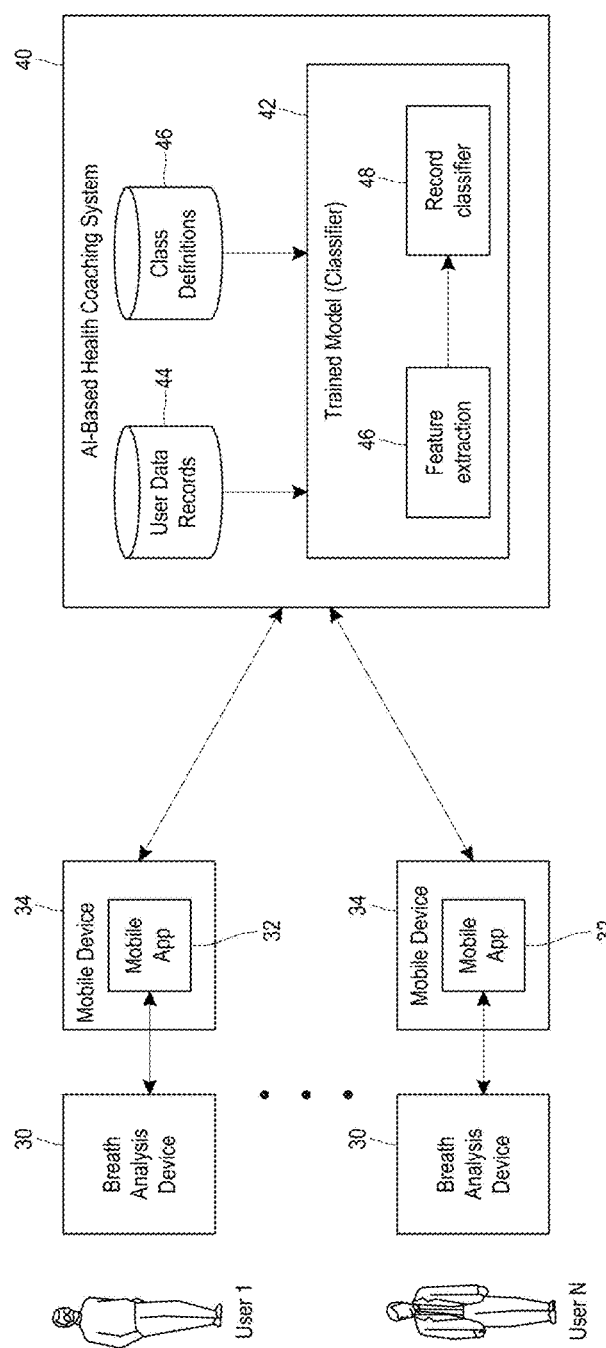
FIG. 1 illustrates an AI-based health coaching system according to one embodiment.

Given the availability of portable analysis devices (including breath analysis devices) with wireless capabilities, it is desirable to have a system that can provide automated, personalized feedback or coaching, such as weight loss coaching, to individual users based on their monitored ketone levels and other factors. FIG. 1 illustrates one embodiment of such a system. This system operates generally by monitoring ketone levels and other attributes of participants in health-related programs, and by making personalized, machine-generated changes or updates to such programs to improve program effectiveness. The programs may include or consist of diets or food plans, and/or exercise programs intended to achieve weight loss or other health benefits. For purposes of illustration, the system will be described primarily in the context of weight loss programs, and the program participants will be referred to primarily as "users" of the system or as "clients." The terms "recommendations," "program recommendations" and "coaching" will be used to refer generally to the auto-selected programs, program updates, behavioral modifications, and associated messaging, provided by the system to or for users.

As illustrated in FIG. 1, each user of the system uses a portable breath analysis device 30 to generate ketone measurements from breath samples as described above and in the aforementioned patent references. Each such device 30 includes a ketone sensor capable of generating ketone measurements from breath samples of a corresponding user, and includes a wireless transceiver that is used to report the ketone measurements. The ketone sensor may be a semiconductor sensor, such as a nanoparticle-based sensor, or may be a colorimetric sensor. Some examples of suitable breath analysis devices are disclosed in U.S. Provisional Appl. No. 62/773,045, filed Nov. 29, 2018, the disclosure of which is hereby incorporated by reference. The measured ketones may include, for example, acetone, acetoacetate, and/or B-hydroxybutyric acid. In some embodiments the ketone measurements may instead be generated from other types of bodily fluid samples of the users, such as blood or urine samples. In some embodiments, such as the embodiment shown in FIGS. 32A-32C and 33 (described below), the breath analysis device may use a multi-day, multi-test disposable cartridge, such as the 7-day cartridge shown in FIG. 33.

As the ketone measurements are generated, they are communicated over a communications network, which may include the Internet, to a remote, Artificial Intelligence (AI) based health coaching system 40. In the illustrated embodiment, each breath analysis device 30 communicates wirelessly with a mobile application ("mobile app") installed on a smartphone, tablet, or other mobile communications device ("mobile device") 34 of the respective user. The mobile application 32 may implement a variety of features (such as the features described in U.S. Pat. No. 9,341,632, which is hereby incorporated by reference herein) for assisting users in generating, monitoring and tagging ketone measurements, and for processing such measurements. In some embodiments, the breath analysis devices 30 may alternatively communicate directly with the health coaching system 40, such as via a WIFI connection; in these embodiments, the mobile application 32 and mobile device 34, may be omitted.

Portable breath analysis devices have recently become available that enable users to monitor their ketone levels. Examples of such devices are disclosed in U.S. Pat. No. 9,341,632 and U.S. Patent Appl. Nos. 62/338,312, filed May 18, 2016, Ser. No. 15/077,642, filed Mar. 22, 2016, 62/396,240, filed on Sep. 19, 2016, and 62/368,311, filed Jul. 29, 2016, the disclosures of which are hereby incorporated by reference. In some cases, the portable breath analysis device uses a wireless (e.g., Bluetooth, WIFI, Zigbee) transceiver and connection to report the measurements to a mobile application that runs on the user's smartphone, tablet, or other mobile or personal device. The mobile application may in turn report the measurements to a remote system. In some cases, the breath analysis device may alternatively report the measurements to the remote system directly, in which case the mobile application may be omitted.

System Summary

In this example, the System provides a user with personalized, data-driven feedback that evolves as the user evolves. In this example, the system utilizes a model comprised of: a user goal, a food plan, and an accelerant. The user provides certain user-input information and also provides a bodily fluid sample from which to analyze a ketone level (via the breath analysis device 30). This information is displayed to the user as a Program Score (described later herein) and a subset of this information is available to the user's social community and/or coach. The community or coach view is triaged to represent at-risk, failing and compliant users.

Mobile Application

In one embodiment of the mobile application 32, the application is comprised of five key screens, each of which may display personalized data transmitted by the health coaching system 40 to the mobile device 34. Specifically, these are: Home, My Week, My Journey, Chat and Profile. These screens guide the user through their daily testing, and also provide a comprehensive summary of the user's short term and long term progress.

Figure 4:
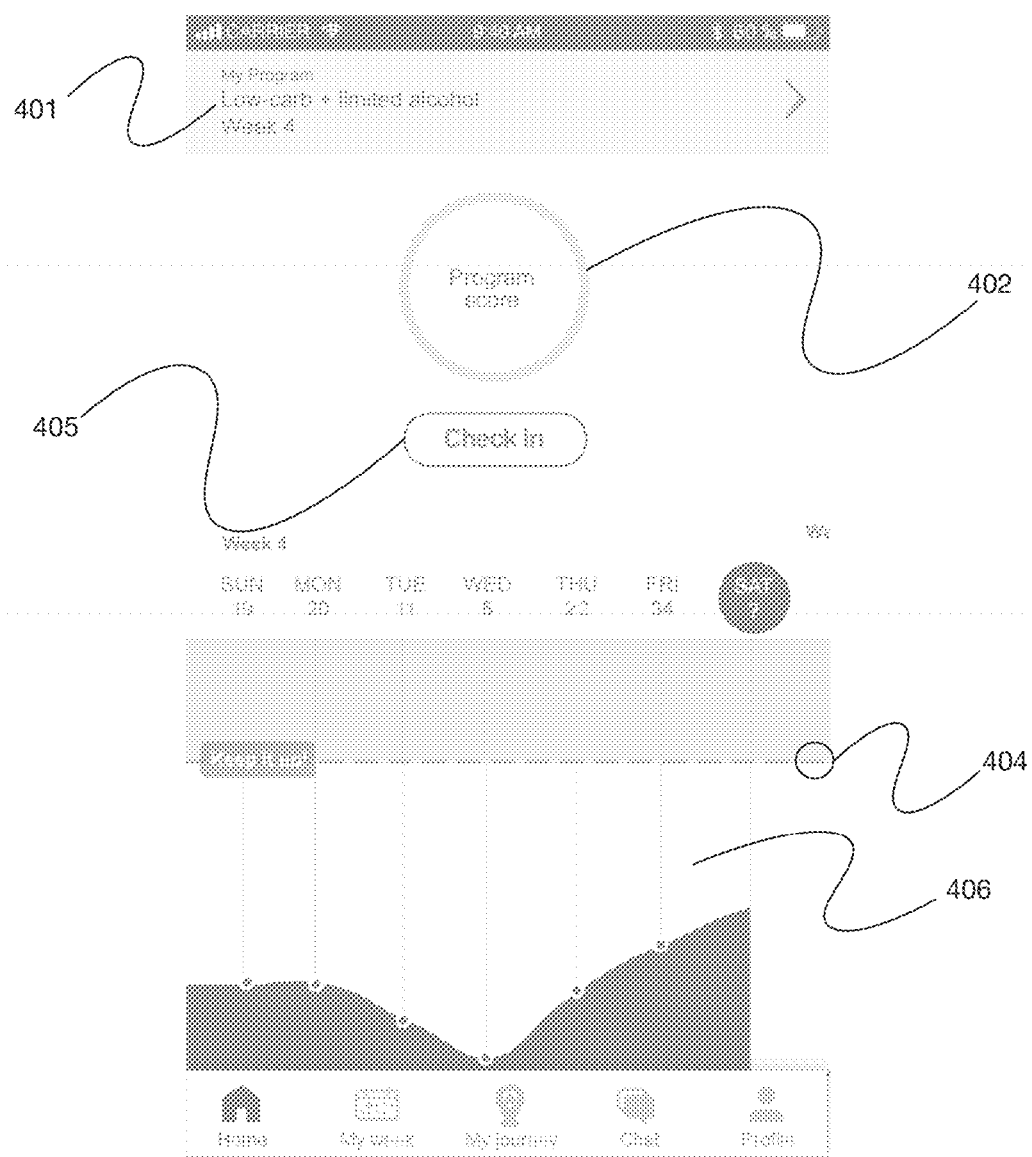
FIG. 4 illustrates an example screen display of one embodiment of a mobile application's home page.
Figure 5:
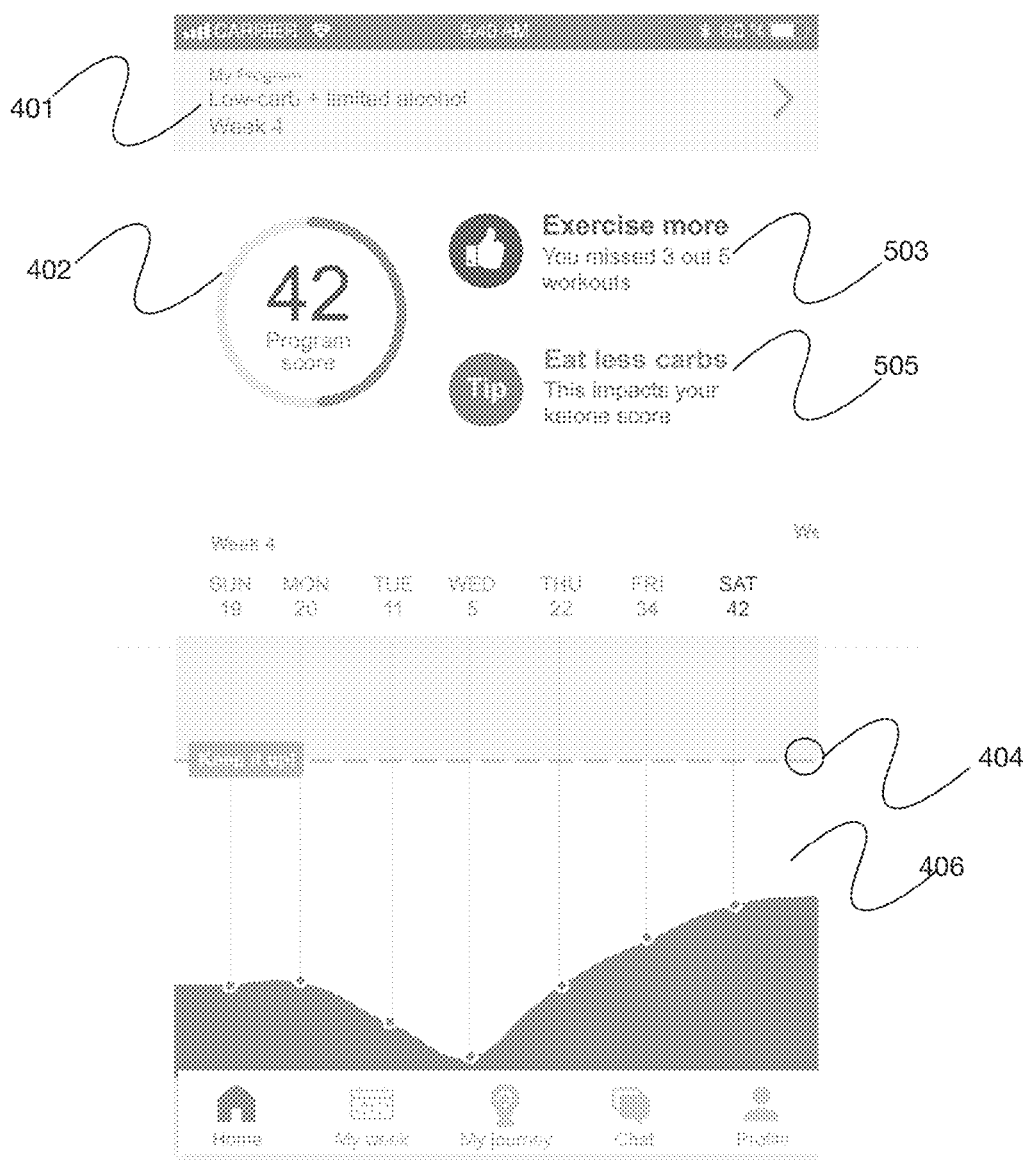
FIG. 5 illustrates an example screen display of the home page of the mobile application of FIG. 4.

After onboarding (described elsewhere herein), the user is directed to the Home screen, illustrated in FIG. 4. This screen may also be referred to as the "main" screen, the "dashboard" screen, etc. Within this screen, the "My Program" indication near the top 401 reminds the user of the individual program he or she is on, with a "Week X" indication of how long they have been on the program. The user is to click on the "Check In" button 405 which will direct the user to a modal just as the one shown on FIG. 10, referred to as the Daily Log. Once the user completes the information on the Daily Log, the Program Score 402 will transform from a blank space shown in FIG. 4 to the populated space shown on FIG. 5. The Home Page also includes a weekly summary 406 near the bottom of the display, that indicates the user's test scores for the last seven (7) days (scrollable for 30 days, in this example). The weekly summary also includes a threshold marker 404, which indicates the target program score for the user. The threshold marker may be stagnant and the same for all users, it may be tailored based on the user's program, or it may be individualized based on the user's goals and/or historical data. The marker aids the user in reviewing his or her data to determine program efficacy. The threshold marker may also be set by the system based on "similar" users—for example, the user profile may include certain characteristics that the user considers key: e.g., working Mom, executive, major life stress, etc. The threshold marker may be relative to others with a similar set of characteristics.

There are several processes that may be used by the system to identify similar users. One way to identify similar users is to prompt the users to fill out a questionnaire with specific questions about their lifestyle, hours at work, hobbies, and other personal information. Another way is to pull profile information from a user's social media and professional networking sites. While these processes provide strong signals on how to categorize users, they may also require significant amount of effort for users or appear invasive. Additionally, they suffer from a shortcoming in that they represent a categorization that is from a snapshot in time and can thus be susceptible to false positives because the user was not truthful or mindful about their answers. An alternative approach would be sending users periodic text messages, emails, or mobile push notifications that ask simple yes or no questions. For example, "are you at work right now?". From a user interface perspective these types of messages can be implemented in a manner that requires minimal effort from the user. For example, the system could send a text message asking the user to reply with "1" or "2". To make the process and UI even more efficient the system could send simple URLs and hyperlinks that the user simply needs to click on instead of typing. To further make the process and UI more efficient, the system could send a push notification so that the user can respond without having to unlock their mobile device. Regardless of how the questions are communicated to the users, the system may periodically execute a matching or clustering algorithm that groups together similar users based on the user responses (and/or other provide data). The output of this algorithm is a data table or other data structure that maps users to similar users.

Figure 10:
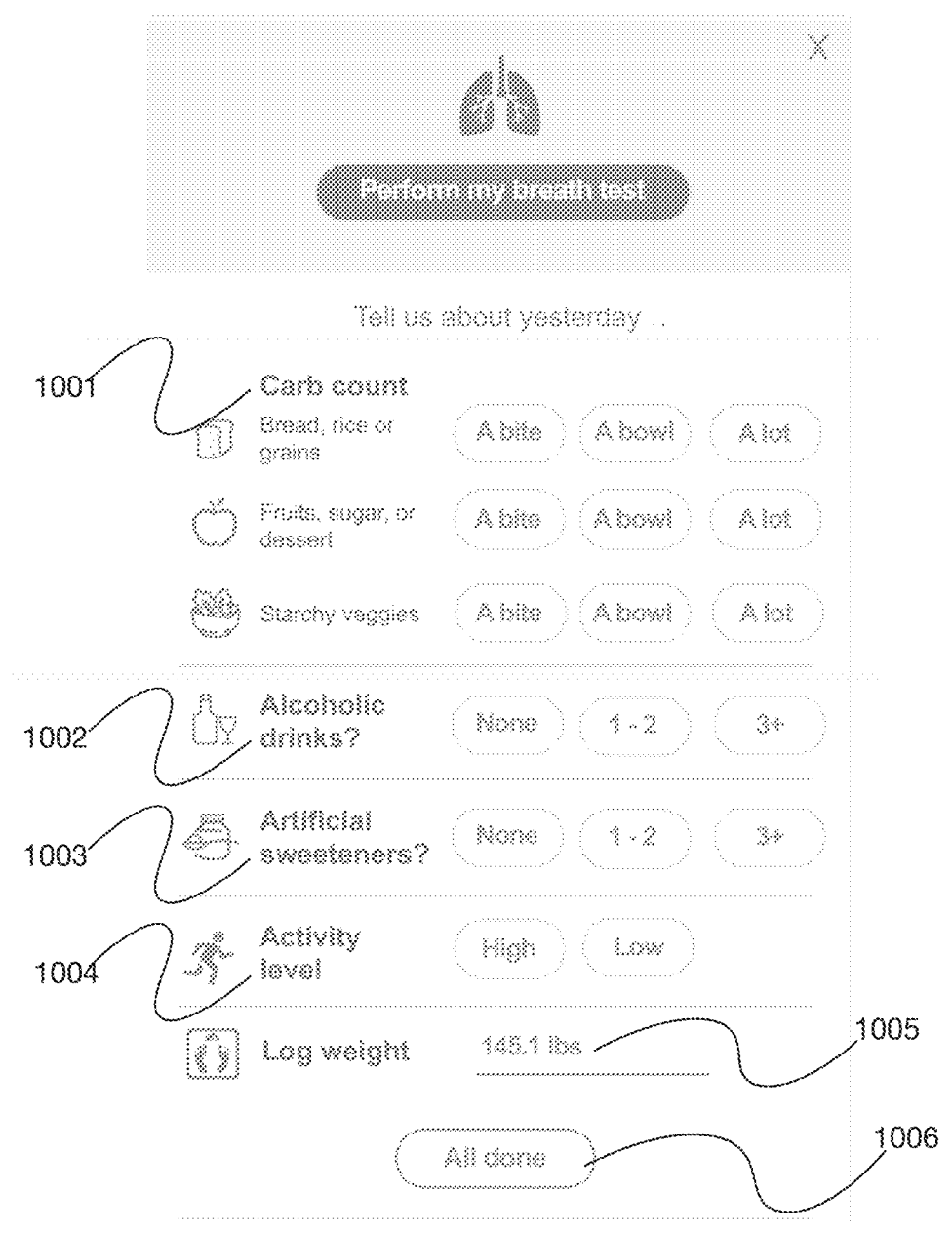

FIG. 10 illustrates an example Daily Log screen of one embodiment of the mobile application 32. The Daily Log contains a listing of the pieces of information solicited from the user. The user then responds to certain queries that are generated by the System. Here, they are: basic information about carbohydrate consumption 1001, alcoholic drinks 1002, artificial sweeteners 1003, activity level 1004, and weight 1005.

Referring back to FIG. 5, after the user has completed the Daily Log, the Program Score is displayed. Additionally, the view displays a certain number of tips, that are designed to be actionable by the user, e.g., exercise more 503 or eat less carbs 505. These tips are generated from the data provided by the user from the Daily Log or his or her ketone scores. A chart displays historical program scores (in this case, 7 days on the page and 30 days worth of data if the user scrolls from the side to side).

Figure 6:
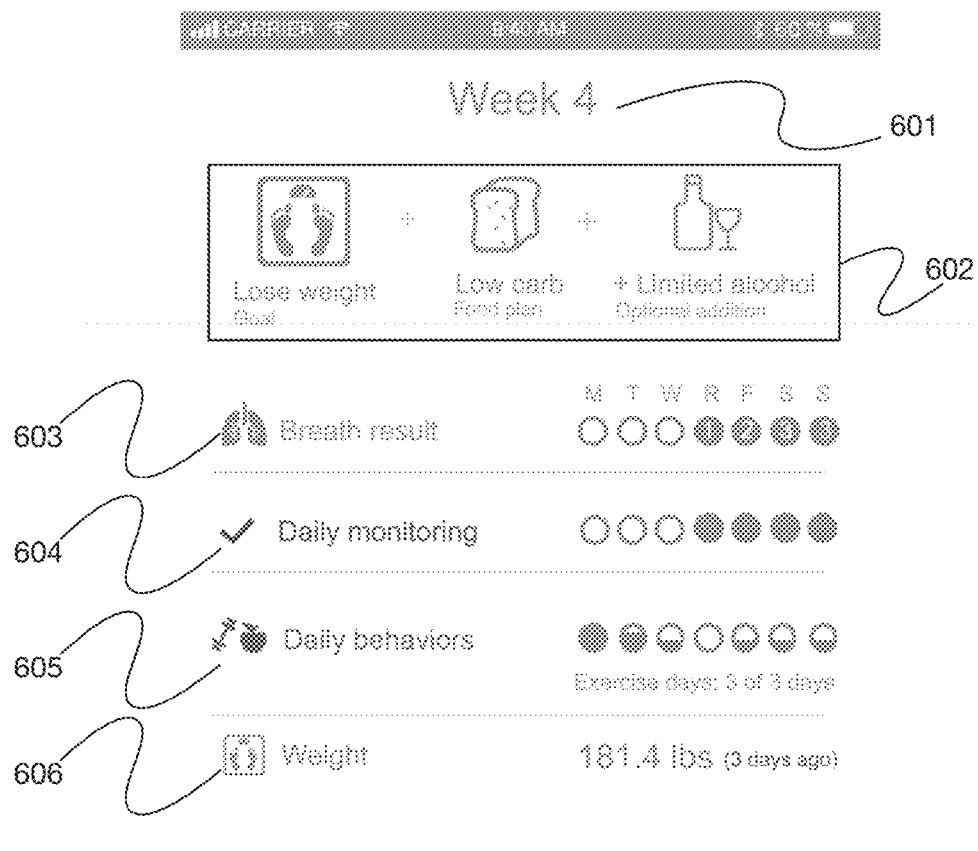
FIG. 6 illustrates an example screen display of one embodiment of a mobile application's "my week" page.

FIG. 6 illustrates an example My Week screen for one embodiment of the mobile application 32. The view includes an indication of the week of the program 601, to inform the user of the stage of the program they are in. The view also includes a program overview 602, to indicate the user's current program. The view also includes a summary of the week's Breath Results 603, Daily Monitoring (whether a test was performed or not) 604, Daily Behaviors (e.g., habit adherence) 605, and the user's most recently recorded weight 606. In this case, if the user performed a breath test, one of the circles under Daily Monitoring is completed. For each time a test is performed, the highest score achieved by the user within a designated time window is annotated in the corresponding Breath Result circle. Here, the user performed a test on Friday and the score was 2 ppm, thus the circle for Friday under Daily Monitoring is shaded and the number "2" appears in the shaded circle of Breath Result. The Daily Behaviors section shows the percentage of the habits that the user successfully adhered to based on the Daily Log (e.g., did you exercise, did you avoid alcohol?)—note that habits are described later herein.

Figure 7:
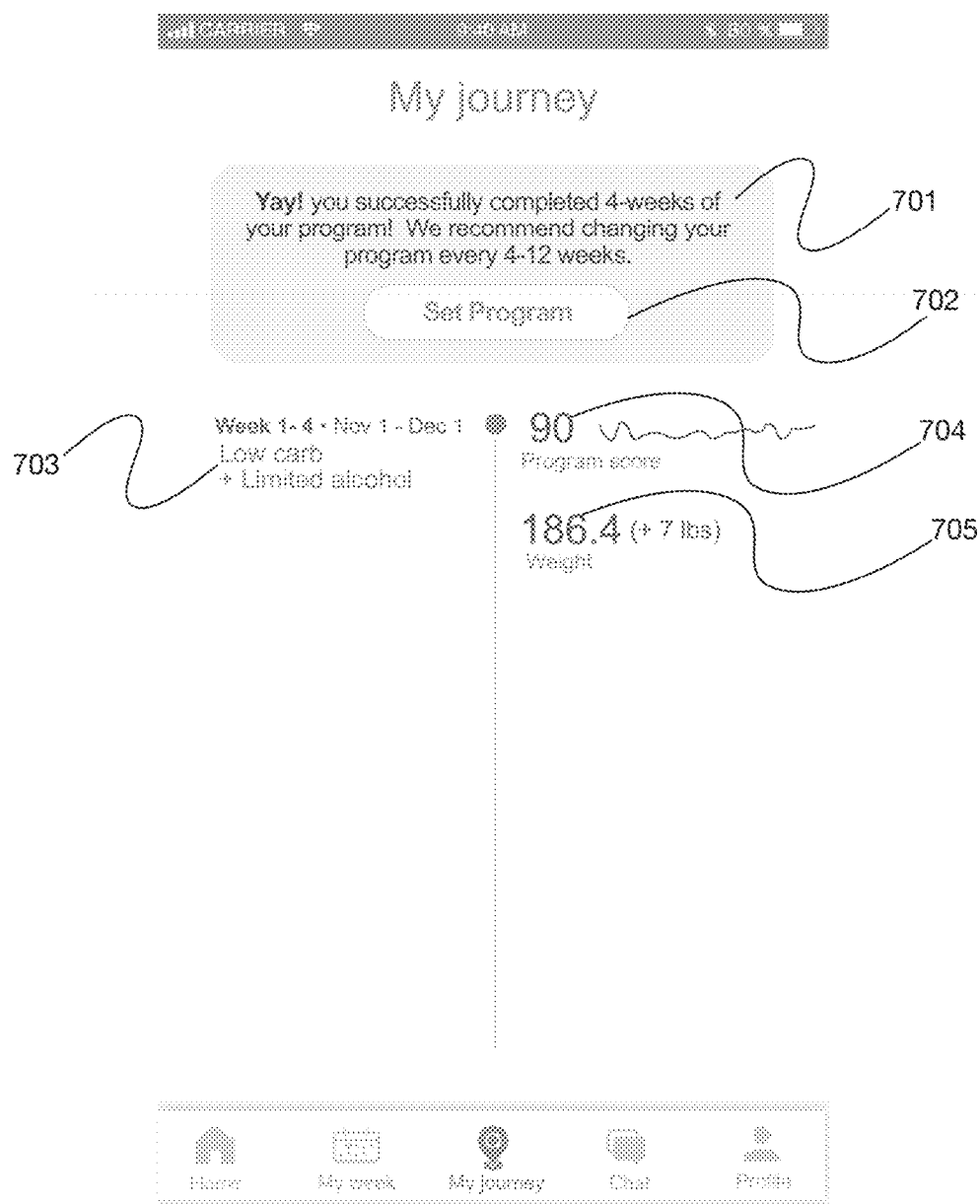
FIG. 7 illustrates an example screen display of one embodiment of a mobile application's "my journey" page.

FIG. 7 illustrates an example My Journey screen of one embodiment of the mobile application 32, which provides a summary of a user's progress on the program thus far. For each block of time (here, November 1 to December 1) that a user is on a specific program (here, Low carb+ Limited Alcohol), the user's progress is shown. For each program, the average Program Score 704 and the last recorded weight 705 is displayed. The view will populate, over time, as the user's program changes. For the example, the Week 1 to Week 4 summary may be followed by a Week 5 to Week 12 summary, a Week 13 to Week 16 summary, etc. The user may use this screen to review their program progress in terms of phases, to help determine if any long-term progress or goals have been attained. This view is also useful to see if one program is more or less effective than the others. After the user has been on a designated program for 4 weeks, the banner 701 is shown. If the user is interested in changing his or her program, the user may click on Set Program 702. This feature is designed to encourage the user to make changes before his or her body adapts or before he/she gets bored.

Figure 8:
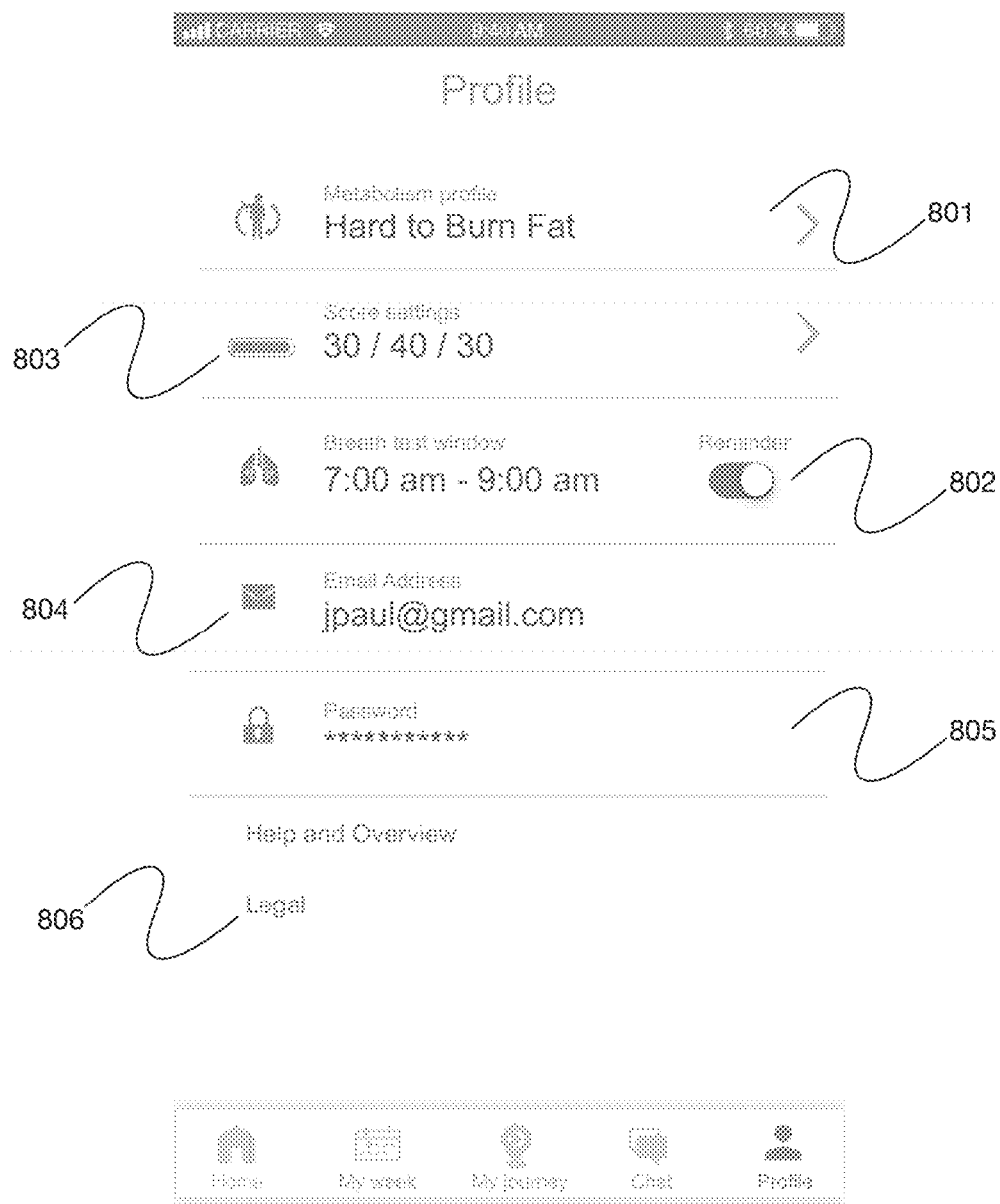
FIG. 8 illustrates an example screen display of one embodiment of a mobile application's "profile" page.

FIG. 8 illustrates an example Profile screen of one embodiment of the mobile application 32. This profile section provides general information about the user. This view includes the user's metabolism profile 801, which is algorithmically determined from a user's baseline data, here computed over a 7 to 14-day basis. The Profile also includes a score settings 803, which is the weight attributed to each of the program elements that comprise the computation of the Program Score. The score settings may be determined based on the metabolism profile, based on the user's goals or set by the user. The view also includes an indication of the user's breath test window 802. The breath test window may be used to assist in the determination of adherence to rules, as described in U.S. application Ser. No. 14/807,813, filed Jul. 23, 2105, entitled: "Ketone Measurement System Capable of Validating Measurements Against Behavioral Rules", which is incorporated herein by reference in its entirety. In alternate embodiments, the user's profile page may look like FIG. 13 where certain characteristics about the user's preferences is solicited, here whether the user consumes artificial sweeteners or alcohol. If the user does not have alcohol, there is no need for the App to prompt the user for a diet change to exclude alcohol, for example.

Without the user's metabolism profile, the UI of the system presented to the user would likely become far more cumbersome, less efficient, and less accurate. The metabolism profile operates as a statistical cache in much the same way as RAM operates as a cache for data normally stored on a hard disk in a computer system. By having a metabolism profile pre-computed, the system needs to request fewer pieces of information to understand the state of the user, and the system is able to make recommendations with fewer readings. Since a user usually only performs a limited number of readings a day, the ability to make recommendations with fewer readings greatly improves the efficiency of the system overall. Algorithmically, the information contained in the metabolism profile is preferably serialized as a textual descriptor that is used as a key to look up rules in a look up table. Examples of how the metabolism profile is serialized include XML, JSON, CSV, and other data exchange formats. The metabolism may also be stored in an application-specific binary representation. Using the key to look up rules in a lookup table may be achieved through implementing the lookup table as a hash map in which the table is searched for a record with a key that exactly matches the metabolism profile's textual representation. Alternatively, the rule lookup table may be structured as a table with many columns, and the metabolism profile may be represented as a vector of values. To look up the key in the table in one embodiment, the dot product is performed between the key and the table columns, and the row with the highest dot product is used. This allows the metabolism profile to encode multi-dimensional data which enables the system to respond to nuanced changes in data and thus give higher accuracy recommendations. If a rule does not exist, a default rule may be used, or the system may resort to collecting more data to characterize the user.

Figure 16:
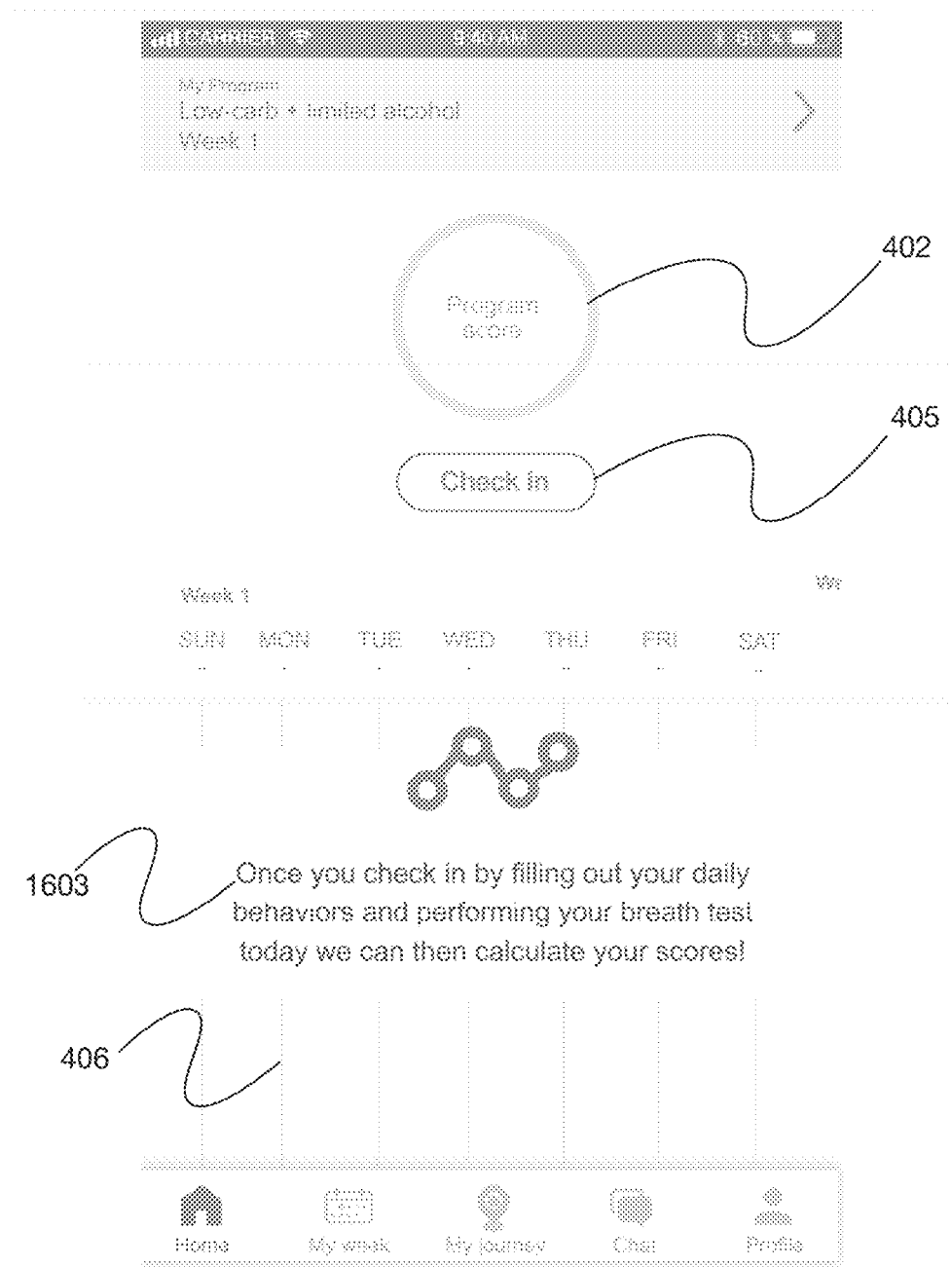
FIG. 16 illustrates an example screen display of the home page of the mobile application of FIG. 4.
Figure 17:
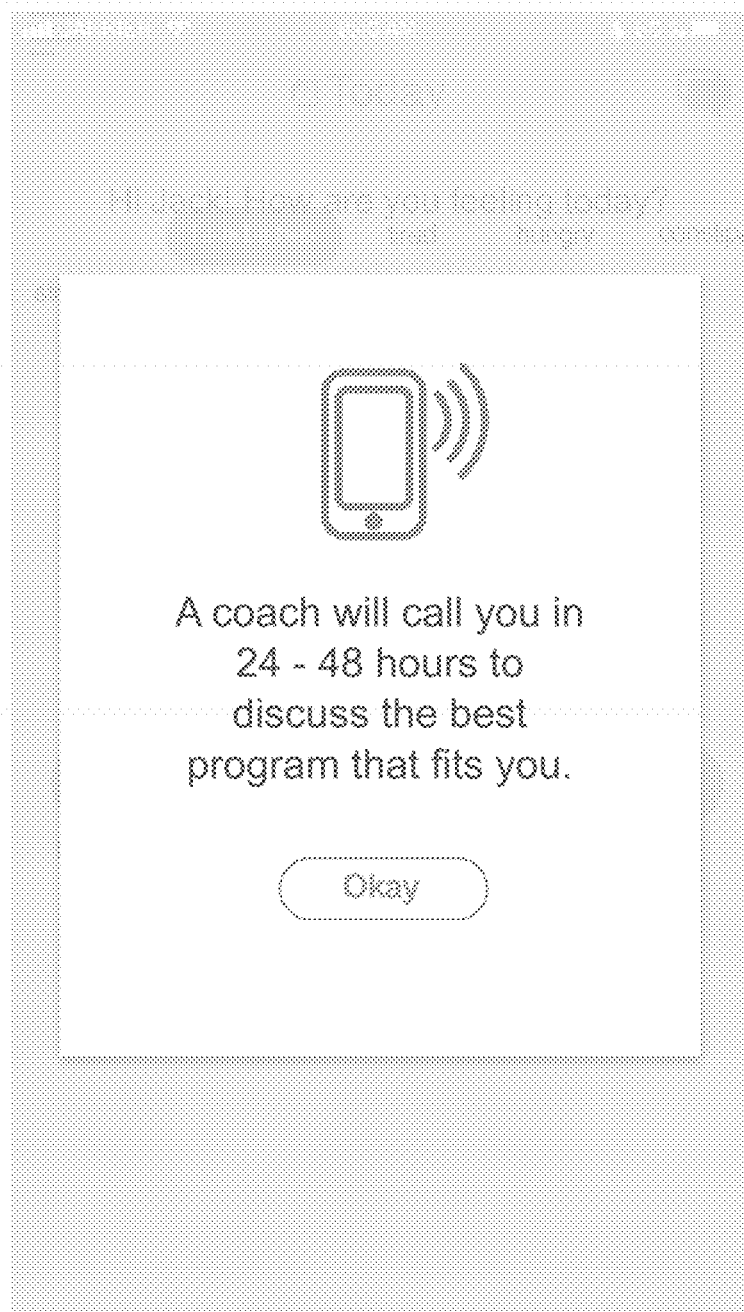
FIG. 17 illustrates an example screen display of one embodiment of a mobile application's "coaching" feature.

Some background on onboarding is useful. When the user initially begins a program, he or she is directed to a screen like FIG. 16. The user completes a certain amount of baseline data to (a) display the Program Score (it is preferably weighted over a plurality of days) or (b) determine his or her metabolism profile.

The metabolism profile 801 is any profile that depicts a classification of a user based on his or her physiology. In this example, the profile is computed over 14 days. The user begins the baseline from "scratch" or ideally after 2 days consuming some level of carbohydrates. The user is then instructed to follow a rigid low carbohydrate food plan of <20 g total carbs per day. The user's ketone levels are monitored each morning and the baseline data may be charted as a function of ketone score over time. The data is then categorized based on achieving a threshold level 901, here 4 ppm, within a threshold time 902, here 7 days. Certain profiles are shown in FIGS. 9A-9D. This example utilizes four different metabolism profiles, however any number of profiles that are deemed significant may be utilized. Additionally, other types of profiles may be used, for example the results of glucose tolerance test or other profiling techniques described in U.S. application 62/528,200, entitled: "Automated Processes for Detecting and Addressing Health Issues Based on Monitored Analytes and Other User Data."

User Goal

The user goal may be any goal that the system recognizes and coaches a user to follow. The user may input the user goal. But it is possible that the system prompts the user to change his or her goal in view of historical patterns, e.g., with the user's data, in view of upcoming holidays/vacations, or because of changes made by others in the user's social community.

Examples of user goals are: losing weight, maintaining weight, improving athletic performance, building muscle, increasing energy, improving sleep, improving attention (cognitive function), staying healthy while pregnant, and others. For medical purposes, user goals may be: improving glycemic control, reducing medication, reducing cholesterol, mitigating depression, managing cancer, and others.

The user goal may change for several reasons. As an example, a user may input a user goal of "lose weight" (here, 50 pounds). She loses 20 pounds over 3 months and then is about to enter into a 2-month stage at work where she knows she will be very busy. For those two months, she changes her goal to "maintain weight". After that period of work is completed, she returns to her previous user goal of "lose weight."

Another example is that a user has a goal of "lose weight". The system determines that the user is going on vacation to Europe for 3 weeks based on, for example, a calendar entry or change in location. The system prompts the user: "Do you want to change your goal from lose weight to maintain weight?"

Another example is that a user has a goal of "lose weight". The system determines that 75% of the user's friends changed their goals to "build muscle mass". The system prompts the user: "Several of your friends have changed their goals recently. Are you interested in changing your goal?"

Another example is that a user has a goal of "maintain weight". The user is very compliant with daily use statistics of >90%. But the user is a female with a height of 5'S" and a weight of 160 pounds. The system prompts the user: "You have been doing great! Just curious, have you thought about changing your goal? We think you'd be very successful on another program!"

Another example is that a user has a goal of "lose weight." The user has been compliant (daily monitoring and daily log shows that user is generally compliant) but is receiving low ketone scores. The system has access to sleep data from a sleep monitor, e.g., through Beddit, HealthKit, Fitbit or others. The system notices that the user's sleep has become highly irregular over the past 3 weeks. The system prompts the user: "Would you like to switch your goal to "Improve Sleep"? Ultimately, getting better sleep may help you lose weight too!"

In some embodiments of the system, the user may desire more than one goal. For example, the user may have a goal to lose weight, and have another goal of increasing athletic performance. In another example, a user may want to lose weight, but also increase energy. The system provides feedback to the user in the same fashion, and in some instances, may ask the user to switch to just one goal, if the system determines that the feedback given for different goals conflict each other. The system may also determine if any combination of goals is deemed illogical, or oppose each other from a health perspective. For example, a user may have a goal of losing weight, and have another goal of building muscle. The system recognizes that in some individuals, the addition of muscle to a user's body may result in weight gain. This prompts the system to suggest that the user first achieve a goal of losing weight, and then switch their program to achieve a goal of building muscle.

Figure 11:
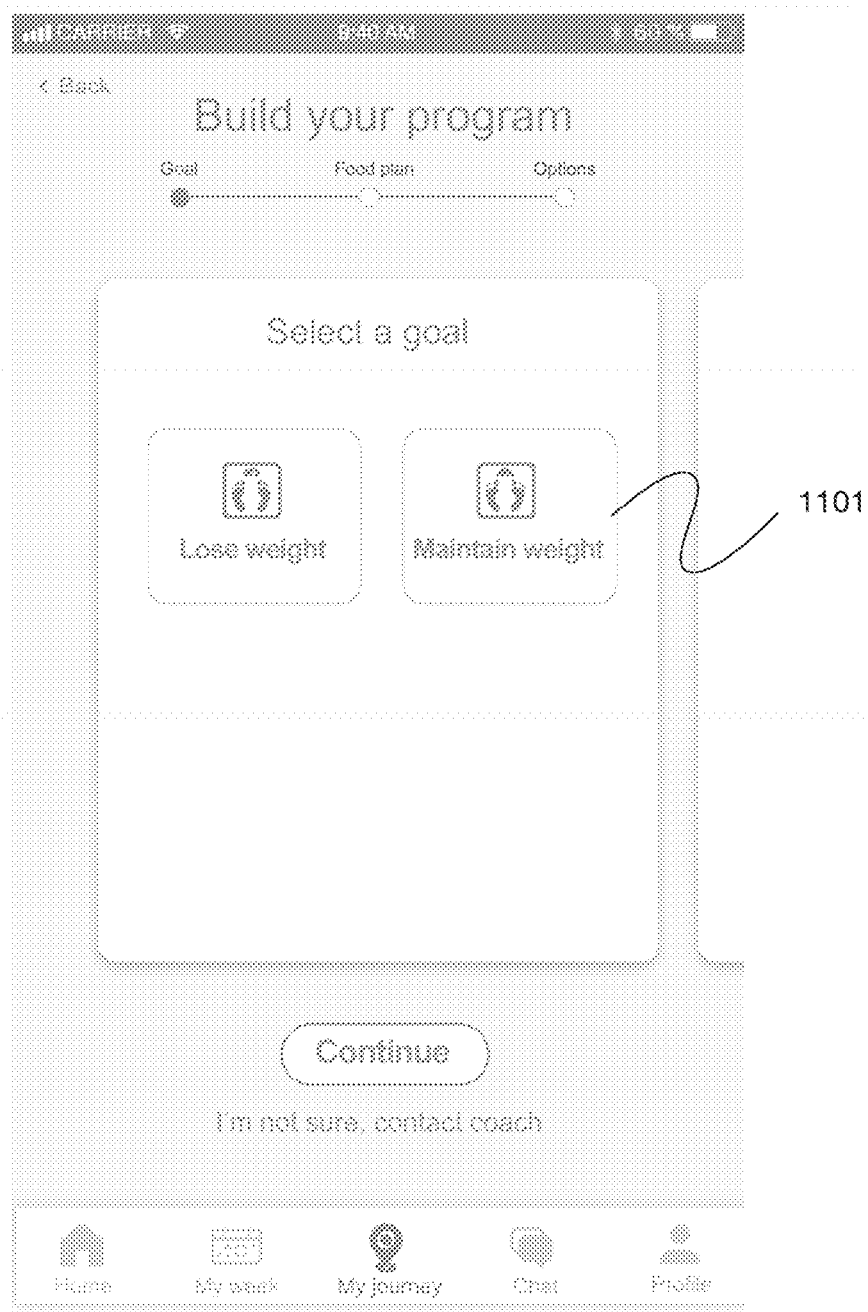
FIG. 11 illustrates an example screen display of the "my journey" page of the mobile application of FIG. 7.

In this embodiment, the user goal is set using the "Build a Program" feature shown on FIG. 11. (Here, there are only two goals, but the system can display far more than 2 goals). Once the user goal is selected, the user is taken to FIG. 14 to select his or her food plan. Then, the user adds any preferred accelerants on FIG. 15. Lastly, the user confirms his or her program via FIG. 12.

User Profiles

Users can be classified by the system in a number of different ways. Examples are described in U.S. patent application Ser. No. 15/466,287, filed Mar. 22, 2017; U.S. patent Ser. No. 14/690,756, filed Apr. 20, 2015; U.S. patent application Ser. No. 15/588,414, filed May 5, 2017; and provisional appl. 62/528,200, filed Jul. 3, 2017; which are incorporated herein in their entirety by reference.

In one example, users are classified into one of four metabolism profiles using an exemplary two-variable system involving a pre-determined ketone threshold ("Ketone Threshold") and a time period ("System Time"). The Ketone Threshold is set based on the program (for example, goal×food plan×accelerant) and, preferably but optionally, the values of others. In FIGS. 9A-9D, the threshold marker 901 is a level of 4 ppm (parts per million) in the case of breath acetone. This threshold marker 901 is determined based on the general results of a low carbohydrate diet, where reaching a dieting or fat burning state results in a baseline breath acetone level of 4 ppm. The user's ketone breath scores are charted for a minimum of 14 days, to determine how much time it takes for the user to generate high levels of ketones (suggesting enhanced lipolysis), if the user enters that state at all. The time that the baseline results are recorded for are indicated as System Time. Other values may also be used to determine the System Time. For example, if the system recognizes that general low-carbohydrate dieters take twenty-one (21) days to enter a fat-burning state, the user's baseline data may only be collected for twenty-one (21) days.

Figure 9A:
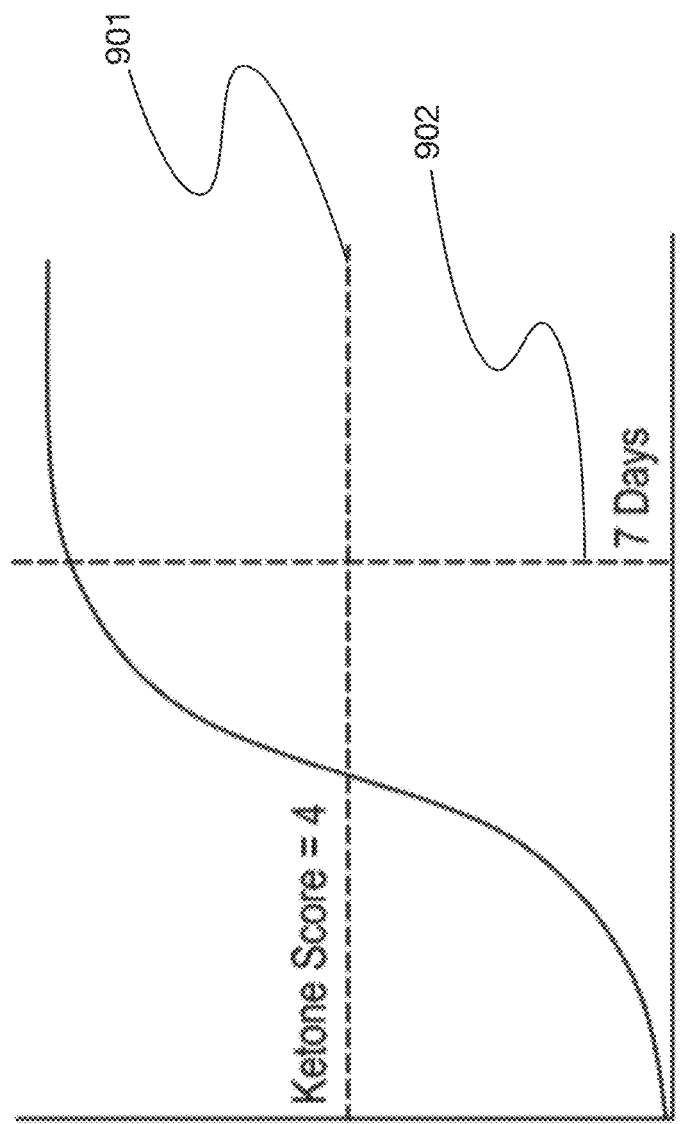

The first metabolism profile, shown in FIG. 9A, represents users whose ketone levels reach 4 ppm within the first seven days and stay well above that threshold. In Table 1 shown below, this is considered "Profile A." For these users, the system may provide coaching to the user on adding and subtracting exercise activities and modifying the user's diet. The diet modifications typically allow the user to increase daily carb intake beyond 20 grams. For example, the mobile application 32 may recommend foods that have a low glycemic index or are available at a restaurant that the user is visiting (e.g., "Your Ketone Score has been high over the past 5 days—nice job restricting your carbs. I see that you are going to Kona Grill, consider sharing a creme brûlée, which has fewer carbs and no starches. Stay away from the butter cake."). As another example, the mobile application may provide the following location-based messaging: "I see that you are at a sushi place. If you would like to have sushi tonight, have 3 pieces only. Then be sure to wear your heart rate monitor before leaving home tomorrow [remind user before the user leaves home]. Be sure to burn an extra 100 calories during your workout to compensate for the sushi that you ate [remind user during the workout]."

Figure 9B:
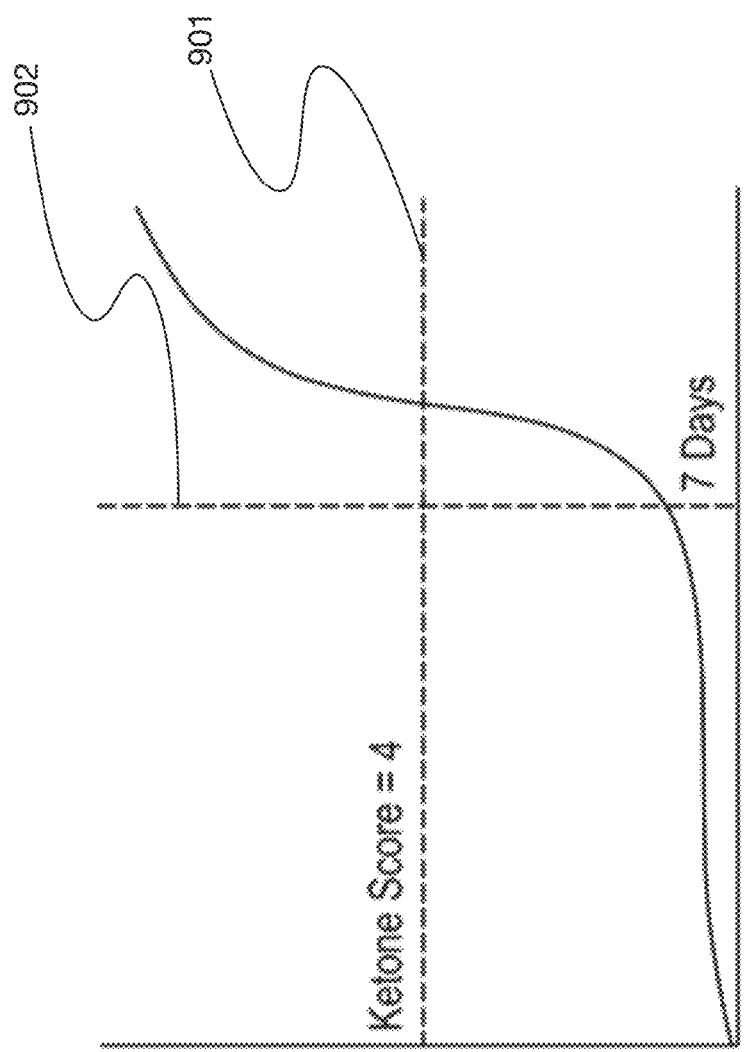

The second metabolism profile, represented by the graph in FIG. 9B, represents users whose ketone levels increase well above the threshold shortly after the seven-day period. In the table shown below, this is considered "Profile B." For these users, the system may again give the user the option to exceed 20 grams of carbohydrates and to modify exercise; however, the system may regulate the timing of such changes so that the changes occur at controlled time increments.

Figure 9C:
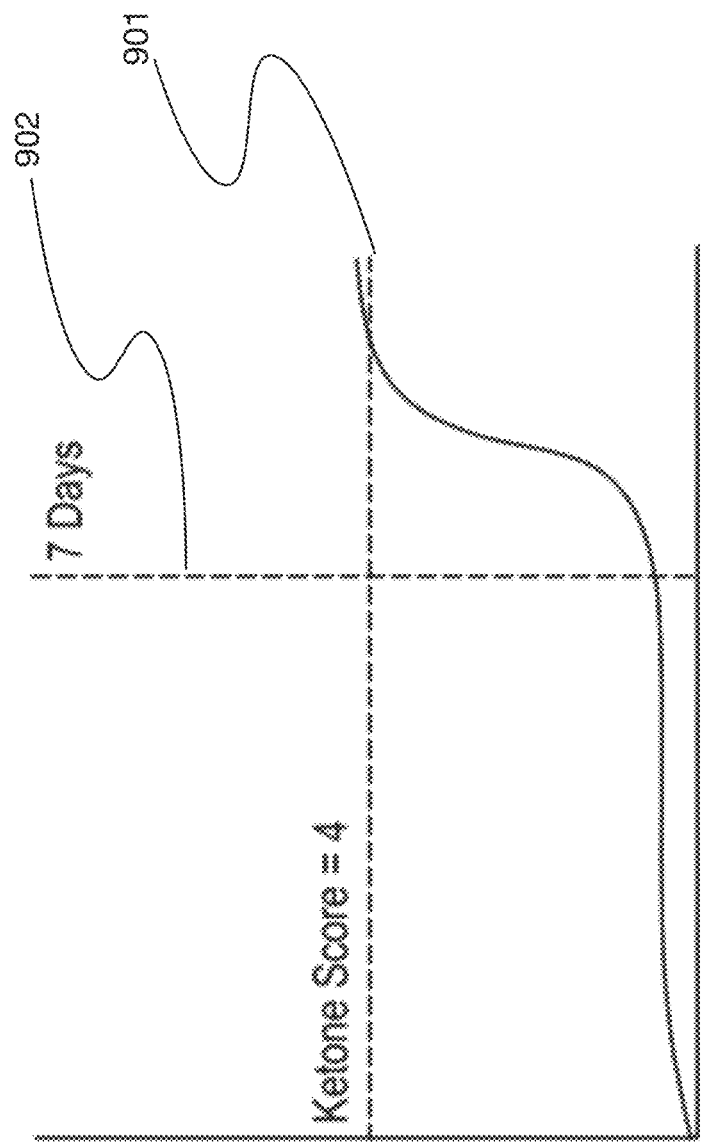

FIG. 9C illustrates a class in which the ketone score (KS) reaches the threshold of 4 ppm after 7 days and thereafter remains slightly above that level. In the table shown below, this is considered "Profile C." For these users, the system may instruct the user to keep daily carb intake below 20 grams until the ketone score (KS) reaches 7; the system may thereafter enable the user to experiment with diet and/or exercise changes as long as the ketone score remains above 2.

FIG. 9D represents a class in which the ketone score does not reach the threshold of 4 ppm during the relevant time period. For these users, the system recommends that the user maintain daily carb intake below 20 grams, and may enter into a "troubleshooting" mode that seeks to learn the reason(s) why the ketone score is staying low. The troubleshooting protocol may, for example, instruct the user to reduce calorie intake, to take ketone measurements more frequently, to generate glucose measurements, and/or to take other actions that are useful for determining the reasons for the low ketone level increase. Examples of such actions include: further decreasing carbs, increasing fat intake, seeing a physician for a blood workup and medication assessment, decreasing protein, removing artificial sweeteners, and initiating a fat fast. In the table shown below, this is considered "Profile D."

The system 40 may also use regression to identify or modify cut-off values used for classification. Examples of such cut-off values are the ketone score threshold of 4, and the time period of seven days, used in the categories of FIGS. 9A to 9D.

TABLE 1

| Profile & Description | User-Facing Explanation | Example Interactions |
|---|---|---|
| A: Rapid Fat Metabolizer | Clients like you generate high ketone scores in a short period of time. Usually you are able to lose weight quickly, but we have also noticed that similar clients tend to be prone to yo-yo dieting. We encourage you to watch your compliance score and set great habits! | Promote cheat meals to avoid boredom. Change the program frequently to avoid boredom. Emphasize high scores & daily monitoring. Don't allow the user to take "breaks" without planning ahead. |
| B: Rapid Fat Loss with Adherence | Clients like you are able to generate high ketone scores if your compliance is high. Usually you are able to lose weight quickly, but this is only when you stick with a program for chunks of time. Be careful about cheat meals-they can set you back. We encourage you to monitor your ketone score and note how long it takes you to recover from any "cheat" episodes. | Change the program frequently to avoid boredom. User will likely be successful on more than one program. Emphasize high scores & daily monitoring. Encourage the user to try accelerants to see superior results. |
| C: Burning Fat is Hard! Consistency is Key | Clients like you have a hard time generating high ketone scores even with adherence. However, clients like you tend to lose weight and keep it off long-term if you stick with habits. Daily monitoring is key. We encourage you to monitor your compliance score & keep your ketone score > 1 every day. Plan for this to be a journey. We're here for you! | Focus on score changes. What caused the drop? Emphasize consistency in monitoring. Downplay high scores & focus on slow & steady progress. Note any abnormalities in user reported information quickly when changing programs. This user needs to be very adherent. |
| D: Hard to Burn Fat | Clients like you have an extremely hard time generating high ketone scores. We have successfully worked with individuals like you, but it takes a lot of time and patience for the clients to see results. We would love to work with you, but you should expect to see slow results over a long period of time. We would encourage you to speak on the phone with a Coach to talk about what you can expect realistically. | Strong candidate to be paired with a high touch service (e.g., human coaching). Focus on score changes. What caused the drop? Emphasize consistency in monitoring. Downplay high scores & focus on slow & steady progress. Note any abnormalities in user reported information quickly when changing programs. This user needs to be very adherent. |

Profile A through D may be a simplified model to understand whether a client is more or less prone to glycogen versus fat utilization. The user's metabolism profile 801 may be displayed on the Profile screen (see FIG. 8) of the mobile application 32.

Food Plan

The food plan represents the base nutrition program that assists the user in achieving the user goal. The word "food plan" is not intended to convey a meal plan per se, but rather is the name of what was traditionally referred to as a "diet." But since not all individuals would be interested in losing weight, we are using a broader word of a "food plan." Essentially a food plan is a set of rules regarding nutrition that are intended to guide a user to achieve his or her goal.

Examples of food plans are: Mediterranean, Paleo, ketogenic, low carb, FODMAP, alkaline, alkaline 80/20, autoimmune protocol, Ornish, low arginine and high lycine diets, and others.

Figure 12:
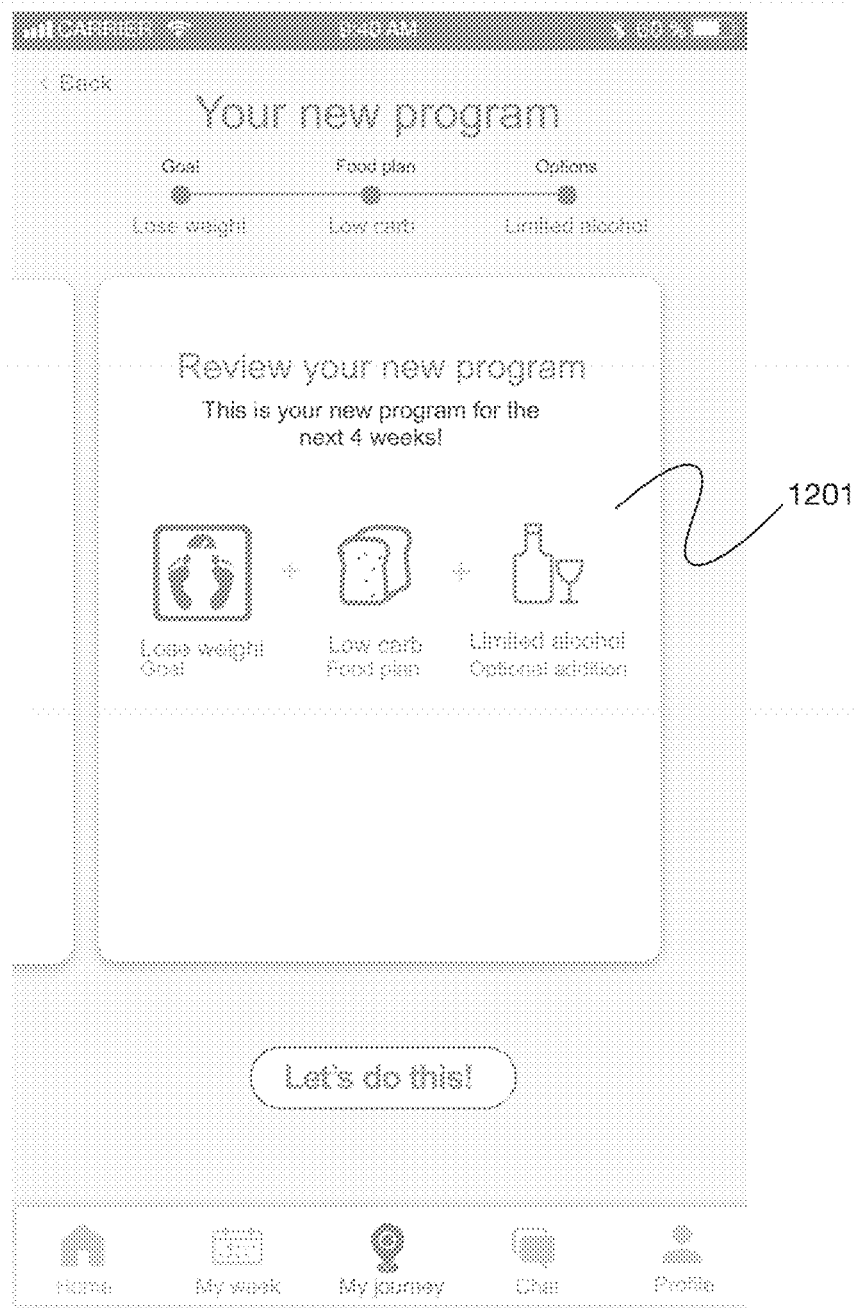
FIG. 12 illustrates an example screen display of the "my journey" page of the mobile application of FIG. 7.
Figure 14:
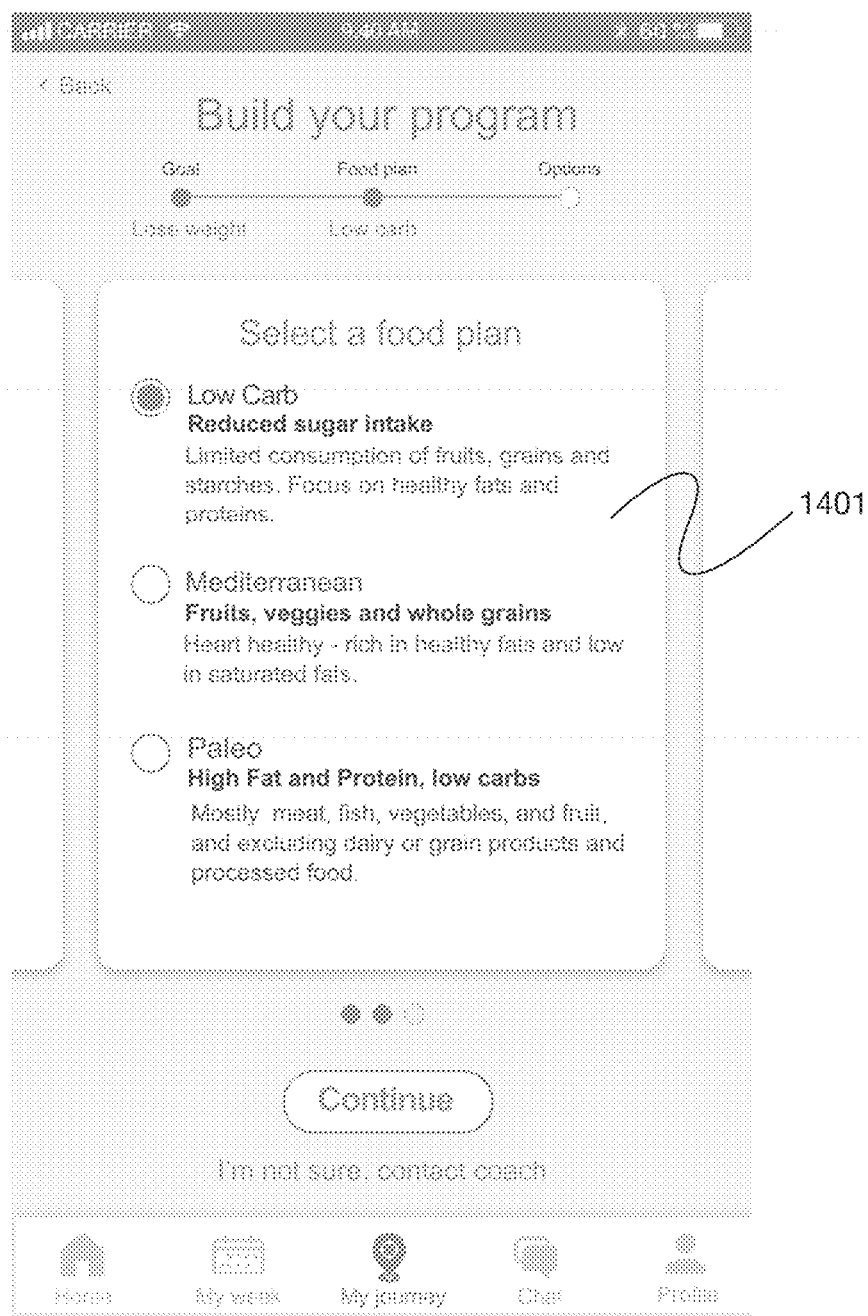
FIG. 14 illustrates an example screen display of the "my journey" page of the mobile application of FIG. 7.
Figure 15:
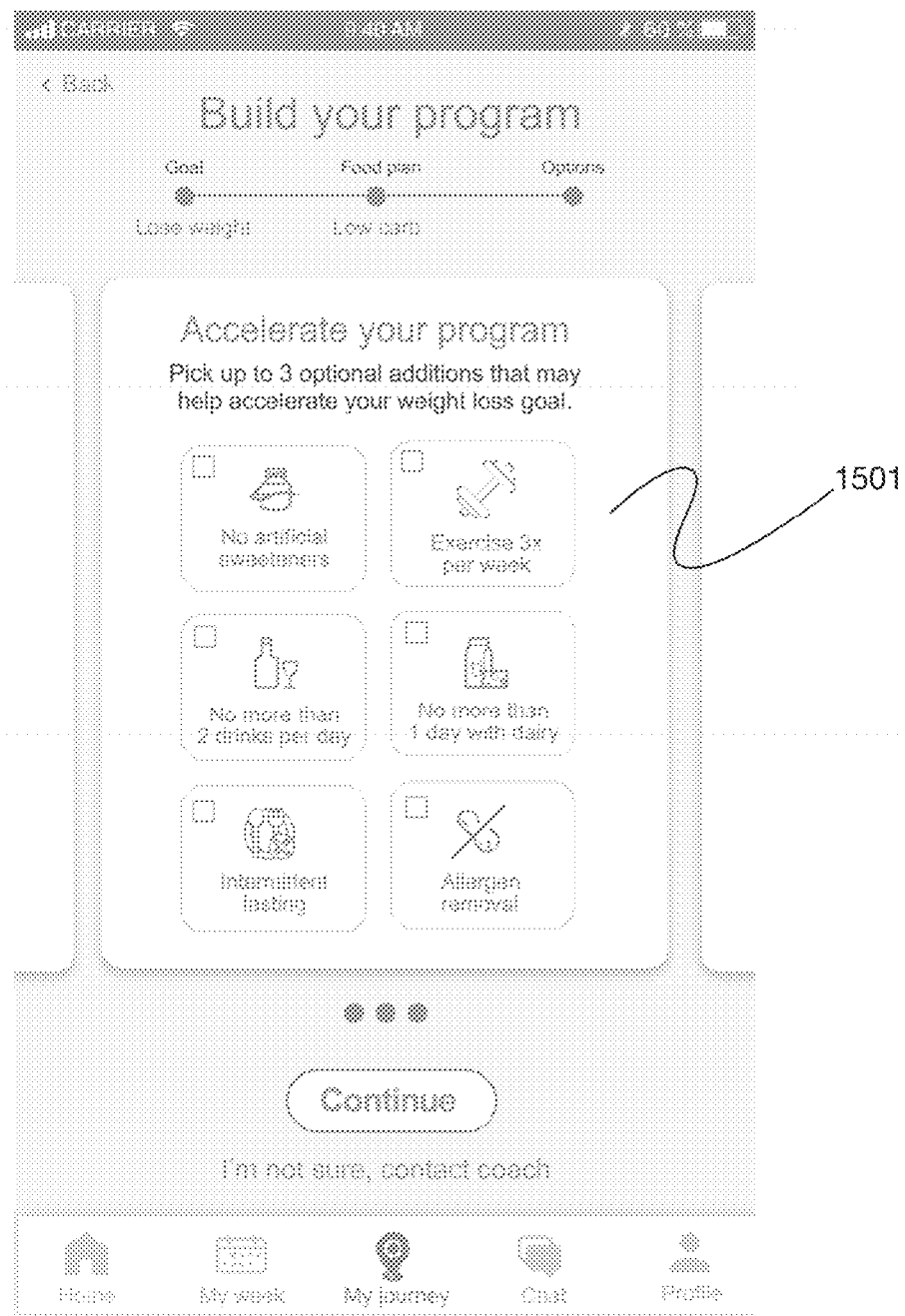
FIG. 15 illustrates an example screen display of the "my journey" page of the mobile application of FIG. 7.

Preferably, the user begins on a baseline food plan, such as low carb, to complete the metabolism profile. Thereafter, the user is encouraged to change his or her program overall every 4-12 weeks. This may and likely will mean changing the food plan. FIG. 11, FIG. 14 and FIG. 15 show the selection process to build a program overall and FIG. 12 is the selection of the food plan. It is important to note that the System may select a program or a food plan for the user and simply ask the user to accept the select or merely notify the user of the change.

Accelerant

Accelerants are not substitutes or replacements for food plans, but rather help boost the impact of the overall program, so that the user can achieve their goals sooner. Accelerants facilitate or accelerate achieving the user's goal, but rely on adherence to the food plan to achieve the principle goal. A classic example of an accelerant is exercise. One may argue that exercise can help people lose weight, but it is generally accepted that a person who is exercising but making very bad food choices will not see weight loss. As such, exercise is an accelerant to help someone achieve weight loss goals, but atop an appropriate food plan.

Examples of accelerants are: exercise, intermittent fasting, planned cheat meals, decreased alcohol consumption, decreased dairy consumption, decreased stimulants (e.g., coffee/caffeine), consumption of supplements (e.g., BCAs, magnesium, etc.), and others.

It is important to note that accelerants may also include: attention to sleep hygiene and stress removal. Although improved sleep may also be a user goal, it may also be represented as an accelerant to enhance weight loss. Thus, even if a user is not focused on improving his or her sleep as a specific goal, he or she may benefit from improving sleep to enhance weight loss. This accelerant may be monitored via a sleep hygiene checklist (e.g., no activity with your mobile phone after 8 pm) or purely by result (e.g., results of a sleep monitor). Decreased stress may be monitored via the user's resting heart rate or average heart rate. Decreased stress may also be monitored by third party reports (e.g., reports from the user's social community).

FIGS. 11, FIG. 14, and FIG. 15 show the selection process to build a program overall and FIG. 15 is the selection of the accelerant. It is important to note that the System may select a program or an accelerant for the user and simply ask the user to accept the selection or merely notify the user of the change.

User-Input Information

The user inputs certain information to demonstrate his or her adherence to the food plan and accelerants. While we could use food journals or other means to log food intake (e.g., photographic input of food), preferably the user input is minimized.

In this example, the user's program (goal×food plan× accelerant) is abstracted into parseable pieces. For example, Paleo=no processed foods+no dairy+no legumes. In this way, the user is not required to report everything he or she did, but rather simply enough information to determine if the user complied with the specified program. Continuing with the example, instead of the system asking the user if she adhered to no dairy, no legumes, etc., the system may simply ask the user if she adhered to the Paleo food plan.

If the user is not seeing results with this type of approach, the system may prompt for the user to use more aggressive data entry. This may be especially useful for an individual who is learning from basics.

To determine that more aggressive data entry is necessary in one embodiment, the system checks to see if the user's program score is within a certain range. If the program score is not within a certain acceptability range, the system may automatically request more aggressive/detailed data entry to enable the system, or a subject matter expert, to provide better and higher quality advice. The acceptability range may be a fixed range for all users, customized on a user-by-user basis, or dynamically calculated based on the user's past behavior. For example, if the rolling 5-day average is less than the rolling 30-day average, the system may determine that something is going wrong and may start requesting additional information.

In certain embodiments, the user is required to input "user input information" before seeing his or her ketone levels. This forces the user to log the minimal information necessary to help interpret the levels or simply helps the user be more aware of his or her behavior from the preceding day.

In some embodiments, the ketone measurement device does not have a physical display; thus, the measurement result can be masked until the "user input information" is received—in such an example, the App remains the primary display. Alternatively, the display does not show the result until the system receives the user input information.

In other embodiments, the user is required to input "user input information" before performing a ketone measurement. This method prevents bias when the user inputs information after he or she knows the output of the breath ketone test. This also forces the user to log the minimal information necessary to help interpret the levels, and allows the user to review the behaviors preceding the breath ketone test.

It is important to note that the user-input information may be obtained from sources other than a daily log. For example, if a particular parseable piece of information can be determined through other sources, this other source may be used. For example:

Exercise (elevated HR for >15 minutes)
Exercise (GPS location at a known gym and user's location there for >15 minutes)
No dairy (user's credit card shows food purchases only from a designated meal delivery service that is known to be dairy free)
Weight (wireless bathroom scale)
Sleep data (wireless sleep monitor)
Breath alcohol analyzer (no alcohol before bed)
No missed medication (wireless pill dispenser)
Third party audit—e.g., friend reports (no cheat meals)

Program Score

Displaying ketone data by itself poses some challenges in practice. For example, if someone gets a breath acetone level of 5 ppm and maintains that for 30 days, this may or may not help the user make and adhere to changes. Additionally, if the user sees significant score fluctuations, it may not be helpful to the user to see the numbers without context. Thus, the user interface optionally but preferably includes some additional feedback beyond only the ketone level. This may include a program score or the number of days that the user has had a ketone level above a certain threshold.

This is a key visualization for wellness devices with broad application beyond just ketone monitoring. The vast majority of medical information is presented to focus on "bad" data, outliers, suggestions of abnormalities or warning flags. In the context of wellness data, although it is important to highlight anomalous data, maintaining control and seeing little to no fluctuations is actually of greater importance. This difference propagates into success criteria used in machine-based processes, changes the focus from catching a single outlier to looking for sustained trends (thereby changing data used for algorithmic efficiency) and fundamentally changes the user interface. No longer is it of paramount importance to report: your glucose level is 300 mg/dL— see a physician. But rather, you have maintained glycemic control for 97 days. A display of raw good data may be boring for the user, resulting in decreased engagement—essentially visualizing a "flat" line (showing results within a normal range). This concept of using a Program Score, thus, has broad implications to wellness devices and represents a fundamental shift in data visualization as well as use of data for computational purposes.

In one embodiment, the user is presented with a program score, where the score incorporates user input information as well as ketone levels. There are other embodiments in which the program score does not require regular performance of a breath test, but either uses information from another PMA or SPP or alternatively utilizes the parseable information (and related computational efficiency) described later herein. (The terms PMA and SSP are used as in U.S. application 62/528,200 entitled: "Automated Processes for Detecting and Addressing Health Issues Based on Monitored Analytes and Other User Data.") But preferably the Program Score includes breath acetone information.

In this example, the program score is comprised of three elements: (Element 1) the ketone level; (Element 2) whether the user performed a ketone test; and (Element 3) adherence to the parseable components of the program (e.g., the elements of the food plan or the accelerants).

The computation of the program score may vary depending on the user's metabolism profile (e.g., Profile A through Profile D, described elsewhere). As an example:

Program Score=Element 1+Element 2+Element 3
Profile A=60%+30%+10%
Profile D=30%+30%+40%

Table 2 shows an example breakdown of the goals, food plans and accelerants available for a user to select.

TABLE 2

| Goal (must pick 1) | Food Plan (must pick 1) | Accelerant (can pick up to 3) |
|---|---|---|
| Lose Weight | Low Carb | Exercise |
| Maintain Weight | Mediterranean | Limit Alcohol (not an option for some users) |
| | Paleo | Limit Dairy |
| | | Limit Artificial Sweeteners |
| | | Intermittent Fasting |
| | | Allergen Removal |

Table 3 shows exemplary user prompts that are associated with different habits within the system. For different program elements (i.e. food plans and accelerants), different habits need to be monitored in order to determine adherence to the program. Habit adherence is determined by providing questions to the user on a daily basis that correspond to the behaviors that need to be followed. For programs that include multiple elements, the "Total Habits" are calculated by adding up the habits for each element. As an example:

User A is on a weight loss program, using a Mediterranean food plan and exercise as an accelerant.

Habits for Mediterranean+Habits for Exercise=6 Habits (for Medit.)+2 Habits (for Exercise)=8 Total Habits (see Table 3)

Thus, the user is asked 8 questions to calculate habit adherence.

Note that the first row, titled "all food plans," are used for data entry, and are required from each user. These are not computed into the user's habit score. But these are used to generate context for fluctuations in the ketone levels and also to generate tips.

Regarding the computation of habit adherence, some habits may be weighed in an "all-or-nothing" fashion. This means that if a habit is adhered to, the user receives 100% credit for that habit, and if the habit is not adhered to, the user receives 0% towards their habit adherence score. Referring to the Mediterranean example in Table 3, the user is asked if she consumed red meat. The user selects between one (1) of two choices, which results in either 0% or 100% credit. Other habits are weighted based on the degree to which the habit was achieved, which means that the user is awarded different degrees of credit. Referring to the "Low-Carb" example, the user is asked how many carbs were eaten for the day. The user selects between one (1) of three choices, which results in either 0%, 75%, or 100% credit. The weights assigned to the applicable answer choice is shown on the rightmost column.

TABLE 3

| Habit Category | Question | Answer Choices | Habit % |
|---|---|---|---|
| All Food Plans* | Glasses of Alcohol[1] | 0, 1-2, 3+ | Note that this information is logged, but not included in habit compliance. |
| | Packets of Artificial Sugar[1] | 0, 1-2, 3+ | |
| | Any Cheat Meals? | Bad Day, Bad Meal, Nope! | |
| Food Plan-Low Carb | Carb Count | <20 g; 20-30 g, 30 g+ | 100/75/0 |
| Food Plan-Mediterranean | Good Portion Control? | Yes! Not Today | 100/0 |
| | Any Red Meat? | Yes No | 0/100 |
| | Any Preservatives? | Yes No | 0/100 |
| | Any Refined Sugars/Grains? | Yes No | 0/100 |
| | Low Fat Dairy? | Yes No | 0/100 |
| Food Plan-Paleo | Good Portion Control? | Yes! Not Today | 100/0 |
| | Any Preservatives? | Yes No | 0/100 |
| | Any Refined Sugars? | Yes No | 0/100 |
| | Dairy Free? | Yes No | 100/0 |
| | Legume Free? | Yes No | 100/0 |
| | Grain Free? | Yes No | 100/0 |
| Accelerant-Exercise | Workout-CV | 16-30 min, 30-60 min, None | 3X/week for either of these = 100% |
| | Workout-Strength | 16-30 min, 30-60 min, None | |
| Accelerant-Limit Alcohol[1] Drop alcohol question. Replace with: | Wine | None, 1-2, 3+ | 100/50/0 |
| | Hard Liquor | None, 1-2, 3+ | 100/50/0 |
| Accelerant-Limit Artificial Sweeteners[1] Drop AS question from base diet program. Replace with: | Artificial Sugar Drinks | 0, 1-2, 3+ | 100/50/0 |
| | Artificial Sugar Non-Drinks | 0, 1-2, 3+ | 100/50/0 |
| Accelerant-Intermittent Fasting | Fasting Duration | None, 12 h, 16+ h | 0/50/100 |
| Accelerant-Limit Dairy | Dairy Intake: | None, Only Goat Cheese, Dairy | 3X/week = 100% |
| | Nightshades | Had Them Skipped | 0/100 |
| Accelerant-Allergen Removal | Preservatives? | Yes No | 0/100 |
| | Nuts or Seeds | Had Them Skipped | 0/100 |
| | Soy? | Yes No | 0/100 |
| Accelerant-Controlled Cheat Meals | Done in <90 min? | Yes No | 100/0 |
| | Balanced meal? | Yes No | 100/0 |
| | Was it planned? | Yes No | 100/0 |

The breakdown of diets into parseable pieces is a key difference between the approach described in this disclosure as compared to the present state of the art. At this time, diet journals are used by virtually all weight loss or nutrition programs. This imposes a hefty burden on a user to log throughout the day and also to log correctly. Conventional diet journals use look-up tables, which adds a level of complexity and is error-prone. What's more, the same diet journal is used regardless of whether the user's "diet" program has changed—thus, the user may have little to no awareness of what parameters, whether it is calories, macronutrients, salt consumption, or others, that are being evaluated for success.

The breakdown into parseable pieces enables key UI implementations that enable users to enter data more efficiently, accurately, and consistently. Many UI implementations for logging and journaling are in the form of free-form text fields, autocomplete search, or hierarchical navigational trees that are very deep. All of these implementations typically require the user to use a full keyboard for text entry, which is slow, requires two hands, requires the use of a device that has keyboard support, and requires the user to launch and use an app on their mobile device. On the other hand, the breakdown of the diet into parseable pieces enables the UI implementation to simply present a multiple choice set of options, as in FIG. 10. The user only needs to tap on their response rather than type. Not only is this faster, it requires just a single hand, can be ported and used on devices that do not support keyboard entry (for example, smart watches), can be implemented using mobile push notifications in which messages appear directly on the lock screen of the user's device and allows to user to submit a reply without needing to unlock their phone. All of these improve the efficiency of the system and the UI implementation.

Additionally, the breakdown into parseable pieces makes the computational and storage requirements of the backend systems more efficient. As aforementioned, most data journaling and logging systems rely on textual input. Text input is notoriously error prone. People make spelling mistakes, they use different words to mean the same thing, and there are cultural and idiomatic nuances to their word choice. To compensate for this, most logging and journaling systems deploy sophisticated natural language processing functionality which require a lot of storage space (for example, to store dictionaries and corpuses of all known words), computational time (for example, to pre-compute adjacency matrices to be able to identify similar words or common misspellings), and network capacity (for example, many datasets are too big to fit onto a single machine so networking implementations are needed to shard the data across several machines). By breaking down diets into parseable pieces, the computational, storage, and network efficiency of the system improves.

We chose to abstract the food plans into the "rules" so the user is able to directly associate what he or she is supposed to do with the designation of "success." When a program is changed, based on the methods/processes described herein, the rules/habits and the designation of success is correspondingly changed. To clarify, the rules that individuals on the following programs will follow and the corresponding computation of the "Habit" percentage (see, e.g., Table 4, Column 3) varies:

Food Plan [Low Carb]+Accelerants [null set]
Food Plan [Low Carb]+Accelerants [Exercise]
Food Plan [Low Carb]+Accelerants [Exercise, Intermittent Fasting]
Food Plan [Paleo]+Accelerants [Exercise, Allergen Removal]
Food Plan [Mediterranean]+Accelerants [Dairy Removal, Limit Alcohol]
Food Plan [Mediterranean]+Accelerants [null set]

Figure 19:
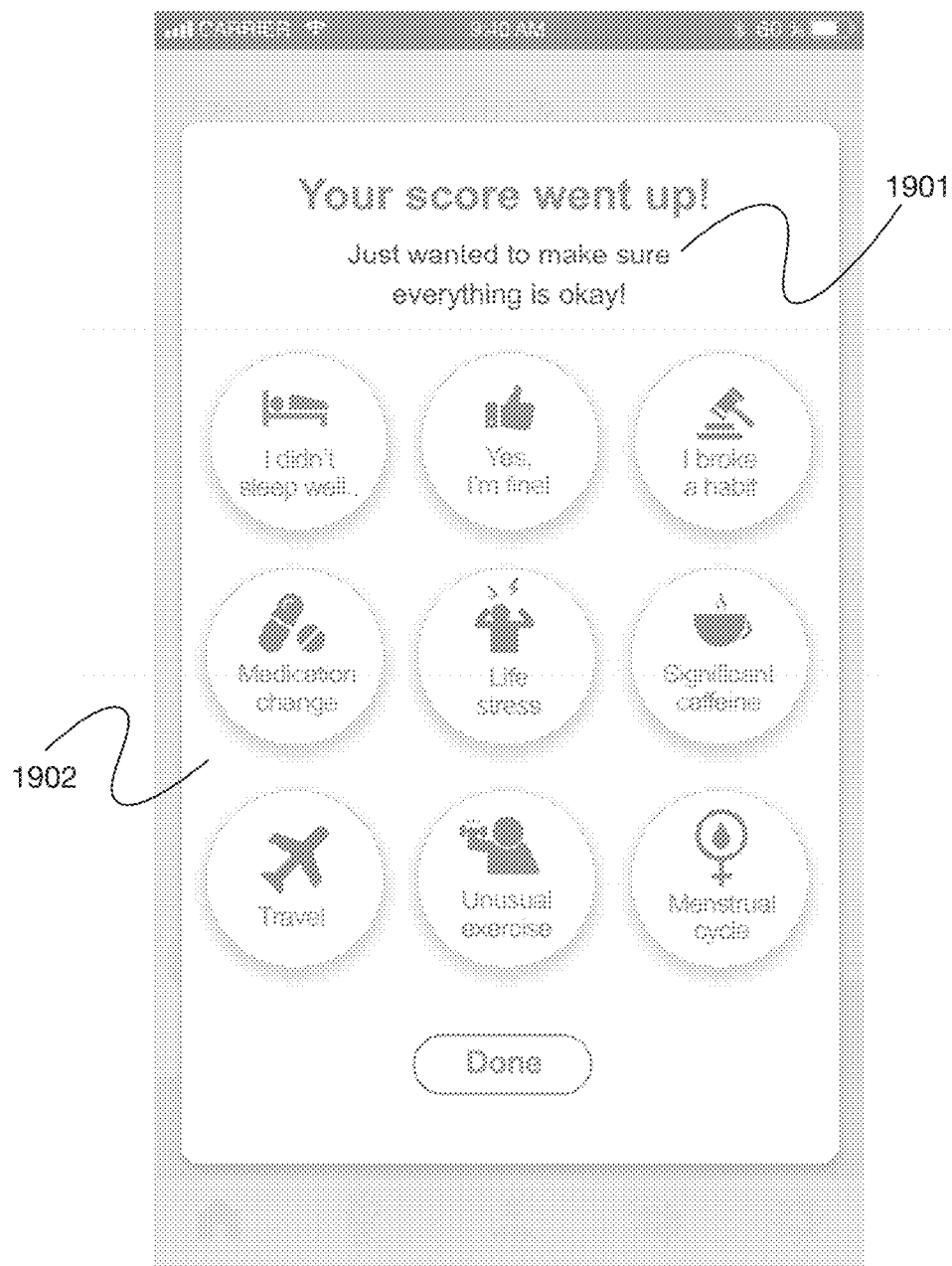
FIG. 19 illustrates an example screen display of the "coaching" feature of the mobile application of FIG. 17.

The "rules" that appear may vary as the system begins to recognize reasons for increase in ketone scores from successful users on a particular program. This would be collected using a prompt when there are increases in ketone levels, e.g., using a screen as depicted in FIG. 19.

Over time, as a user shows mastery of a particular habit set, the System may prompt the user: "Do you want to collapse the daily inputs that you are following?" If the user selects yes, he or she may simply have a reduced question set like: "Did you follow your food plan yesterday? Yes or No" and "Did you follow your accelerant yesterday? Yes or No". This further reduces the information that a user needs to log.

In the broader context of data management, this user interface is superior in that it is substantially less time intensive (seconds instead of minutes), it maximizes the chance that the database obtains accurate information (user-completed diet journals are notoriously inaccurate), and the information solicited from the user is directly tied to success.

Table 4 shows the relationship between the user response and the computation of the Program Score.

TABLE 4

| Profile | Breath Test? Element 2 (If done, 100%. Else, 0%) | Breath Test Result Element 1 | | Habits (Average of Applicable Habits) Element 3 |
| --- | --- | --- | --- | --- |
| A | 50 | 30 | >=5 | 20 |
| B | 30 | 40 | >=3 | 30 |
| C | 30 | 40 | >=3 | 30 |
| D | 50 | 20 | >=2 | 30 |

Finally, the Displayed Program Score may be a weighted summary of historical Program Scores. In this example, the Program Score is 60% based on today's data, 30% based on yesterday's and 10% based on the prior day.

Assuming user that is classified as Profile A, the computation of today's Program Score is:

Today's Program Score=50 (100% of 50; user performed a breath test)+30 (100% of 30; user got a ketone level>=5)+10 (50% of the habits were followed. 50%*20=10)=90.

If yesterday's Program Score=80 and the day before was a Program Score=20 (because the user did not perform a breath test), the Displayed Program Score is:

Displayed Program Score=Today*60%+Yesterday*30%+Day Before*10%

Displayed Program Score=90*60%+80*30%+20*10%

Displayed Program Score=80

It is important to note that "success" for a Profile A user is a score>=5 whereas "success" for a Profile D user is a score>=2. It is important to reward and penalize users appropriately, based on his or her physiology. As such, setting unrealistic goals is not helpful. The specific score threshold is may be generated using machine learning using algorithms and processes described elsewhere herein. Although the aforementioned example uses the user's baseline data as the sole basis for creating the Profiles, taking into account the user's historical data, other health data, and the program that the user is on will aid in defining a meaningful ketone threshold for a given user to achieve.

Referring back to Table 3, the rule set that underlies the food plan may vary depending on the user goal. For example, "low carb" or "ketogenic" may be <20 g total carbs for weight loss and may be <80 g net carbs for general maintenance.

The food plan may also vary depending on the demographic of the user. For example, "low carb" for a post-menopausal woman seeking to lose weight may be <20 g total carbs, but "low carb" for a college athlete seeking to lose weight may be <50 g total carbs. Similarly, "autoimmune protocol" for an individual with advanced rheumatoid arthritis and >55 years of age may be strict adherence to removal of legumes, seeds, and nightshades, whereas such a protocol for an individual with early onset rheumatoid arthritis may be more focused on just removal of legumes.

The weights of different elements of the program score may be adjusted for the user, depending on changes in the user's program. If the user switches to a different food plan or accelerant, the program score computation is modified based on those changes. As the system recognizes trends in the user's data, the system may also recommend changes in the user's program score computation. For example, the system may recognize over a period of time that the user maintains high ketone levels, but does not adhere to program behaviors. As a result, the system may adjust program score computation to place more weight on program behavior adherence. This will serve as motivation for the user to focus on adhering to program behaviors in order to boost their program score.

It is important to note that the concepts described in this disclosure discuss the need for ketone levels and/or an alternate metabolic indicator, but the use of parseable data is independently unique. Parseable user data may be used with other data, e.g., heart rate, financial transactions, or third party reports (e.g., friend confirmations or expert confirmation) without use of ketone levels to generate a Program Score.

Machine-Based Processes

In some embodiments, the mobile application 32 may periodically ask the user one or more questions (e.g., "are you hungry?", "what is your weight?") to assess the user's progression towards achieving his or her goals. This may also be used to determine the effectiveness of the current program, and may record the user's answers. The effectiveness of a current program is expected to change even for a given user with time—in other words, a program that worked for a given user may not be effective after a certain period of time due to boredom, diet fatigue, or physiological adaptation.

There are certain classifiers that aid in determining whether a program change is warranted. Examples include:
Suggesting diet fatigue or boredom
Repeat 0s
Persistent drops in ketone levels (e.g., 5→2; 6→3; 2→0)
Missing tests
Resurgence of symptoms that were once removed (e.g., user is doing a test sporadically suggesting that he or she is not sleeping regularly; user reports of nausea or low energy, etc.)
Time (e.g., 8 to 12 weeks later)
User's social support is making a change (e.g., all of the user's friends are now doing intermittent fasting or have switched to a goal of weight maintenance)
Purporting to change the overall program (e.g., goal+ food plan+accelerant) frequently (e.g., more than once in 4 weeks)
Suggesting physiological adaptation
Progressive decrease in ketone levels (e.g., 6, 5, 4, 2, 2, 0, 2, 0, etc.)
"Plateau" in achieving user goal (e.g., weight loss or high energy)
Time (e.g., 8 to 12 weeks later)

Further, the mobile application 32 may include a "daily journal" or "daily questionnaire" feature through which the users can record various types of information and events. For example, users may specify that they are low on energy, hungry, constipated, or unhappy, or that they have deviated from their program. In one embodiment the mobile application prompts the user to assign a numerical rating to each of the following: (1) weight, (2) energy level, (3) focus, (4) hunger, (5) hours of sleep per night, (6) joint pain, (7) digestive issues, and (8) boredom.

The mobile application 32 may report these and other types of user information to the system 40 for use in providing personalized, machine-automated coaching. Further, in some embodiments the coaching may be supplemented or filtered by a human coach, in which case updates from the human coach may be recorded by the system and, in some cases, used by machine learning algorithms to improve the system.

In some embodiments, the system 40 may also be able to acquire other types of data about the users. For example, some users may use wireless glucose monitors that report glucose measurements to the health coaching system 40 via the mobile application 32 or via another channel. As another example, in the context of a weight loss program, the users/participants may use wireless scales that report their weight measurements to the system 40 via the mobile application 32 or otherwise. In one embodiment, the wireless scale, upon taking a weight measurement, wirelessly transmits the weight measurement to the mobile application 32 without displaying the measurement, such that it is withheld from the user; the wireless scale in this embodiment may lack a display.

As another example in the context of weight loss programs, the mobile application 32, or a separate mobile application (such as MyFitnessPal or Lose It), may enable each user to track, and report to the system 40, their food intake and exercise activities. Other possible data sources include blood test results, heart rate data, location data (reflecting of visits to restaurants or gyms), credit card transaction logs (reflective of restaurant visits), sleep logs, the user's home address (reflective of what types of exercise the user may comfortably take part in because of weather patterns), and web search logs (reflective of user being hungry). Further, personal profiles (which may be stored as, for example, database records or text files) may be created by the system by the users themselves and/or their coaches, and may be considered by the system in providing coaching. These personal profiles may, for example, include demographic data (age, gender, ethnicity, etc.), weight loss (or other health-related) goals, genetic testing results, medical history data, and various other types of information.

As described below, the health coaching system 40 may use the above and other types of user/participant data to generate personalized recommendations and programs for the participants. In some cases, the coaching may be interactive in the sense that the system enables the user (or a health or weight loss coach of the user) to select from multiple options for attaining a desired goal. For example, a user may opt to want to lose weight as quickly as possible instead of a less aggressive strategy. Additionally, a user may indicate to the system 40 certain personal preferences, idiosyncrasies, and desired activities that the system 40 may take into account. For example, the user may indicate that they regularly go to the gym and lift heavy weights, that they bike to work, or that they really like or dislike certain types of foods. The recommendations may also be based on the current location of the user (as detected by the mobile device using a GPS receiver or other location-detection technology), and the proximity of that location to restaurants, gyms, the user's house, etc.

For purposes of illustration, the system 40 will be described primarily in the context of a weight loss program. As will be recognized, however, the underlying processes are also applicable to automated health coaching involving other types of conditions (such as diabetes and anorexia). For example, the system may support the ability for the user to select from the following types of goals: (1) lose weight, (2) gain weight, (3) enhance athletic performance, (4) treat or reduce the severity of some other medical condition, (5) learn more about how the participant's body reacts to various foods.

Figure 3:
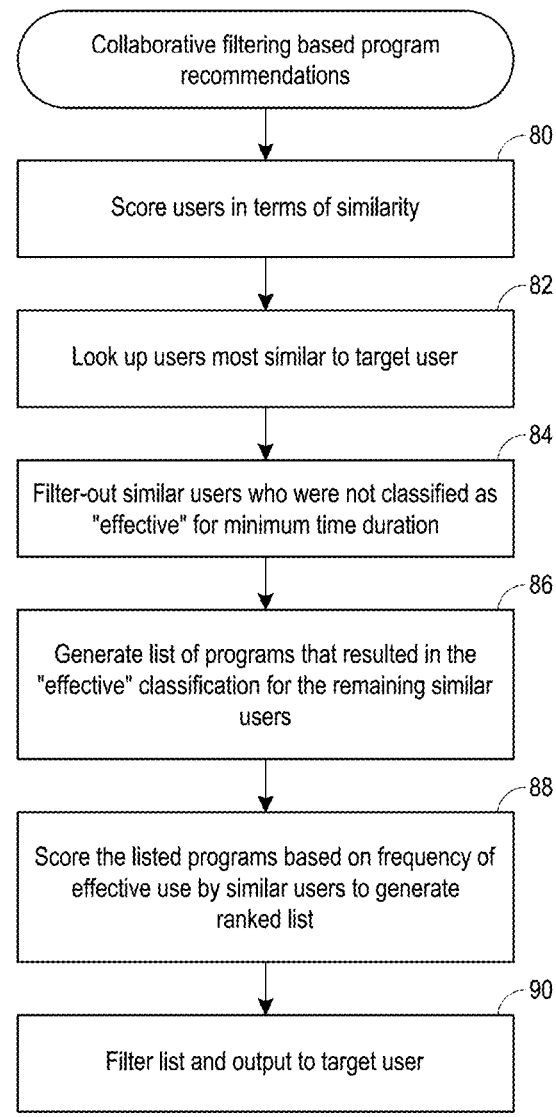
FIG. 3 illustrates a collaborative filtering algorithm that may be used to generate health program recommendations.

As further shown in FIG. 1, the health coaching system 40, in one embodiment, includes a trained model 42 that classifies users based on their ketone measurements and/or other user data. The trained model 42 classifies the users based on their data records 44 and a database of user class definitions 46. Each user data record may include, for example, a timestamped history of the user's ketone measurements (and any other measurements such as weight, glucose level, heart rate, etc.); demographic data such as age, gender, and height, and other user-supplied data such as medications taken; a timestamped history of the classifications and weight loss (or other health) programs assigned to the user, including program updates and recommendations generated by the system; weight loss goals; lifestyle habits; personal preferences; food intake events; exercise events; diet non-compliance events; user feedback on program satisfaction; nutritional sophistication level; etc. For some types of data, the users may provide the data to the system 40 by entering it into the mobile application 32, a web-based portal, or other data collection interface. Although the use of a trained model 42 is preferred, in some embodiments the system 40 may classify users, or otherwise make program recommendations, without the use of a trained model. For example, as described below with reference to FIG. 3, the system 40 may generate program recommendations using a collaborative filtering algorithm that seeks to recommend programs to a target user that have been effective for similar users.

Importantly, although the aforementioned figures show a client server model, a distributed peer to peer model may be used alternatively or in addition. And, that distributed model may use cryptographically-enabled distributed ledger akin to a blockchain.

A given user may be assigned to multiple classes concurrently, and the task of classifying a given user may, in some embodiments, be repeated whenever a new ketone measurement (or other significant data point) becomes available. Because a user's classification may change over time, the trained model 42 may assign classes as a function of other external parameters that exist outside of the user's data record. For example, the model 42 may be a function of the user's data record and a "target date" and the classes, 46, returned by the model, 42, may be interpreted as the classification of that user at the particular date. In one embodiment, some classifications assigned by the classifier 48 are of the user (or user data record) generally, and other classifications are of the effectiveness of a given program assigned to the user. An example of the later type of classification is an "effective" classification, which indicates that the health program assigned to the user is producing desired results. "Effective" may mean that the user is achieving his or her goals or that the user is merely compliant and seems engaged.

Figure 2:
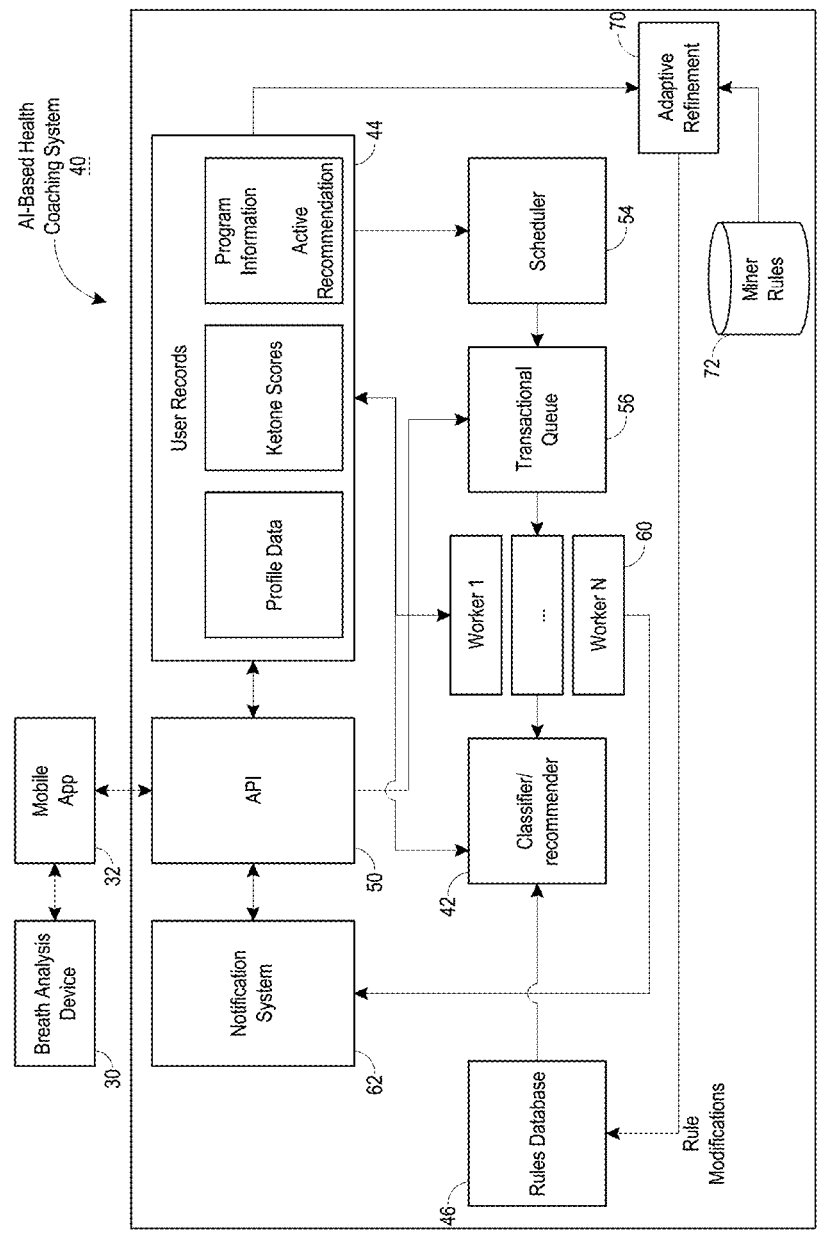
FIG. 2 illustrates a computer architecture that may be used to implement the system of FIG. 1.

In some embodiments, the classifier 48 may use a set of rules to classify users and to select actions to be performed. Some rules may, for example, be triggered by the receipt of a submission from a user's mobile device 32 of a ketone score, or other data point, that can potentially affect the user's current classification. An example of such a rule is one that determines whether the user's recent ketone scores justify a new categorization. Other rules may, for example be triggered by the reclassification of a user. For example, when a user is reclassified (such as from "effective" to "non-compliant"), a rule may be invoked that selects a new diet/exercise program for the user or that notifies a coach for the user. Other rules may, for example, be invoked periodically (e.g., once per week) based on the passage of time. A preferred embodiment of a rule-based implementation of the system is discussed below with reference to FIG. 2.

The class definitions 46 are selected or generated such that the class or classes to which a user is currently assigned are linked to particular recommendations (e.g. "reduce daily carb intake by X") and/or coaching protocols. These recommendations may be provided to the user by the mobile application 32, by a web portal, via text messages, and/or by any other communication method. The class-based recommendations may be generated by the health coaching system 40, the mobile application 32, or a combination thereof. Some classes may be defined manually by physicians and other experts, while others may be generated or inferred automatically using machine learning methods. Examples of classes (labeled in terms of their recommendations or coaching protocols) are:

- No change
- Optimize low Carbohydrate (e.g., further decrease carbs, increase fat, decrease protein, initiate a fat fast)
- Transition to Paleo
- Transition to Paleo with intermittent fasting
- Get blood workup and medication assessment
- Remove artificial sweeteners
- Essentially classes may be any combination of a food plan and an accelerant. A class change may also involve changing a user goal. For example, an individual who is not losing weight may be told to decrease stress or improve sleep.

As one example of how machine learning may be used, a group of experts may initially classify a number of user records into a set of classifications that correspond to respective coaching protocols or recommendations. For example, a human expert may review the record (including ketone measurements, weight loss goals, demographic data, etc.) of a weight loss program participant and make a recommendation (representing an assigned class) regarding an action to take or protocol to follow. These expert-classified records may then be used to train the model 42 using an appropriate algorithm, such as a Neural Network, Support Vector Machine (SVM), Probabilistic Graphical Model (including Bayesian networks or Markov models), or Decision Tree model. Through a training process, various user attributes or "features" are computed from the user's data records and then the algorithm learns how much weight to give to each feature by analyzing the classifications given by human experts to existing user records. These learned weights become an integral component of a trained model 42, and are used to reproduce the behavior of human experts on unseen user records. Examples of features that can be used are listed in Table 5. As described below, the system 40 may also adaptively adjust the weights over time based on the results, including weight loss results, produced by the system's classifications and associated recommendations.

TABLE 5

Example features

User-specified goal
BMI (computed from height and weight)
Age (computed from date of birth)
Sex
Information from the daily log (e.g., based on Table 3)
Length of time on a particular diet
Weather (temperature outside)
Frequency of taking ketone tests
Frequency of completing user logs
Timing consistency of taking ketone tests (e.g., within tests within 10 minutes of each other each day versus seeing significant fluctuations >2 hours)
Taking "make up" tests after a bad score is achieved (e.g., a user who gets a 0 and then starts testing 2 times a day or a user who gets a "lower than average" score and immediately repeats the test)
Levels of a Primary Metabolic Analyte[1] (breath, blood or urine) reading at day t − 0
Levels of a Primary Metabolic Analyte (breath, blood or urine) reading at day t − 1
Levels of a Primary Metabolic Analyte (breath, blood or urine) reading at day t − 2
Average heart rate for past 3 days
Medications
Client's profile (e.g., Profile A, Profile B, etc.)
Evidence of insulin resistance from blood results or user's medications
Number of times user reported being hungry in last 7 days
Nutritional sophistication level

[1]This term is used as in U.S. application Ser. No. 62/528,200 entitled: "Automated Processes for Detecting and Addressing Health Issues Based on Monitored Analytes and Other User Data."

The foregoing features are merely examples. In some embodiments the number of features may, for example, be in the hundreds. The system 40 may use a data repository of feature definitions to calculate or otherwise determine features for a user based on the user's data record.

As shown in FIG. 1, the trained model 42 includes a feature extractor 46 that computes, extracts, or generates the features based on a user record and other parameters, for example a "target date." These features are then passed to a record classifier 48 that assigns the user record to one or more of the defined classes. The record classifier 48 may include sub-classifiers as is known in the art. The set of one or more classes is then used to select corresponding messaging, and/or a coaching protocol, to be used for automatically coaching the respective user. Although a user's data record may be large, not all of the data in the record is necessarily considered during classification. For example, through feature extraction, the system may effectively disregard measurements taken, e.g., more than two weeks ago.

In some cases, multiple distinct trained models may be used, such that the classification task is multilayered and nested. For example, some features may be used by one model to initially classify a user, and the results may be exposed as a feature to a "top-level" recommendations model. As another example, the system 40 may include different classifiers for different types of recommendations—for example, the system could include an "increase carbs" classifier and an "increase exercise" classifier, both of which operate as "yes or no" classifiers. As another example, the system could train and use separate models for males versus females, or for other demographic categories.

In some embodiments, the system 40 may include a supervised feedback loop in which computer-generated classifications are shown to human experts. The human experts can then indicate whether or not the trained model did the right thing. This data can be used by an iterative "training process" to continually improve the quality of the trained model in an online system. The system 40 could, for example, randomly ask an expert whether a prediction was correct.

The system could also assess the accuracy of its predictions without involving experts. For example, once the system classifies a user and provides a corresponding program recommendation, the system could track the user's progress over time, and could infer that the prediction/classification was inaccurate if the user fails to make progress (e.g., fails to lose weight).

In some embodiments, the system 40 may also use a machine learning process to automatically modify the class definitions, including the associated coaching recommendations, based on feedback. The feedback may include weight loss measurements reflective of the effectiveness levels of specific classifications and coaching protocols. Through this process, the system may learn, for example, that users whose ketone levels increase relatively slowly in response to carb reduction should be placed on a relatively strict carb reduction program for an extended time period.

In some embodiments the system 40 may assign a single class to a user record and associated parameters. In other embodiments, the system 40 may assign multiple classes. Some of these classes may map directly to recommendations while others may map to suggested options. For example, the system may classify a user and provide the recommendation that "no change is needed" while also providing the suggestion that they may "feel free to incorporate fruit in the diet."

Some of the defined classes may be persistent classes that are assigned permanently or for relatively long time periods. One example is the user/participant's nutritional sophistication level, which may be determined by having the user take an online survey. For relatively sophisticated users, the system may generate recommendations/messaging that includes more scientific terminology that for other users. For users with relatively low levels of nutritional sophistication, the system's output may include more pictures and less scientific terminology.

The system 40 may also use regression to identify or modify cut-off values used for classification. Here, there are at least two cut-off values that are worth discussing: (a) the values used for the determination of a user profile, such as those shown in the profiles depicted by FIGS. 9A through 9D; and (b) the values used for the computation of the "ketone level" points used in the generation of a Program Score. The aforementioned two cut-off values may also be interrelated.

Assuming the values are interrelated:

TABLE 6

| | User Goal: Lose Weight | | |
| --- | --- | --- | --- |
| | Low Carb | Paleo | FODMAP |
| Profile A | >=7 | 4 to 7 | <4 |
| Profile B | >=5 | 3 to 5 | <3 |

TABLE 6-continued

User Goal: Lose Weight

|  | Low Carb | Paleo | FODMAP |
| --- | --- | --- | --- |
| Profile C | >=5 | 3 to 5 | No 0s for 5 consecutive days |
| Profile D | >=3 | 1 to 2 | No 0s for 3 consecutive days |

The Profile computation, however, may also vary based on certain factors:

TABLE 7

|  | Ketone Threshold | Time Threshold |
| --- | --- | --- |
| Default | 4 ppm | 7 days |
| User who is traveling | 4 ppm | 10 days |
| User who has been low carb for >2 months | 4 ppm | 3 days |
| User who has already lost 20 pounds over the past 3 months and is in active weight loss | 4 ppm | 3 days |
| User who has very limited education | 4 ppm | 14 days |
| User who has financial limitations | 4 ppm | 14 days |
| User who is not able to participate in a low carb program and is thus on an alternate program | 2 ppm | 7 days |
| User who is beginning a weight loss program while on a long-term course of antibiotics | 2 ppm | 7 days |

Another way the system learns about the user is through score changes. For example, when the system recognizes a score change (increase or decrease) in excess of a variance threshold, the user may be prompted to explain the change. An example variance threshold is 3 ppm, which is outside normal physiological variance and also outside 2 sigmas of variance on precision characteristics of a given colorimetric sensor system. (These values may, of course, change depending on the performance characteristics of the sensor system and also the variance expected for a certain class of users).

Figure 20:
FIG. 20 illustrates an example screen display of the "coaching" feature of the mobile application of FIG. 17.

The system may request an explanation for these changes via the mobile application. FIG. 19 shows an example screen display in an embodiment of the mobile application, where the user is prompted to explain the increase in program score. The view includes an indication to the user that their level is higher than normal 1901, as well as a data entry function 1902 that allows the user to select an explanation for their change in program score. Alternatively, FIG. 20 shows an example screen display in an embodiment of the mobile application, where the user is required to explain the decrease in program score. The view includes an indication 2001 to the user that their level is lower than normal, as well as a data entry function 2002 that allows the user to select an explanation for their change in program score.

Another example of machine-based processes is determination of the reliability level of the user. The system is aware of which pieces of information are user-reported versus objectively determined. If there is a strong disconnect between user-reported information and objective information, the system may decrease the reliability level assigned to the user. For example, consider the following: for week 1 through week 3, the user had ketone levels (objective) of 10 ppm +/−2 ppm while on low carb with habit adherence (user-reported) of 100%. Then on week 4, the user reported breaking a habit in response to a score change (e.g., FIG. 20). From that point on, the user reported habit adherence of 100% but her ketone levels were always <5 ppm. The differential between 10 ppm and 5 ppm is far too significant for this to have been due to "recovery" from the cheat meal. Additionally, the time period of week 3 to week 5 is not sufficient for the user to have truly adapted. Thus, the user's reliability level would decrease. The system may compensate for this by changing the way the program score is computed (decreasing reliance on user-reported information) or by promoting use of third party objective tools, e.g., a wireless bathroom scale and financial information to look for evidence of "cheating" at restaurants.

Algorithmic Efficiency and Computing Benefits

In a typical diet journal, the user records 7 items per meal per day, 3 snacks, and 3 non-water beverages. So, over the course of the day, the user would have logged 27 pieces of user input data. Each user input data point is associated with macronutrient value (minimally protein, fat, and carbohydrates), and therefore there would be a minimum of 81 data points. This data is then transformed into total grams of carbohydrates. Then, the user would need to provide information regarding workouts, which would mean that significant heart rate data would be input into the system. Being conservative, for a given day, approximately 100 data points would be logged by each user.

When the user is logging parseable pieces of data, not only is this helpful to the user to directly associate his or her behavior with instructions that are program-specific, but the average program has 5 to 10 elements—which would include more complex information than just the protein/fat/carb breakdown (potentially including, for example, whether or not the user consumed nightshades or nuts) as well as information on accelerants.

This 10-20× decrease in data is not only more computationally efficient, but it also lends itself to substantially less user error and thus improved data integrity.

As one layer atop the data, the Program Score is computed. The Program Score may be used independent of other data for purposes of determining if a user is at risk for boredom or physiological adaptation. This may reduce the data from existing practices (100 data points per day versus 1 data point per day).

As an example, User A has been placed on a program with a Goal of Weight Loss, a Food Plan of Low-Carbohydrate (<50 g), an Accelerator of Exercise, and an Accelerant of Reduced Alcohol Consumption. User A collects food intake and exercise data while on the program. Table 8 displays the total amount of food intake data collected by conventional applications over the course of two days. All of the gathered information makes up 96 data points, counting three data points for each food recorded (protein, fat, carb). Table 9 displays heart rate data collected over two separate workout sessions. The user's heart rate is recorded every 5 minutes, over two sessions, for a total of 24 points. By using conventional methods, the system has to record and process a total of 120 data points to make an assessment about the user. It should be noted that this data does not account for other program behavior adherence, such as the user's ability to refrain from alcoholic drinks. It should also be noted that the data does not indicate to the user which components of the data points are significant to the user.

Table 10 displays the total amount of information necessary for the proposed system embodiment to make an assessment of the user's progress. This involves asking User A specific questions that pertain to the user's overall program. The same data that is collected in Tables 8 and 9 is condensed into fourteen (14) data points in Table 10 for the user to input.

TABLE 8

Food Intake Data Entry-Conventional

| Macronutrient | Carb (g) | Fat (g) | Protein (g) |
|---|---|---|---|
| Day 1-Breakfast | | | |
| 1 egg | 0 | 5 | 6 |
| Onions, Chopped, ¼ cup | 0 | 0 | 3 |
| Grapefruit, Medium, ½ | 1 | 0 | 8 |
| Spinach, ½ cup | 1 | 0 | 1 |
| Tea, 8 oz | 0 | 0 | 0 |
| Half and Half, 4 tbsp | 0 | 4 | 0 |
| Agave Syrup, 2 tbsp | 32 | 0 | 0 |
| Day 1-Lunch | | | |
| Coke Zero, 12 oz | 0 | 0 | 0 |
| Cheese, Cheddar, 2 slices | 1 | 19 | 13 |
| Lettuce, raw, 1 cup | 1 | 0 | 0 |
| Grilled Burger Patty, 1 | 0 | 20 | 15 |
| Ranch Dressing, 2 tbsp | 1 | 19 | 0 |
| Bacon, 2 Slices | 1 | 7 | 5 |
| Day 1-Dinner | | | |
| Cheese, Parmesan, Shredded, ½ cup | 1 | 11 | 15 |
| Broccoli, Cooked, 1 cup | 6 | 0 | 3 |
| Salmon, 1 portion | 0 | 20 | 37 |
| Water, 4 cups | 0 | 0 | 0 |
| Day 1-Total | 45 | 105 | 106 |
| Day 2- Breakfast | | | |
| Spinach, ½ cup | 1 | 0 | 1 |
| Mushrooms, White, ½ cup | 1 | 0 | 1 |
| Sausage, 2 links | 1 | 9 | 7 |
| Egg White Omelet, 3 Egg Whites | 1 | 0 | 11 |
| Mozzerella Cheese Stick, 2 oz | 0 | 10 | 16 |
| Tea, 8 oz | 0 | 0 | 0 |
| Half and Half, 4 tbsp | 0 | 4 | 0 |
| Splenda, 3 pkg | 3 | 0 | 0 |
| Day 2-Lunch | | | |
| Caesar Salad, 1 plate | 10 | 14 | 5 |
| Salmon Burger, 1 patty | 2 | 9 | 20 |
| Day 2-Dinner | | | |
| Carne Asada, Grilled, 8 oz | 0 | 27 | 29 |
| Shrimp, Grilled, 10 | 1 | 2 | 15 |
| Spinach, Cooked, 2 cups | 3 | 0 | 2 |
| Coke Zero, 12 oz | 0 | 0 | 0 |
| Day 2-Total | 23 | 75 | 107 |

TABLE 9

Exercise Data Entry-Conventional

| | Time (min) | Heart Rate (BPM) |
|---|---|---|
| Day 1 | 0 | 87 |
| | 5 | 91 |
| | 10 | 108 |
| | 15 | 111 |
| | 20 | 120 |
| | 25 | 122 |
| | 30 | 126 |
| | 35 | 135 |
| | 40 | 128 |
| | 45 | 117 |
| | 50 | 89 |
| | 55 | 75 |
| | 60 | 78 |
| Day 2 | 0 | 84 |
| | 5 | 84 |
| | 10 | 83 |
| | 15 | 99 |
| | 20 | 113 |
| | 25 | 118 |
| | 30 | 124 |
| | 35 | 123 |
| | 40 | 131 |
| | 45 | 127 |
| | 50 | 108 |
| | 55 | 92 |
| | 60 | 87 |

TABLE 10

Proposed Program Data Entry

| Habit Question | Possible Values | Input Value |
|---|---|---|
| Day 1 Carb Count (g) | <20 g, 20-30 g, 30 g+ | 30 g+ |
| Packets of Artificial Sugar | 0, 1-2, 3+ | 0 |
| Any Cheat Meals? | Bad Day, Bad Meal, Nope! | Nope! |
| Workout-CV-Duration (m) | None, 16-30, 30-60 | 30-60 |
| Workout-Strength-Duration (m) | None, 16-30, 30-60 | 30-60 |
| Total Alcoholic Drinks-Wine | None, 1-2, 3+ | None |
| Total Alcoholic Drinks-Hard Liquor | None, 1-2, 3+ | None |
| Day 2 Carb Count (g) | <20 g, 20-30 g, 30 g+ | 20-30 g |
| Packets of Artificial Sugar | 0, 1-2, 3+ | 3+ |
| Any Cheat Meals? | Bad Day, Bad Meal, Nope! | Nope! |
| Workout-CV-Duration (m) | None, 16-30, 30-60 | 30-60 |
| Workout-Strength-Duration (m) | None, 16-30, 30-60 | None |
| Total Alcoholic Drinks-Wine | None, 1-2, 3+ | None |
| Total Alcoholic Drinks-Hard Liquor | None, 1-2, 3+ | None |

The system is able to generate algorithmic assumptions from the user's data, and the user is able to identify which program habits are the most significant. As an example, User B is on a program that utilizes a Paleo food plan, and does not possess prior knowledge on the food plan. User B may input dozens of data points regarding their food intake using a conventional data entry method. Under conventional methods, the user is not able to draw connections to their food intake and program adherence. Using the data entry system disclosed herein, the system does not require the user to log each meal and snack item; rather, the system asks the user specific questions that pertain to the food plan, such as "Did you consume any refined sugars?" or "Did you consume any preservatives?" The user is then able to identify the key features of the food plan, without inputting additional information that would seem superfluous to the user.

Wellness "GPS" or Wellness Navigation System

In the United States today, there are some 108 million individuals seeking to diet or lose weight. This number gets larger each year and, at the same time, the incidence of obesity continues to grow. The prevalence of obesity has resulted in a constellation of co-morbidities from cardiovascular disease to hypertension to cancer to mental health challenges like depression and Alzheimer's disease. For many people, the desire to "get healthier" is there but the trek ahead is arduous and seemingly unattainable. To make matters worse, our health data is notoriously historical. The current convention is to information people about their present weight, their past incidence of disease, etc. The ability to provide forward-looking projections is not possible.

The systems and methods described herein and in the disclosures incorporated by reference enable a forward-thinking projection, which the inventors refer to as a Health GPS System or a Wellness Navigation System. In effect, taking a user's initial conditions, and profiling users, using for example the machine-based processes described herein, we predict how the user may achieve his or her goals. The visualization is not only in the form of recommendations, but is also in the form of a path: visually showing the user how he or she can achieve lofty goals, e.g., losing 100+ pounds of weight, regressing glucose levels >200 mg/dL to 80 to 100 mg/dL, improving sleep. If the user stops monitoring his or her ketone (or other metabolic) levels, the system tells the user that he or she needs to "recalibrate" (akin to a GPS system telling a user to get back on a known path). If the user begins to take a different path, e.g., switching from low carb to Paleo and juice cleanses on her own, the system re-routes to allow the user to still achieve his or her goal using this alternate path.

Essentially, the convention of food plans and accelerants, as described herein, forms the basis for a "road system" much like current roads and expressways. Over time, we fully expect the list of food plans and accelerants to grow as science and nutrition evolve. Like with roads, the system described herein will learn new food plans and accelerants. But just as important, determining where the user is on his or her journey is also important—hence the need for data, whether objective or user-reported. The value of objective data is that it is reliable and will become habit forming, thus increasing the amount of data available to the system.

Adaptation

The applicant has observed that certain users begin to "adapt" to a program after a certain period of time. This adaptation has been associated with a decrease in ketone levels. The applicant has also observed that a change in the program results in an increase in ketone levels.

For this reason, the system optionally includes recommendations to change the user's program before the user adapts. This recommendation system is also useful to prevent the user from simply getting bored and thus seeing decreased compliance.

The triggers for a program change may vary. For example, the system may prompt the user to accept a program change or may simply change the program itself due to:
  The numbers of days that a user has been on a given program (e.g., prompt the user every 4 weeks)
  A slow and sustained decrease in ketone levels while on this same program
  Frequent changes in ketone levels (e.g., multiple instances of +/−3 ppm changes within a given week)
  Progressive decreased adherence to the habits The system may also recommend a program change for reasons other than adaptation or boredom, such as lack of effectiveness. In this scenario, the system may prompt the user to accept a program change or may simply change the program itself due to:
  The number of days that a user has had a "good" Program Score on a given program ("good" may be >80, in the example shown above)
  A change in the user's average Program Score on the current program as compared to a prior program (e.g., user had a historical avg. Program Score of 85 on program 1 and now has an avg. Program Score of 30 on program 2).

Figure 21:
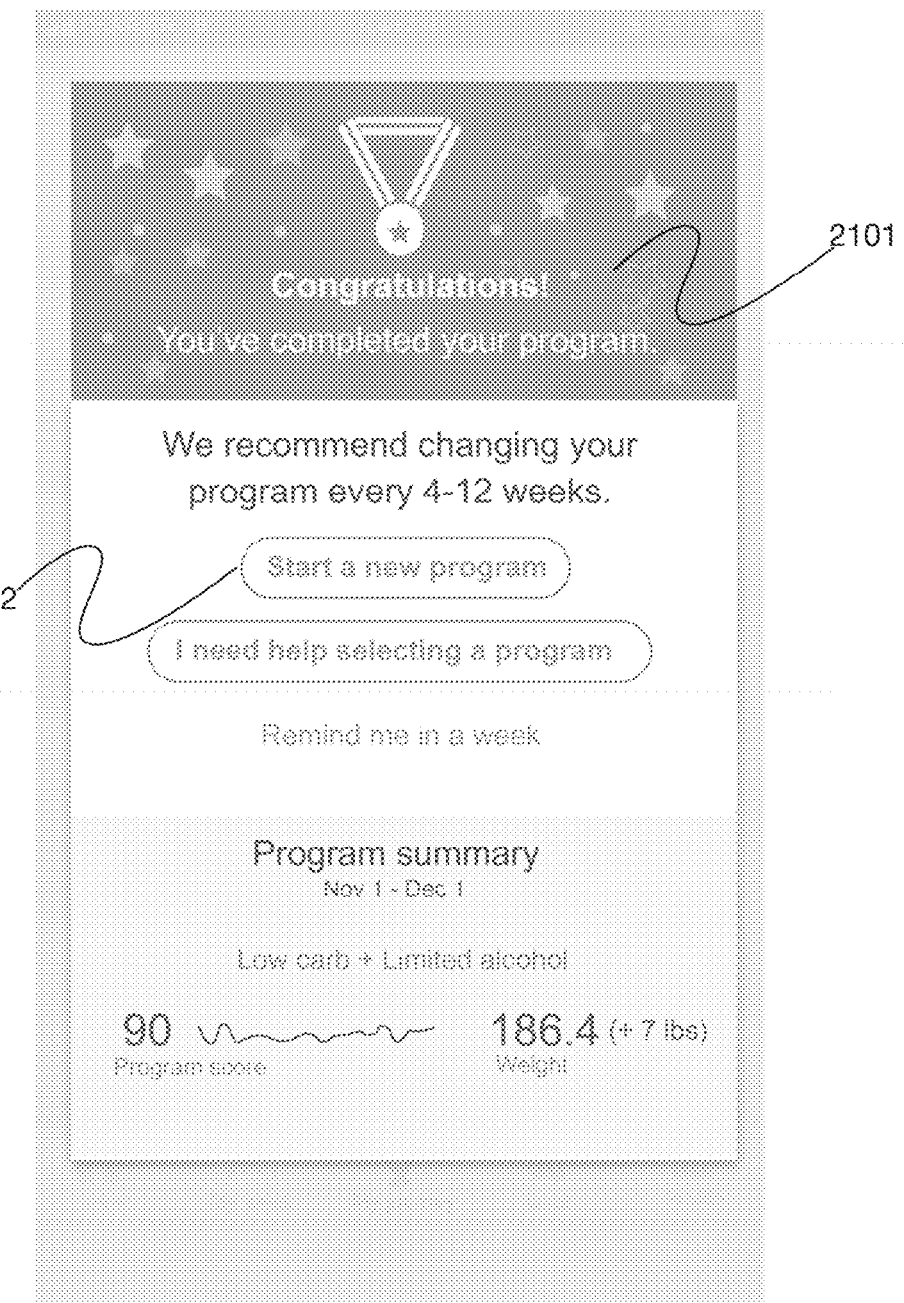
FIG. 21 illustrates an example screen display of the "coaching" feature of the mobile application of FIG. 17.
Figure 22:
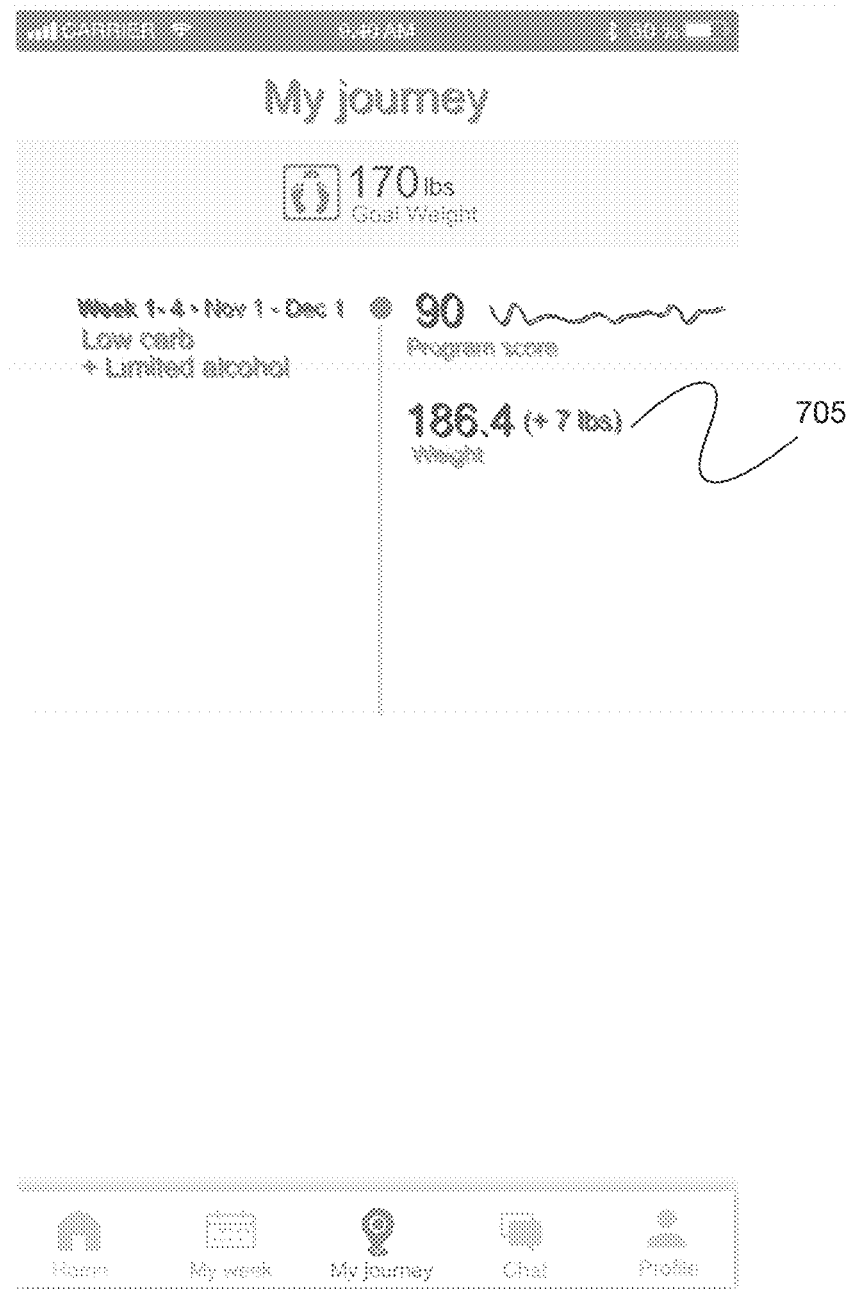
FIG. 22 illustrates an example screen display of the "my journey" page of the mobile application of FIG. 7.
Figure 23:
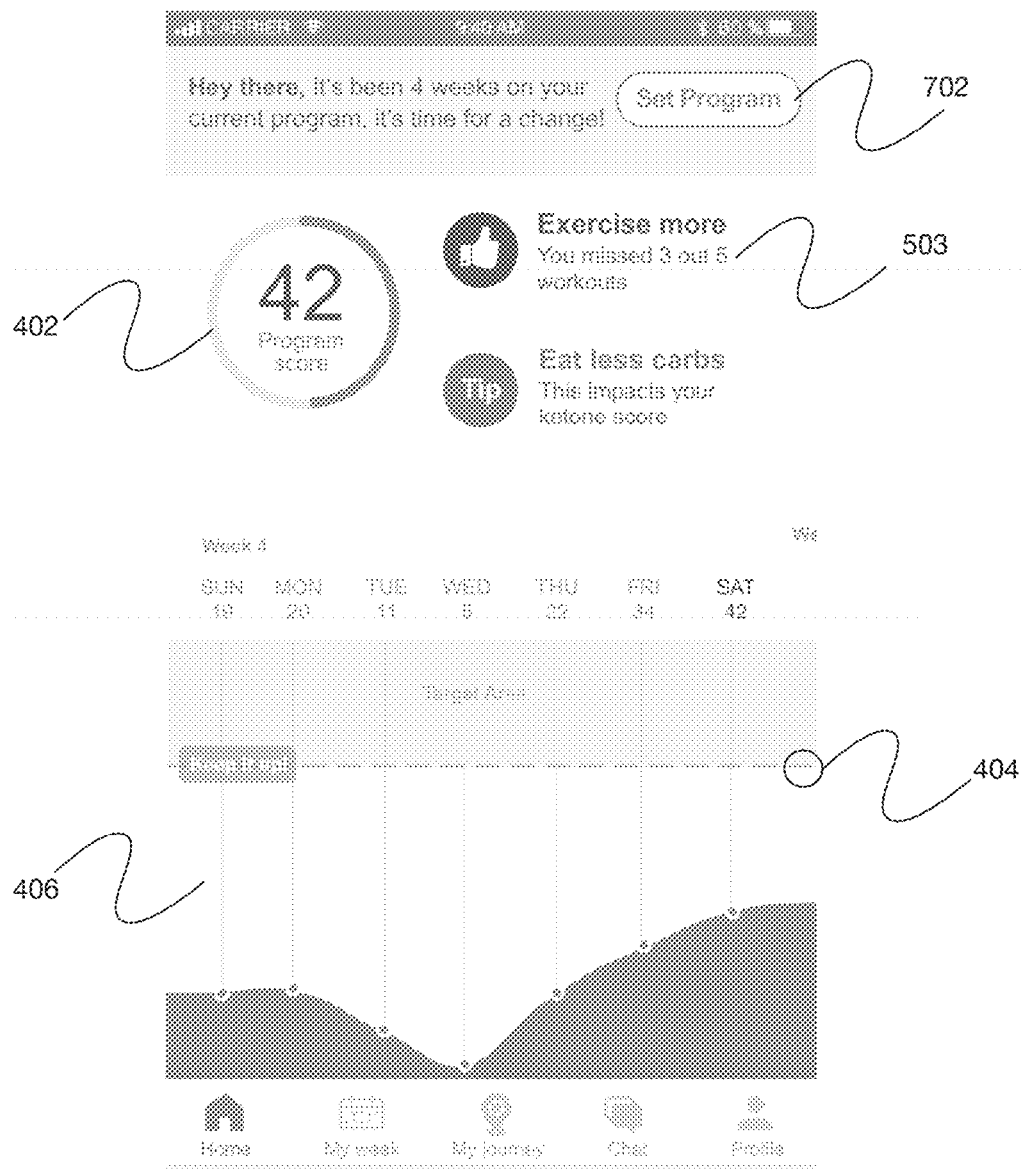
FIG. 23 illustrates an example screen display of the home page of the mobile application of FIG. 4.
Figure 24:
FIG. 24 illustrates an example screen display of the "my journey" page of the mobile application of FIG. 7.

FIG. 22 illustrates an example screen of the "my journey" feature, where the user's progress in one phase of their program is shown in an indicator, such as the indicator for the user's weight 705. FIG. 24 also illustrates an example screen of the "my journey" section of the mobile application, where the user's progress through multiple phases of the program is summarized by an indicator 2401. The user may review this information and determine on their own that a change in program is needed. In other embodiments, the system's recommendations are explicitly indicated within the mobile application. FIGS. 7, 21, and 23 all illustrate example screen displays that include an indication 502 for the user to change their program.

The system may also recommend program changes for the user in the form of program breaks. The system may intake data from a third party application, like the user's calendar application in their smart phone. The system may recognize events or holidays that are significant to the user, and suggest that the user take a break from the program, and resume their program after that time. FIG. 24 shows an example screen display of the "my journey" section of the mobile application, which includes an indicator 2402 for the user to plan a break within the mobile application.

Predicting when a user needs to "take a break" is desirable for a few reasons: (1) obtaining data that shows non-compliance can be highly discouraging for a user—it is better for the user to know he or she can take some time off than to believe that he or she is "failing"; (2) sometimes the act of taking a break actually helps to boost metabolism if the user makes good choices during this time; and (3) the system gets better information and learns a user in a better way if the data is represented correctly—e.g., if "vacation" data is separated from "non-vacation" data and so on.

Coaching Interface

The System may involve human coaching, coaching via machine-based processes, or a combination thereof. Certain elements of the coaching interface are now described.

Figure 18:
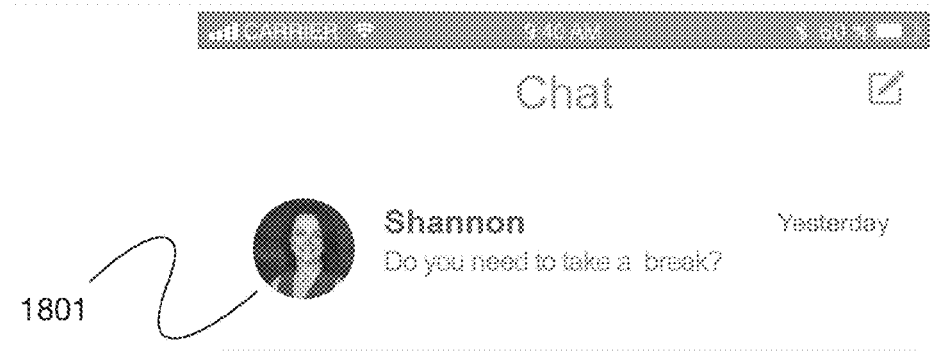
FIG. 18 illustrates an example screen display of one embodiment of a mobile application's "chatroom" page.

The coaching interface may be on a mobile application, in browser form or using some other medium. The coach and client (user) may communicate in many ways, such as via free form chat, e.g., FIG. 18, by guided questions or standard phone/text. Guided questions may be: (a) help me understand why my score increased or decreased, (b) help me understand why I'm not achieving my goal, (c) I need suggestions on what to eat, and (d) I feel like I'm failing and need support. The value of guided questions is that it decentralizes the communication from a 1:1 ratio between the coach and client to a broader audience. For example, guided question (c) may be directed to a subject matter expert on the particular food plan that the client is on, whereas guided question (d) may be directed to a psychology expert with little to no nutrition background. Guided questions also facilitate use of machine learning to answer questions that lend themselves to responses that do not warrant or require a human.

Table 11 shows an example set of criteria to separate successful, at-risk, and "failing" clients. This set of criteria may be learned and improved as additional data is collected. However, the representation of clients in a triaged fashion breaks the modern convention of coaching by appointment and opens the doors for coaching by need.

"Coaching by need" basically means that a coach may start off his or her day by reaching out (via text, phone, chat or other means) to the "at risk" clients first, then reward the "successful" clients and then figure out what is going on with the "failing" clients. Or, if the number of "failing" clients increases, this is a strong indicator that a second coach is needed or the coach needs re-training.

Even if appointments are used, it greatly simplifies the coaching interaction if a coach walks into an appointment with a client and, instead of spending the first 5 minutes reviewing data, knows the client's status and is now focused on helping the client achieve the next level of success. For example, if a typical primary care physician has appointments every 10-15 minutes, he or she spends the first 33% of the appointment assessing what is going on. That time could be better spent with indicators to tell the physician: "this client is doing very well—focus on rewarding the client and potentially save some extra time for your "red"/"failing" client who is scheduled for 10:30 am."

Extra Credit and Leniency

As the system learns the user, the system may create "extra credit" opportunities for the client, "redemption" opportunities for the client, and may suggest leniency. These features further customize the program to a client.

Leniency is used when learning that the user does not require the same level of adherence to a particular food plan in order to achieve results as compared to other users. For example, a low carbohydrate diet is set at a baseline of <20 g total carbs. If a user is achieving success, the system may change the rules to <30 g total carbs. If the user is continuing to achieve success, the system may further change the rules to <50 g total carbs. The system may also change the rules to <40 g net carbs. These changes still keep the user in the boundaries of low carb and the user is still seeing results, but now the system knows that the user can still see results with a slightly less demanding regimen. Another example may be dairy exclusion: for some users, dairy may need to be permanently eliminated. But for others, maybe 1λ per week is okay. For others, it may be 3× per week, but not every day.

An "extra credit" opportunity is created when the system recognizes that the user achieves a higher level of success (e.g., higher ketone levels or decreased negative symptoms) in response to a particular element of a food plan or accelerant. The classic example may be: your ketone levels increase in response to working out with a HR>130 bpm. If the user's program calls for the user to do this 3× per week to achieve a certain goal, and the user does this 5× in a particular week, this may result in the creation of "extra credit" points.

If the system now learns that certain behaviors result in an increase in negative symptoms or decreased ketone levels, e.g., consumption of a cheat meal, this may be an opportunity for "redemption". Thus the user may redeem "extra credit" points without negatively impacting his or her Program Score.

Triaged Friends List

The system in some embodiments utilizes a social networking feature that allows the user to interact with individuals on other programs, and create a social support group. The purpose of this feature is to allow the user to have other users as additional tools for program success. The system allows the user to view their list of friends, and also allows the user to see his or her performance compared to his/her friends. The user may also challenge his or her friends for short periods of time to improve self-performance, as well as recruit certain friends for help if they encounter personal obstacles during their program.

Presently, many if not most social Apps simply display a user's friends. By using the methods described herein, the information that is important for a user to see vis a vis his or her friends is made more prominent. This type of interface is designed to facilitate meaningful communication (based on the triage status of a friend), responsive to what a friend needs (based on specific help requests), and considering the specific program that a friend is on (based on the display of food plan and accelerants applicable to that particular friend).

Interestingly, the information visible to the friend may or may not include weight, even for a goal of losing weight. Instead, the Program Score (as described in the above example) may simply contain other pieces of information. Or the raw ketone level may be displayed. This is advantageous as it is arguably less embarrassing to the user.

In certain embodiments, the friends are triaged, or sorted based on different aspects of their program performance. The order or manner in which friends are triaged may be depicted by a "color" assigned to the friend, e.g., "red", "yellow", or green. Examples of ways to categorize users are shown in Table 11 below:

TABLE 11

| User Friend Triaging | | |
| --- | --- | --- |
| Green (Successful Friend) | Yellow (At-Risk Friend) | Red (Unsuccessful Friend |
| Performs a breath test >= 85% of the days Ketone levels >= 2, 85% of the time Habits >= 60% Losing or maintaining weight | Skips a breath test for >= 3 days Ketone level of 0 for 2 days Skips logging or changes the response to habits >= 3 days Sustained decreased score >= 2 ppm comparing the past 7 days average to the past average (day 8 to day 14) Misses a weight login for 2+ Week Types in the same weight for 2 weeks without a decimal point | Gained weight Sustained ketone level of 0 for 3+ days Has not tested > 14 days |

The aforementioned triaging may preferably also be visible to a coach or trainer. The triaging characteristics may be different in that situation. The system is able to use information about the user's support structure to increase the likelihood of success for the user. For example, if Friend 1 and Friend 5 are both on a low carb food plan but Friend 1 is getting high ketone levels and Friend 5 is not, but Friend 1 is on an exercise accelerant and Friend 5 is not, the system may encourage Friend 5 to join Friend 1 to work out.

As another example, if Friend 1 has a goal of lose weight but Friends 2, 3, 4, and 5 just changed to maintain weight, the system may assume that all friends are going on vacation, and ask Friend 1 if he or she wants to switch the program goal.

As another example, if Friend 1 has had historical success with alcohol removal, but selected a plan that does not use alcohol removal as an accelerant (and instead picked dairy removal), but Friend 4 is on an alcohol removal, and Friend 1's progress is slow compared to his own historical data, the system may encourage Friend 1 and Friend 4 to pursue alcohol exclusion together.

Figure 30:
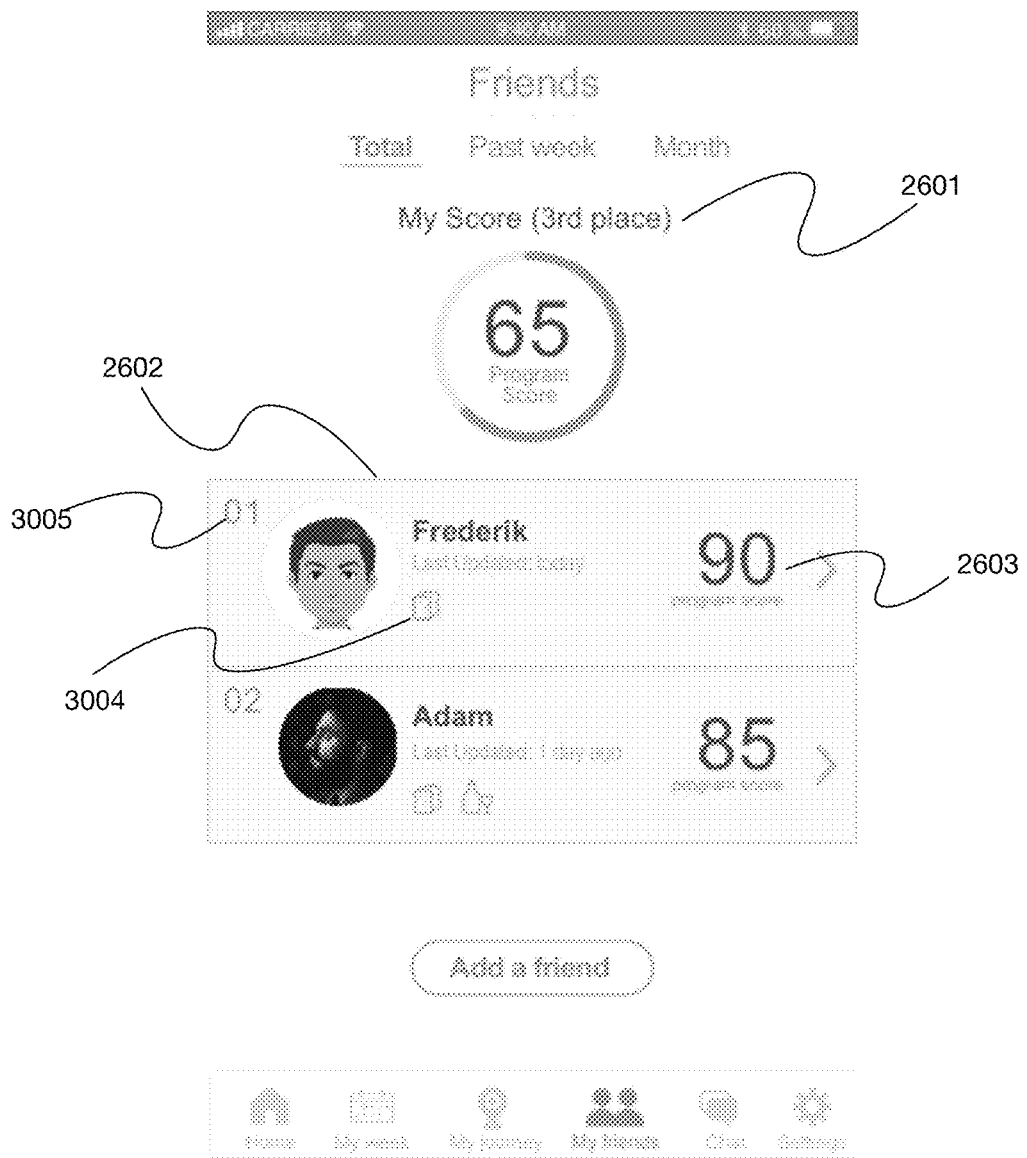
FIG. 30 illustrates an example screen display of the "scoreboard" page of the mobile application of FIG. 25.

To avoid encouraging herd mentality (when clearly personalization is key), the information displayed on the Friends Page may include an icon that represents: "On my food plan" or "On my accelerant". In this way, it helps people realize that some users are on a different program and thus, the tips that are helpful to one user may not be helpful to another. FIG. 30 shows that certain friends have a designator that they are on the same food plan 3004.

While the user can have an unlimited number of friends in his or her general social network, he or she may need to pick only a certain number of friends (e.g., 3 to 5) that are going to offer legitimate support, which are known as "helper friends." These helper friends can be utilized by the user in the system's help feature, which allows the user to identify individuals that they feel can maintain the responsibility of holding the user accountable during certain events or obstacles that the user may encounter. The user utilizes help requests within the mobile application, that allow the user to ask a designated "helper friend" to support them for an obstacle. These "helper friends," in turn, maintain the responsibility of providing helpful "nudges" or messages to the friend via the mobile application at various points during the program. In this regard, the system promotes specific types of "help" that is program-specific, as well as specific "nudges" that may correspond to the user's requests. Examples of these requests and nudges are described in Table 12 below:

TABLE 12

| Possible User "Help Requests" | Possible Helper Friend "Nudges" |
| --- | --- |
| Help me at the gym | Hey, you haven't logged today! |
| Help me at the party | Noticed you broke a habit today☺ |
| Help me at lunch | Way to go! So proud of you! |
| Help me on this trip | Want to meet for 15 minutes? |
| Help me at this meeting | Don't forget to skip the sweetener! |
| Send me a meal idea! | Here's a link to the restaurant, |
| Help me feel that I'm not a failure☹ | menu, try the _____. |
| Help me get motivated | |
| I need a buddy. | |

As an example, a user may request support from a helper friend because they are attending an upcoming party, and the user would like to refrain from alcohol consumption. The user sends a help request to their helper friend, who will utilize nudges during the party to motivate the user to refrain from alcohol. The helper friend sends nudges that say "Just a few more hours!" or "Try a club soda with lemon juice."

In some embodiments of the system, the user is only allowed to pick a certain number of helper friends. In some embodiments of the system, the helper friends are not made aware that they have been given that responsibility until they are issued a help request. In some embodiments, when the user sends a help request, it is sent to their entire helper friend list, however, in other embodiments the user is able to send help requests to individual helper friends.

The user can adjust their "helper friend" list in response to the needs of other users. As an example, User X has User Y and User Z listed as helper friends. User X knows that User Y is getting married, and may not be able to maintain helper friend responsibilities. User X chooses to remove User Y as a helper friend for a period of time, and then add User Y back at a later date. User X also knows that User Z is near the end of her pregnancy, and opts to switch User Z out for another helper friend for the time being.

Alternatively, the system can also recognize patterns among a user's helper friends, and determine if certain helper friends should be removed, in response to failing to adhere to a user's help requests. The system possesses a set of rules that dictate the tasks that a helper friend should be completing. If the system recognizes that certain helper friends are not completing those tasks, the system can remove the helper friend altogether. Moreover, the system may suggest a new helper friend to the user for some period of time. As an example, User C has User D listed as a helper friend. The system recognizes that for the last 5 help requests issued from User C, User D has not acted on or supported User C in any way. The system suggests to User C that because User D is not following through on helper friend responsibilities, User C should consider recruiting a new helper friend. The system indicates to User D that they have been temporarily disqualified from User's C helper friend list for a period of 30 days.

Figure 25:
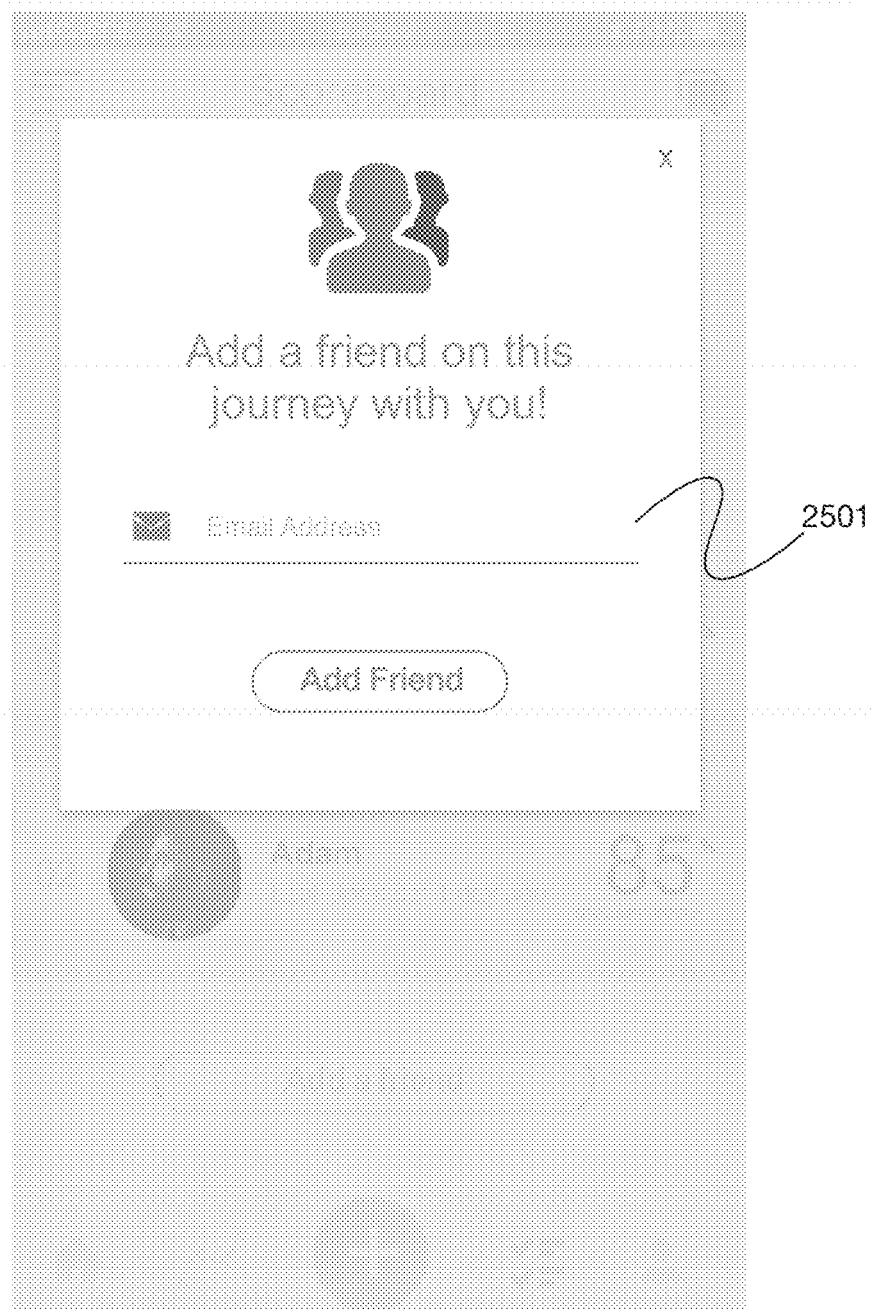
FIG. 25 illustrates an example screen display of one embodiment of a mobile application's "scoreboard" page.
Figure 26:
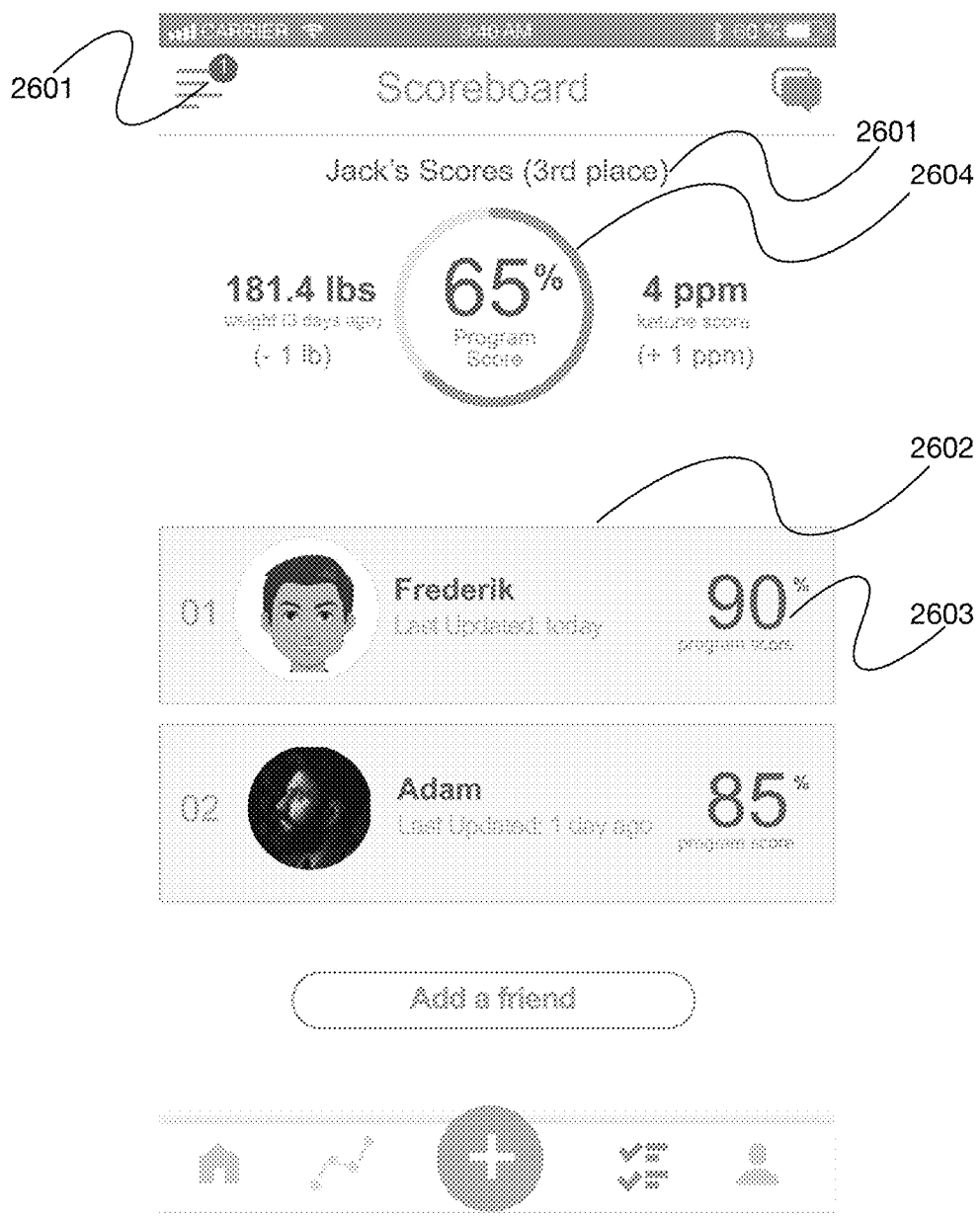
FIG. 26 illustrates an example screen display of the "scoreboard" page of the mobile application of FIG. 25.
Figure 27:
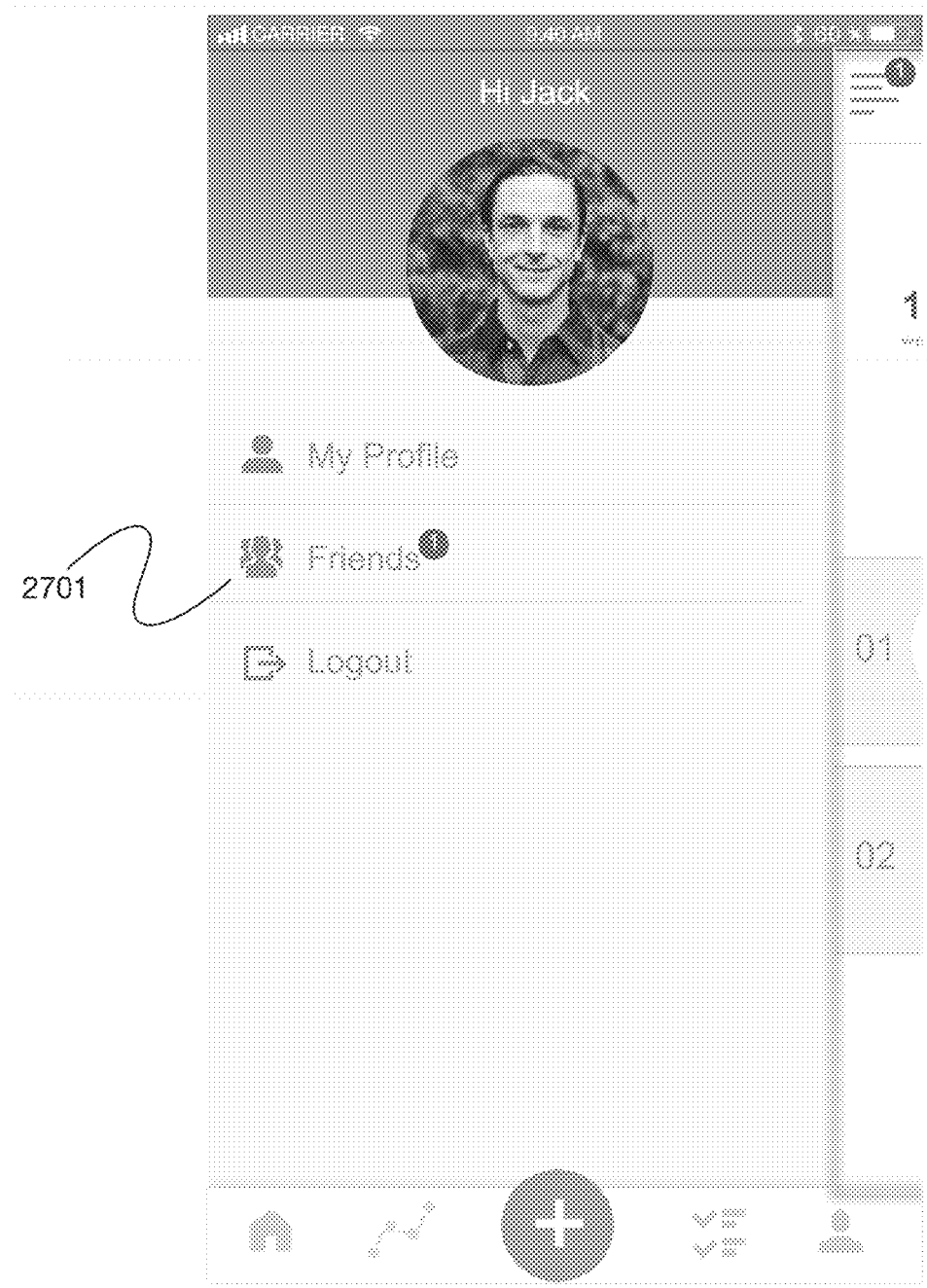
FIG. 27 illustrates an example screen display of the "scoreboard" page of the mobile application of FIG. 25.
Figure 28:
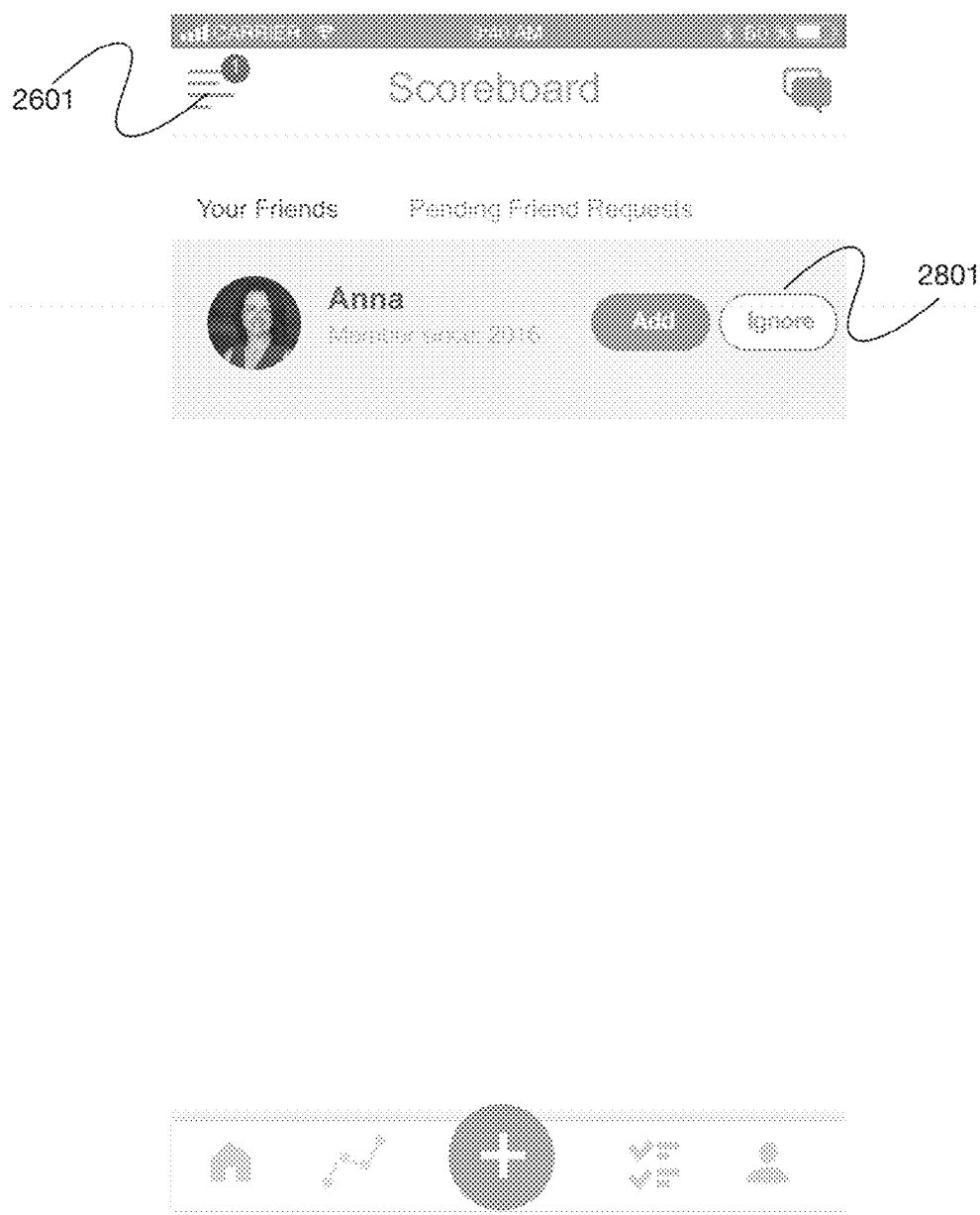
FIG. 28 illustrates an example screen display of the "scoreboard" page of the mobile application of FIG. 25.

The user's relationship with their triaged friends is preferably embodied in the mobile application. At the start of the user's program, the user is asked to create a group of friends by inviting them to pursue a program with them. FIG. 25 illustrates an example screen display in an embodiment of the mobile application, where the view includes a data entry function 2501 for the user to provide email addresses of other friends to join the program with them. In addition to adding friends to their friends' list, the user may also be invited to join other social groups via another user. FIG. 26 illustrates an example screen display of the "scoreboard" page of the mobile application of FIG. 25. This view includes an indicator 2601 that the user has a "friend request" from another user. FIG. 27 illustrates an example screen display of the same embodiment, where the user is now directed to their profile to see the "friend request." This view also includes an indicator 2701 that the user has a "friend request" from another user. FIG. 28 illustrates an example screen display of the same embodiment, where the user is now viewing the "friend request." The user can utilize a selection button 2801, and choose to accept another user's friend request.

Figure 29:
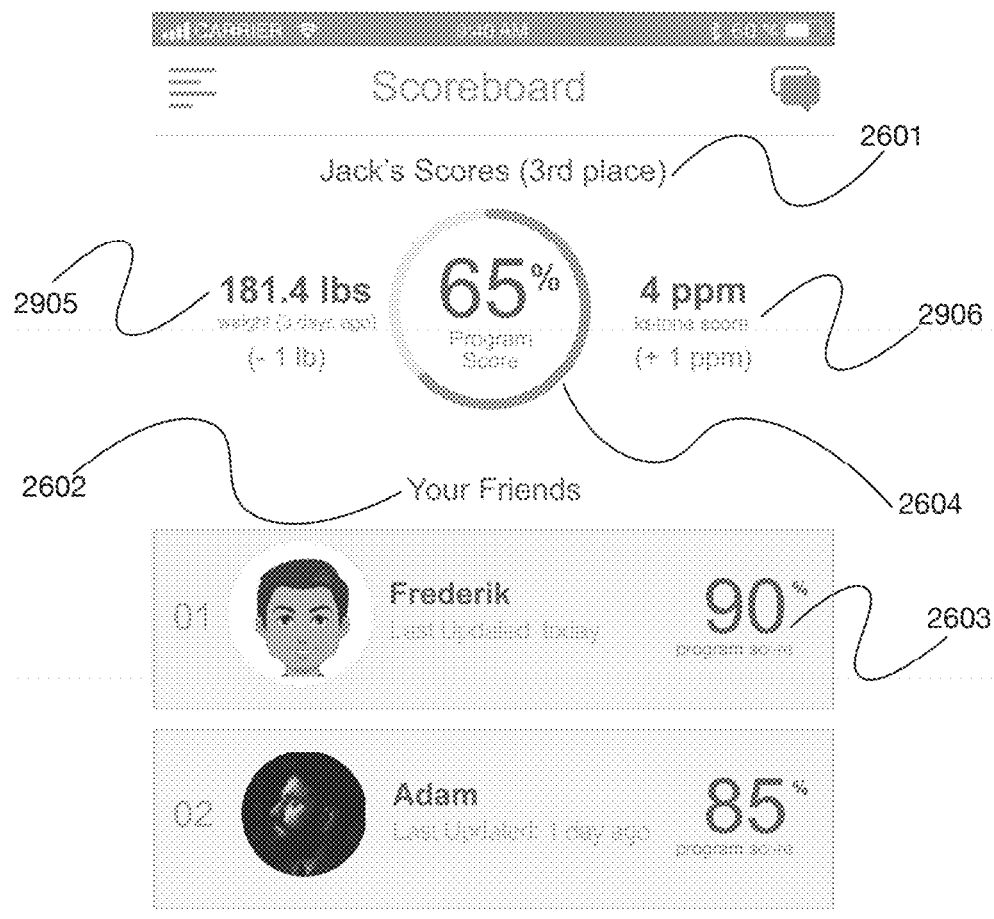
FIG. 29 illustrates an example screen display of the "scoreboard" page of the mobile application of FIG. 25.
Figure 31:
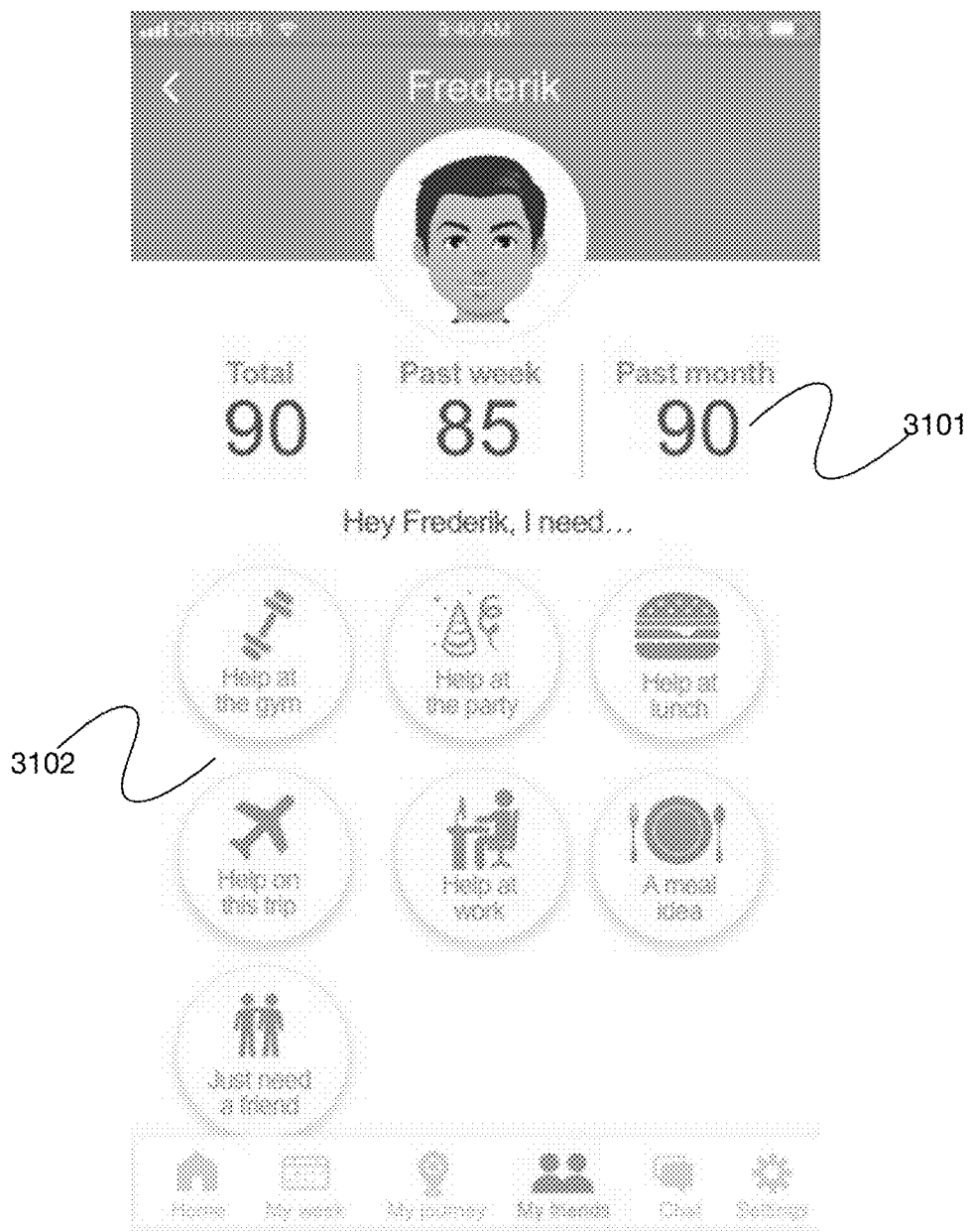
FIG. 31 illustrates an example screen display of the "scoreboard" page of the mobile application of FIG. 25.

After the user's friend's group has been developed, the user may compare their program progress to the progress of friends using a "Scoreboard" feature within the mobile application. FIG. 29 illustrates an example screen display of a "Scoreboard" feature in an embodiment of the mobile application. This view includes an indication 2601 of the user's progress as ranked against other friends. The view also includes an indication 2602 of the user's list of friends, an indication of the user's program score 2604, as well as an indication 2603 of the user's friend's program scores. This view also includes an indication 2905 of the user's weight, and an indication 2906 of the user's ketone score. The user's weight and ketone score may be included depending on the program. In other embodiments, the user's weight may be embarrassing for the user to disclose, and is eliminated, as illustrated in FIG. 30. The user can review the program scores of other users to determine if a fellow user or friend can aid them in their program. FIG. 31 illustrates an example screen display of an embodiment of the mobile application. This view includes a summary of the user's friend's program scores 3101, as well as an indication 3102 for the user to request help from the friend for a particular event or circumstance. Referring to FIG. 31, as an example, a user may see that their friend, Frederik, is keeping their program scores consistently high for the last month.

The user may also have access to subsets of information about other friends within their social group, such as specific elements of their program. This information may be present within the "scoreboard" feature of the mobile application. The user may utilize this information to associate the progress of different users with certain program elements. For example, referring to FIG. 30, the user may see their friends organized based on a ranking indicator 3005. The user may recognize that certain friends, in this case Frederik and Adam, possess significantly higher program scores 2603. The user may also recognize that both friends are using particular accelerants, displayed by an accelerant indicator 3004. The user may then conclude that those accelerants may be contributing to their increased program score, and may be inclined to add those accelerants to their program.

Example 1

The user, Margaret, begins using the system with a user goal of losing weight. Margaret gained a significant amount of weight after having children, and at a starting weight of 240 lbs, would like to lose 60-70 lbs total. Table 13 below indicates the changes that the system has made to Margaret's program over the course of 10 weeks, while Table 14 below indicates the changes the system has made to Margaret's program score computation.

Referring to Weeks 1 and 2 of Table 13, the system records Margaret's baseline levels for a period of 14 days. The system's baseline data indicates that she has reached a 5 ppm reading within a week, so the system places her into a "Profile A" metabolism category. The system uses the mobile application and coach aid to help Margaret build her program. As shown in Week 3 of Table 13, the user inputs a goal of "losing weight," a food plan of "low carbohydrate (<20 g)," an accelerant of "no alcohol," and also inputs that she would like to monitor her own weight. The system recognizes that over the first three weeks, the user has reported weight loss at a steady rate. The system, after recognizing this pattern over three weeks, determines that this program is working for the user, and classifies Margaret's current program as "effective."

After 4 weeks, the user inputs that her weight is now down to 230 lbs. The system recognizes a pattern of decreased engagement in the program, in this case indicated by lowered adherence to the daily testing and data entry that is evident in Week 5 and 6 of Table 14. The system, after recognizing this pattern for a week of testing, determines that this program is no longer working for the user, and classifies Margaret as "losing engagement."

The system establishes a relationship between the user's irregular testing, and the user's achievement of weight loss. The system recognizes that whenever Margaret performs a test, her ketone levels are significantly lower than what was seen in the first few weeks of the program. The system concludes from the data that the user is suffering from sporadic cheating. Referring to Week 6 of Table 13, the conclusion prompts the system to suggest to Margaret to change her accelerant to "Controlled Cheat Meals" via the Mobile Application. The system also prompts Margaret that her program score computation should be modified to place more weight on breath test adherence, as opposed to breath ketone test results. This change is noted in Week 4 of Table 14, as the weight for breath test adherence increases from 30% to 40%.

The user continues the program with one cheat day a week, and over the next month, her weight drops down to 215 lbs. The system determines that this program is working for the user, and classifies Margaret's current program as "effective." The system also prompts Margaret that her program computation should be modified to place more weight on habit adherence, as opposed to test results. This change is noted in Week 6 of Table 14, as the weight for habit adherence increases from 30% to 40%. At the same time, the system recognizes that the user has consistently adhered to the "no wine" habit for over 3 weeks. The system, after recognizing this data, determines that the user no longer needs to be monitored for this habit. The system informs the user that their total habits have been reduced, as shown in Week 8 of Table 13.

The user inputs a change in program goals in response to having trouble sleeping, indicating that her goals are now weight loss and sleep improvement. In response to the user's input, the system suggests to Margaret that her sleep patterns can be tracked within the mobile application using data collected from a third party product, Beddit. The system's collected data from Beddit data indicates that Margaret is waking up prematurely every night, with periods of restlessness occurring at around 3 am. The system recognizes that this sleep pattern occurs in response to her body not consuming enough carbohydrates to manage sleep through the whole night. The system, in response to the user feedback, suggests a change in her food plan.

Referring to Week 9 of Table 13, the user inputs a shift from a Low-Carbohydrate food plan to a Paleo food plan with allergen removal. The system also inputs a suggestion to the user, recommending that the weight loss be monitored with the same scale, to ensure that weight loss patterns are not subject to using different scales. The user's weight is now 195 lbs, but she still sees no improvement in sleep. The system, in response to the user's input, determines that this program is not working for the user, and classifies Margaret's current program as "ineffective." The system also responds to the input by recommending the addition of exercise as an accelerant to the user's program. The user inputs the addition of exercise as an accelerant, as shown in Week 10 of Table 13.

TABLE 13

| Week | User Goal | Food Plan | Accelerant | Total Habits | Reason for Change? |
|---|---|---|---|---|---|
| 1 | Lose Weight | Low Carb (<20 g) | — | 1 | Compute baseline |
| 2 | Lose Weight | Low Carb (<20 g) | — | 1 | Compute baseline-conclude user is Profile A |
| 3 | Lose Weight | Low Carb (<20 g) | No Alcohol | 3 | User's baseline data indicated ketone levels above 5 ppm within 7 days |
| 4 | Lose Weight | Low Carb (<20 g) | No Alcohol | 3 | — |
| 5 | Lose Weight | Low Carb (<20 g) | No Alcohol | 3 | — |
| 6 | Lose Weight | Low Carb (<20 g) | No Alcohol + Controlled Cheat Meals | 6 | Decreased program engagement |

TABLE 13-continued

| Week | User Goal | Food Plan | Accelerant | Total Habits | Reason for Change? |
|---|---|---|---|---|---|
| 7 | Lose Weight | Low Carb (<20 g) | No Alcohol + Controlled Cheat Meals | 6 | — |
| 8 | Lose Weight + Sleep Improvement | Low Carb (<20 g) | No Alcohol + Controlled Cheat Meals | 5 | User reported poor sleep behaviors |
| 9 | Lose Weight + Sleep Improvement | Paleo with Allergen Removal | No Alcohol + Controlled Cheat Meals | 11 | Beddit data indicates poor sleep is attributed to low carb intake |
| 10 | Lose Weight + Sleep Improvement | Paleo with Allergen Removal | No Alcohol + Controlled Cheat Meals + Exercise 2x a Week | 13 | User reports no change in sleep behaviors |

TABLE 14

| Week | Day | Score Computation | Breath Test? (Y/N) | Breath Test Points | Breath Test Result (ppm) | Breath Test Result Points | Habit Adherence | Habits Points | Program Score | Weighted Program Score |
|---|---|---|---|---|---|---|---|---|---|---|
| 3 | 15 | 30%-40%-30% | Y | 30% | 2 | 0% | 3/3 | 30% | 60% | — |
| 3 | 16 | 30%-40%-30% | Y | 30% | 3 | 0% | 3/3 | 30% | 60% | — |
| 3 | 17 | 30%-40%-30% | Y | 30% | 3 | 0% | 1/3 | 10% | 40% | 48% |
| 3 | 18 | 30%-40%-30% | Y | 30% | 3 | 0% | 3/3 | 30% | 60% | 54% |
| 3 | 19 | 30%-40%-30% | Y | 30% | 4 | 0% | 3/3 | 30% | 60% | 58% |
| 3 | 20 | 30%-40%-30% | Y | 30% | 5 | 40% | 2/3 | 20% | 90% | 78% |
| 3 | 21 | 30%-40%-30% | Y | 30% | 5 | 40% | 3/3 | 30% | 100% | 93% |
| 4 | 22 | 30%-40%-30% | Y | 30% | 6 | 40% | 3/3 | 30% | 100% | 99% |
| 4 | 23 | 30%-40%-30% | Y | 30% | 5 | 40% | 3/3 | 30% | 100% | 100% |
| 4 | 24 | 30%-40%-30% | Y | 30% | 6 | 40% | 0/3 | 0% | 70% | 82% |
| 4 | 25 | 30%-40%-30% | Y | 30% | 8 | 40% | 3/3 | 30% | 100% | 91% |
| 4 | 26 | 30%-40%-30% | Y | 30% | 6 | 40% | 3/3 | 30% | 100% | 97% |
| 4 | 27 | 30%-40%-30% | Y | 30% | 6 | 40% | 3/3 | 30% | 100% | 100% |
| 4 | 28 | 30%-40%-30% | Y | 30% | 8 | 40% | 3/3 | 30% | 100% | 100% |
| 5 | 29 | 30%-40%-30% | Y | 30% | 9 | 40% | 2/3 | 20% | 90% | 94% |
| 5 | 30 | 30%-40%-30% | N | 0% | — | 0% | 3/3 | 30% | 30% | 55% |
| 5 | 31 | 30%-40%-30% | N | 0% | — | 0% | 0/3 | 0% | 0% | 18% |
| 5 | 32 | 30%-40%-30% | Y | 30% | 3 | 0% | 1/3 | 10% | 40% | 27% |
| 5 | 33 | 30%-40%-30% | N | 0% | — | 0% | 0/3 | 0% | 0% | 12% |
| 5 | 34 | 30%-40%-30% | Y | 30% | 3 | 0% | 1/3 | 10% | 40% | 28% |
| 5 | 35 | 30%-40%-30% | N | 0% | — | 0% | 0/3 | 0% | 0% | 12% |
| 6 | 36 | 40%-30%-30% | N | 0% | — | 0% | 1/6 | 5% | 5% | 7% |
| 6 | 37 | 40%-30%-30% | Y | 40% | 3 | 0% | 6/6 | 30% | 70% | 44% |
| 6 | 38 | 40%-30%-30% | N | 0% | — | 0% | 4/6 | 20% | 20% | 34% |
| 6 | 39 | 40%-30%-30% | Y | 40% | 3 | 0% | 6/6 | 30% | 70% | 55% |
| 6 | 40 | 40%-30%-30% | N | 0% | — | 0% | 6/6 | 30% | 30% | 41% |

TABLE 14-continued

| Week | Day | Score Computation | Breath Test? (Y/N) | Breath Test Points | Breath Test Result (ppm) | Breath Test Result Points | Habit Adherence | Habits Points | Program Score | Weighted Program Score |
|---|---|---|---|---|---|---|---|---|---|---|
| 6 | 41 | 40%-30%-30% | Y | 40% | 3 | 0% | 6/6 | 30% | 70% | 58% |
| 6 | 42 | 40%-30%-30% | Y | 40% | 5 | 30% | 6/6 | 30% | 100% | 84% |
| 7 | 43 | 40%-30%-30% | Y | 40% | 5 | 30% | 5/6 | 25% | 95% | 94% |
| 7 | 44 | 40%-30%-30% | Y | 40% | 4 | 0% | 3/6 | 15% | 55% | 72% |
| 7 | 45 | 40%-30%-30% | Y | 40% | 5 | 30% | 1/6 | 5% | 75% | 71% |
| 7 | 46 | 40%-30%-30% | Y | 40% | 5 | 30% | 6/6 | 30% | 100% | 88% |
| 7 | 47 | 40%-30%-30% | Y | 40% | 4 | 0% | 6/6 | 30% | 70% | 80% |
| 7 | 48 | 40%-30%-30% | Y | 40% | 5 | 30% | 6/6 | 30% | 100% | 91% |
| 7 | 49 | 40%-30%-30% | Y | 40% | 6 | 30% | 3/6 | 15% | 85% | 88% |
| 8 | 50 | 40%-20%-40% | Y | 40% | 8 | 30% | 3/5 | 24% | 94% | 92% |
| 8 | 51 | 40%-20%-40% | N | 0% | — | 0% | 5/5 | 40% | 40% | 61% |
| 8 | 52 | 40%-20%-40% | Y | 40% | 8 | 30% | 5/5 | 40% | 110% | 87% |
| 8 | 53 | 40%-20%-40% | Y | 40% | 8 | 20% | 4/5 | 32% | 92% | 92% |
| 8 | 54 | 40%-20%-40% | Y | 40% | 7 | 20% | 4/5 | 32% | 92% | 94% |
| 8 | 55 | 40%-20%-40% | Y | 40% | 6 | 20% | 5/5 | 40% | 100% | 97% |
| 8 | 56 | 40%-20%-40% | Y | 40% | 8 | 20% | 5/5 | 40% | 100% | 99% |
| 9 | 57 | 40%-20%-40% | Y | 40% | 7 | 20% | 11/11 | 40% | 100% | 100% |
| 9 | 58 | 40%-20%-40% | Y | 40% | 8 | 20% | 11/11 | 40% | 100% | 100% |
| 9 | 59 | 40%-20%-40% | Y | 40% | 6 | 20% | 4/11 | 15% | 75% | 85% |
| 9 | 60 | 40%-20%-40% | Y | 40% | 8 | 20% | 11/11 | 40% | 100% | 92% |
| 9 | 61 | 40%-20%-40% | Y | 40% | 8 | 20% | 9/11 | 33% | 93% | 93% |
| 9 | 62 | 40%-20%-40% | Y | 40% | 8 | 20% | 10/11 | 36% | 96% | 96% |
| 9 | 63 | 40%-20%-40% | Y | 40% | 7 | 20% | 11/11 | 40% | 100% | 98% |
| 10 | 64 | 40%-20%-40% | N | 0% | — | 0% | 13/13 | 40% | 40% | 64% |
| 10 | 65 | 40%-20%-40% | Y | 40% | 6 | 20% | 13/13 | 40% | 100% | 82% |
| 10 | 66 | 40%-20%-40% | Y | 40% | 7 | 20% | 13/13 | 40% | 100% | 94% |
| 10 | 67 | 40%-20%-40% | Y | 40% | 6 | 20% | 13/13 | 40% | 100% | 100% |
| 10 | 68 | 40%-20%-40% | N | 0% | — | 0% | 13/13 | 40% | 40% | 64% |
| 10 | 69 | 40%-20%-40% | Y | 40% | 7 | 20% | 13/13 | 40% | 100% | 82% |
| 10 | 70 | 40%-20%-40% | Y | 40% | 7 | 20% | 13/13 | 40% | 100% | 94% |

There are many possible algorithms that can be used by the system for determining the weights that make up the program score. In one embodiment, the system uses an algorithm that looks at the user's classification and selects a pre-defined set of weights as determined by a subject matter expert. As the user's classification changes, their program score ratio also changes.

In another embodiment, an algorithm computes the statistical variance of the program score components and increases the weight of a component relative to its variance. In other words, the more likely a factor is to change, the more influence it has on the program score. This algorithm allows the user to focus on aspects that they need to improve on.

In other embodiments, the system uses an algorithm that uses more advanced statistical analysis methods such as TFIDF (term frequency-inverse document frequency) for determining the weights. TFIDF is a numerical analysis method popularized in Web search and text retrieval. TDIDF is formally defined as the Cartesian dot product of the "TF" and "IDF" terms. "TF" (term-frequency) is defined as the number of times a term appears in a document. "IDF" (inverse-document frequency) is defined as the natural logarithm of the total number of documents divided by the number of documents that contain a particular term. TFIDF reflects how important a particular a term is to a particular document. Intuitively, the algorithm identifies words that occur many times while "discounting" the words that appear in many documents and hence make them less "special". When applying TFIDF to weighting a program score, certain changes need to be made to the formulation. Instead of documents you have users. And instead of terms you have certain "fluctuations," such as a weight fluctuation of 2 lbs. By running TFIDF, the system determines which fluctuations are most important to a particular user and thus will apply greater weight to that fluctuation.

The system may also use various combinations of the aforementioned and other algorithms.

In all of these situations, the algorithm(s) is/are used by the system in conjunction with a UI that makes it easy for subject matter experts to review the behavior of the system and enable them to rapidly determine if the system is operating appropriately and making interventions as needed. Before the program score is computed, the results may be sent in real time to a subject matter expert who can review the weights and intervene to make changes before the user sees the result or make changes that will impact future program score computations. In such embodiments, the efficiency of processing the request is tantamount, and since the rate limiting factor is a human user, the UI is key. This UI achieves two goals that are at odds with one another—generate quick feedback and generate high quality feedback. One UI that allows this efficiency is to have two subject matter experts see streaming lists of results. Each subject matter expert indicates if they agree with the system recommendation. The experts only have a limited time period, such as 5 seconds, to respond. If they fail to respond, it is assumed that they agree with the system. If both of the subject matter experts disagree, then, and only then, is the program score flagged for further analysis and potential changes. This UI enables subject matter experts to work quickly, enables the system to operate with a minimal number of subject matter experts, and ensures a high-quality result because it uses multiple experts.

Multi-Flow Human-Machine Interface

The process by which the system collects feedback from program participants is important for at least two reasons. First, unless the system collects information that is relevant to the success of the currently assigned health program and possible changes to that program, the system will not be able to generate high quality recommendations, such as recommendations of health program changes. Second, if the process is overly burdensome, users may fail to answer questions or may prematurely discontinue their participation.

To address these issues in some embodiments, the mobile application presents two different types of screen flows or user interface flows to the user. The first type of UI flow is preferably presented each time the user takes a ketone measurement or other daily biometric measurement. The second type of UI flow is presented less frequently, such as on a weekly basis and/or when the user finishes use of a multi-day (e.g., 7-day) disposable. The combined use of these two different types of UI flows enables the system to efficiently collect information from the user while reducing the burden placed on the user.

The first type of flow, referred to as the primary flow, primarily seeks information from the user regarding conditions and behaviors that may have affected the measurement. For example, the user may be asked when they had their last meal, and whether, since the prior measurement, they followed the assigned diet, exercised more than usual, experienced stress, etc. Examples of the types of questions that may be presented in the primary flow are shown in Table 15. Typically, the primary flow is executed once per day, at the time of a daily biometric (e.g., breath ketone) measurement. In embodiments in which the user performs the measurement multiple times per day, the primary flow may be executed with each such measurement and thus multiple times per day.

TABLE 15

Example questions presented in primary UI flow

Have you followed the health program? (If no, optionally present additional questions about what aspects of plan were not followed and why)
When was your last meal?
Did you experience stress? (If yes, optionally present additional questions regarding level of stress and/or cause of stress)
Did you miss a medication?
Did you sleep well?
Did you engage in unusually exercise?
Are you traveling?
Are you having a menstrual cycle?
Did you consume significant caffeine?
What is your current weight?
Your ketone level decreased significantly. Did something unusual happen? (Present with list of possible events/tags from which to select)

The actual questions presented in the primary flow may depend upon the currently assigned health program; for example, if the current health program limits alcohol consumption, the user may be asked whether they consumed alcohol. In addition, some questions within the primary flow may depend on the user's responses to other questions within the primary flow; for example, the mobile application 32 may use a decision tree to select the questions to present, and certain branches of the tree may be response-dependent. The questions presented in the primary flow can also depend on other factors, such as ketone measurement history, weight measurement history, user responses from prior executions of the primary flow, etc.

In some embodiments, the primary flow is presented just after the user performs a breath test but before the results of the breath test are presented to the user. For example, the mobile application 32 may start the primary flow when analysis of a disposable cartridge begins.

The second type of UI flow, referred to as a secondary flow, collects information from the user that is not specific to any particular measurement (e.g., information regarding the user's satisfaction with the current program, preferences, goals, etc.). For example, the user may be asked whether they have become bored with the current program, whether they wish to change the current program, whether their goals have changed, etc. Examples of the types of questions that may be asked in the secondary UI flow are shown in Table 16. The actual questions presented may depend on various factors, such as the currently assigned health program, the feedback collected from the user via the primary flow over the preceding cycle, the user's history of ketone measurements, and the user's history of weight measurements. As with the primary flow, the mobile application 32 may use a decision tree to select the secondary-flow questions to present. The primary flow and secondary flow may also be referred to as the "micro flow" and "macro flow," respectively.

TABLE 16

Example questions presented in secondary UI flow

Rate your satisfaction with [<rule 1>, <rule 2>, <rule 3>, . . . ]
of your health program.
Will you be traveling in the upcoming week? If so, when and where?
Are you planning to engage in significant exercise? If so, when?
Is it normal that you did not tag any of your measurements?
Are you bored with the current health program?
Would you like to increase your exercise level?
Have your goals changed? (If yes, present list of goals from
which to select)
Any changes in health conditions, vitamins or medications?
Any life events, such as a move, family member stress, etc.?

The first question in Table 16 may be used where the health program is composed of a set of rules. Examples of rules include (1) maintain carbs below N per day, (2) no alcohol, (3) maintain heart rate above X for at least Y minutes each day, and (4) engage in meditation for X minutes each day. The user may, for example, be asked to rate each such rule on a scale of 1 to 5 stars, and the responses may be used to determine which rules, if any, should be modified or discontinued (as explained below with reference to FIG. 34).

As illustrated in Table 16, some of the questions may ask the user about the upcoming week or other upcoming time period. The responses to such questions may be used to provide event-specific tips or other messaging. For example, if the user will be traveling to a particular area, the mobile application 32 may present recommendations of particular restaurants and health clubs in the area. As another example, if the user will be engaging in significant exercise, the mobile application 32 may temporarily increase the user's permissible carb intake.

Figure 32A:
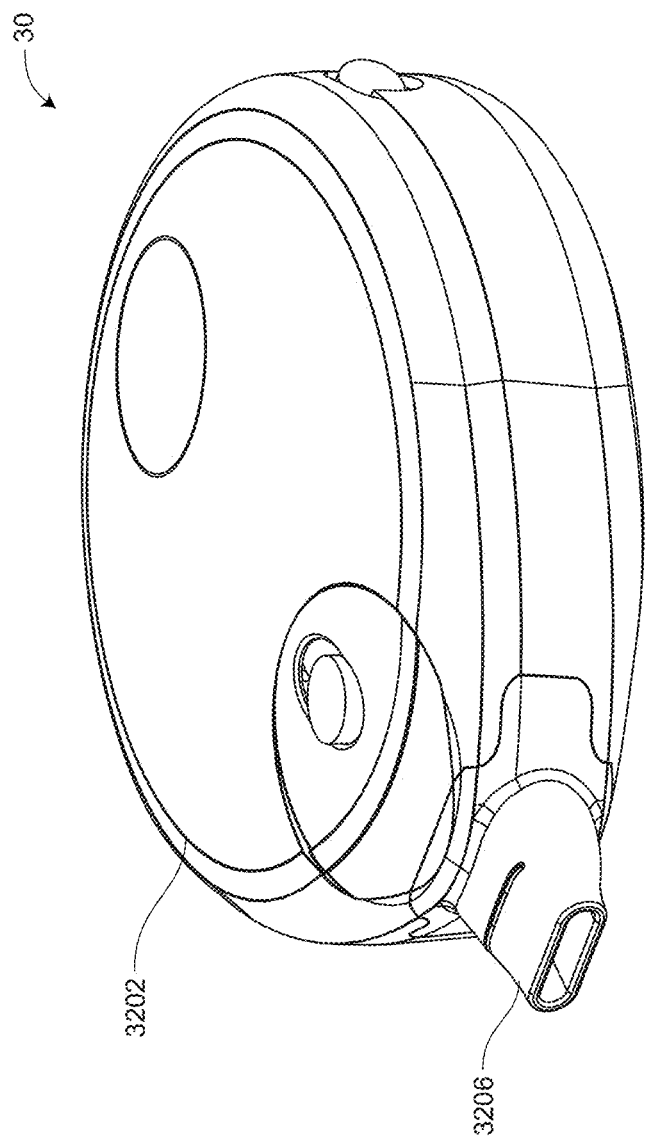
FIGS. 32A-32C illustrate an embodiment of the breath analysis device that uses a 7-day disposable cartridge.
Figure 32B:
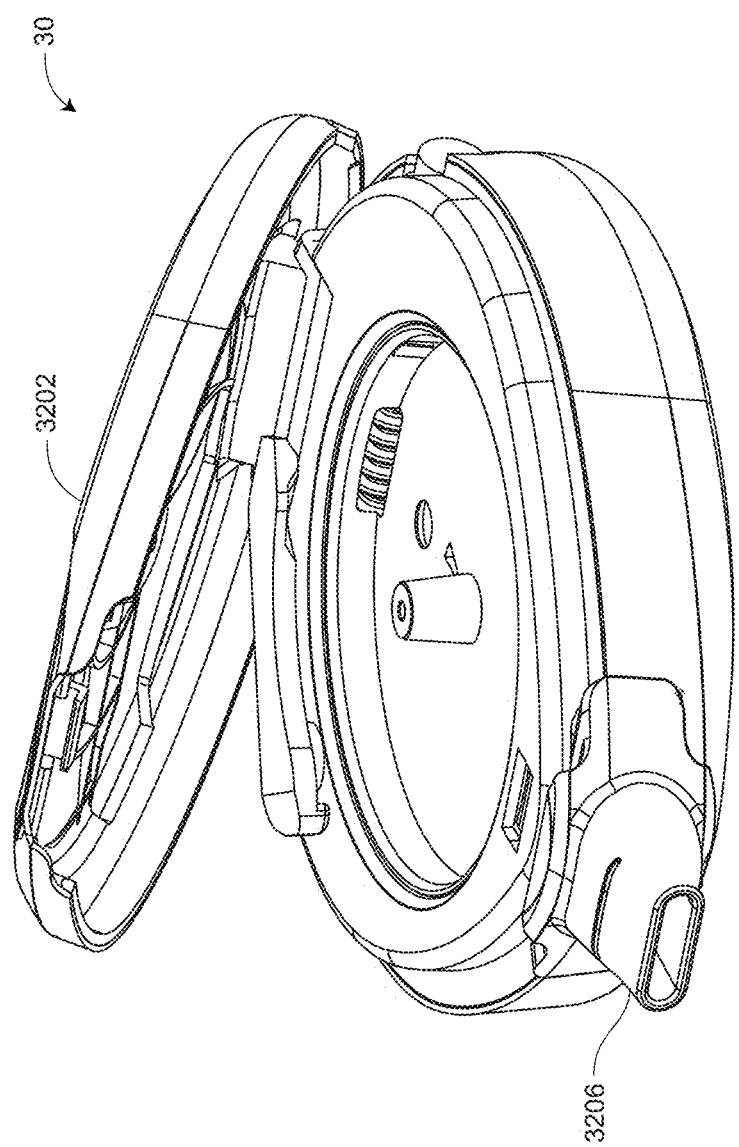

The secondary flow is executed less frequently than the primary flow, such as on a weekly, biweekly or monthly basis. In some embodiments, the mobile application initiates (executes) the secondary (macro) flow when the user finishes or replaces a multi-day disposable cartridge. The invention is also applicable to ketone measurement devices that do not use disposable cartridges, or that use single-test disposable cartridges. For example, the invention may be implemented in the context of (1) a breath analysis device in which the user inserts a single-test disposable cartridge for each breath test, and in which the cartridges are provided to the user in a seven-cartridge package that is intended to last for one week, (2) a breath analysis device that senses acetone using a nanoparticle sensor, without the use of a disposable component, or (3) a ketone measurement device that measures ketones in other bodily fluids such as blood, urine or sweat. FIGS. 32A-32C and 33 illustrate one example of a breath analysis device 30 that uses a 7-day disposable cartridge 3200 (cartridge shown separately in FIG. 33). In FIG. 32A, the device is shown with the lid 3202 closed, and in FIGS. 32B and 32C, the device is shown with the lid open. The device 30 is shown with the cartridge 3200 removed in FIG. 32B, and with the cartridge inserted in FIG. 32C. The primary/secondary flow features described herein are not limited to a device that uses a 7-day or other multi-day disposable cartridge; thus, the following description of FIGS. 32A-32C and FIG. 33 is not intended to be limiting.

Figure 33:
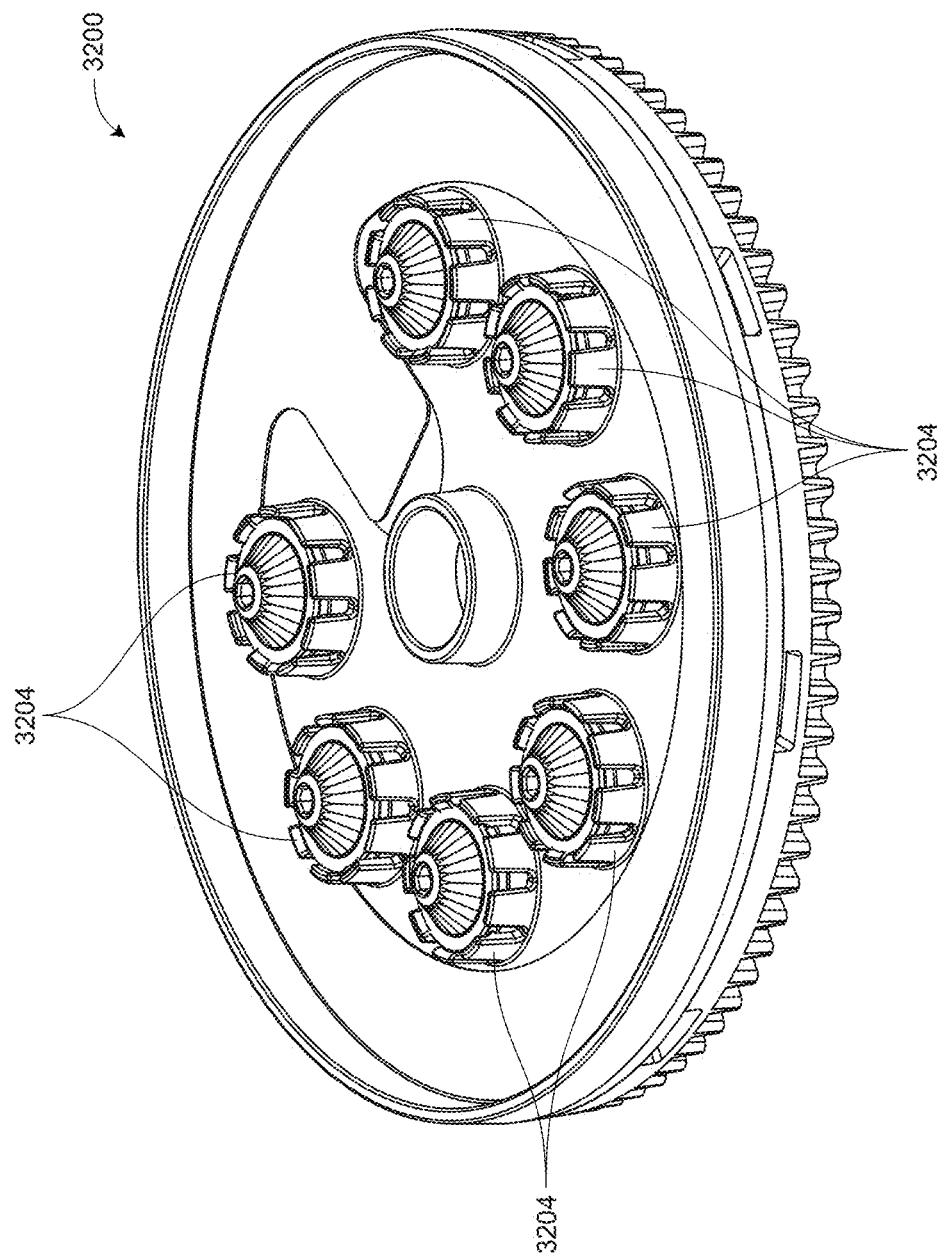
FIG. 33 illustrates the 7-day disposable cartridge shown in FIG. 32C.

As shown in FIG. 33, the cartridge 3200 is in the form of a carousel that includes seven chemistry pods 3204, one for each daily breath test. As seen along the lower bottom of the drawing, the lower, outer circumference of the cartridge 3200 is geared to enable a motor (not shown) of the device 30 to rotate the cartridge between various positions, including positions that place a particular chemistry pod 3204 in the device's breath flow path. The flow path extends from the device's mouthpiece 3206 to a breath output port (now shown). Each chemistry pod includes an interactant material (e.g., interactant beads or a solid, porous structure containing the interactant), and in some embodiments, also includes a sponge member soaked with a developer solution that is dispensed onto the interactant material after a breath sample is passed through the chemistry pod.

Figure 32C:
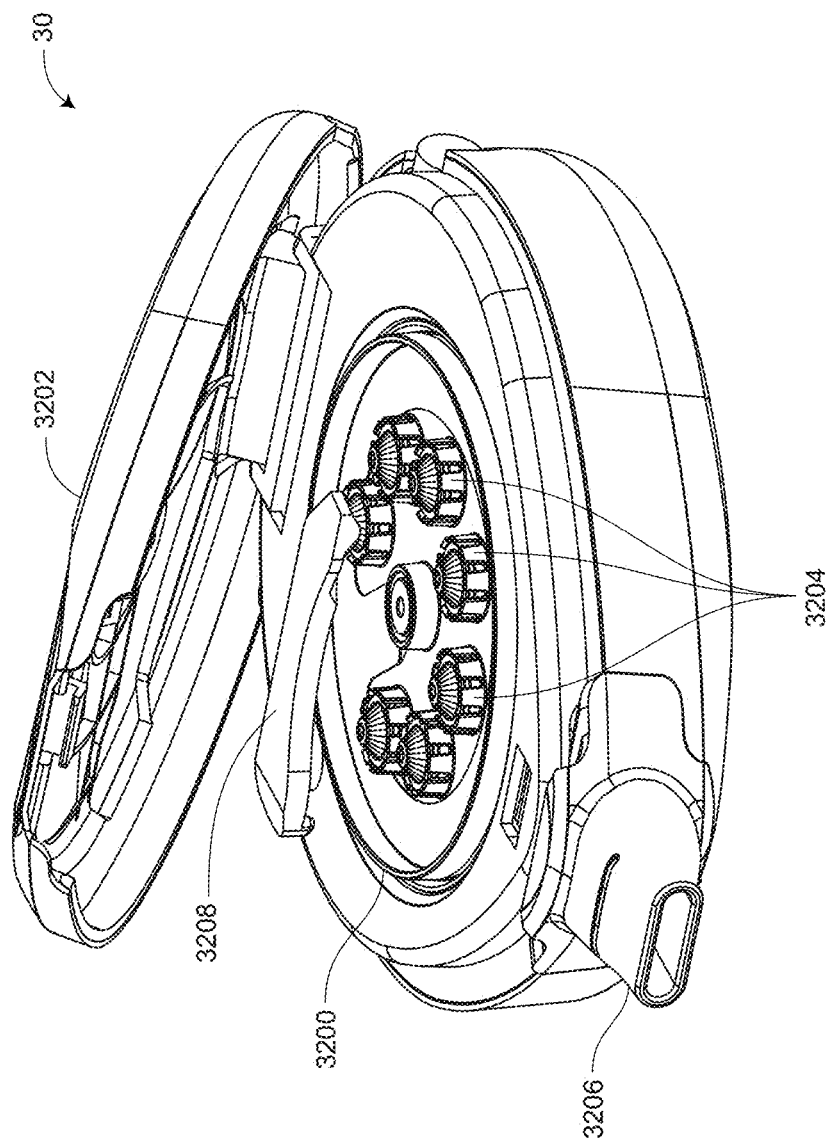

To perform a breath test, the user exhales a breath sample into the mouthpiece 3206, and the device 30 routes all or a portion of the breath sample through one of the chemistry pods 3204, causing acetone in the breath sample to be extracted by the interactant material. The device then rotates the carousel to a position that aligns that chemistry pod with a photodiode/LED arrangement (not shown) that measures a color change produced by a chemical reaction involving the interactant material and the extracted acetone. One example of a photodiode/LED arrangement that may be used for this purpose is disclosed in U.S. Provisional Patent Appl. No. 62/831,017, filed Apr. 8, 2019, the disclosure of which is hereby incorporated by reference. In embodiments in which a developer solution is used, the rotation that brings the chemistry pod 3204 into alignment with the photodiode/LED arrangement also causes a boom 3208 to press down on the chemistry pod (as shown in FIG. 32C), causing the sponge member to become depressed such that the developer solution it holds is released/dispensed onto the interactant material. As is known in the art, the developer solution causes the above-noted chemical reaction to occur, or increases the magnitude of the reaction.

Once a processor of the device 30 measures the color change using the photodiode/LED assembly, the processor transmits the resulting measurement (which represents the measured acetone level) to the user's mobile device 34 (FIG. 1) and its mobile application 32 via a wireless transceiver of the device 30. The device 30 also preferably wirelessly notifies the mobile application 32 when the last chemistry pod 3204 is used, and/or when the cartridge 3200 is removed, such that the mobile application can execute the secondary (macro) flow in response.

Various other types of triggers can additionally or alternatively be used to initiate execution of the secondary flow. For example, the mobile application 32 may execute the secondary flow at a pre-selected day and time each week or according to some other periodic schedule. As another example, the mobile application may execute the secondary flow in response to a sustained drop in the user's ketone level, in response to a plateau in the user's weight level, or in response to a decline in the user performing daily breath tests.

Table 17 illustrates an example use case scenario in which a user on a carbohydrate-restricted diet interacts with the system over a 14-day period using the mobile application 32. This example is applicable, but is not limited, to a breath analysis device that uses a 7-day disposable cartridge having seven chemistry pods, one for each day. The "weight," "symptoms" and "tags" columns show information collected from the user at measurement time (typically in the morning before eating) through execution of the primary flow. Although various other types of information may be collected, they are omitted to simplify the example. The "tags" in this example are user indications of conditions or events associated with the respective measurements; for example, if the user experienced poor sleep, missed a medication, or failed to comply with the diet during the period immediately preceding the measurement, the user can tag the measurement accordingly (as described, e.g., in U.S. Pat. No. 10,278,640, the disclosure of which is hereby incorporated by reference). The "ahead knowledge" column shows knowledge obtained from the user (typically through the secondary flow) about upcoming events, such as travel events. The "system feedback" column indicates some types of auto-generated messaging that may be provided by the system to the user based on the collected information, including the user's ketone measurements.

TABLE 17

| Day | Ketone Level | Weight | Symptoms | Tags | Ahead knowledge | System Feedback |
|---|---|---|---|---|---|---|
| 1 | 0 | 180 | none | none | | Positive |
| 2 | 1.2 | 180 | none | none | | Positive |
| 3 | 1.8 | 179.8 | headache | none | | Tip on headaches |
| 4 | 2.5 | | headache | none | | Concern on headaches |
| 5 | 4.0 | | headache | none | | Prompt for a call from health coach |
| 6 | 4.0 | 178 | headache | none | | |
| 7 | 5.0 | | headache, constipated | none | | Tip on constipation; instruction to replace 7-day disposable; execute secondary flow |
| 8 | 5.0 | 178 | headache, constipated | poor sleep | | Exercise tip |
| 9 | 4.8 | 177 | headache, constipated | none | Exercise/ hike | |
| 10 | 4.7 | 179 | headache, constipated | none | | Packing suggestions |
| 11 | 5.2 | 182 | headache, constipated | none | | Food choices in area/navigating airport |
| 12 | 5.9 | 182 | | none | Travel to Memphis | |
| 13 | 8.0 | 180 | | none | Travel to Memphis | |
| 14 | 7.5 | 176 | | none | | Good progress; instruction to replace 7-day disposable; execute secondary flow |

In this example, at the end of the first week, the system (via the mobile application) reminds the user to replace the 7-day disposable cartridge (if such a cartridge is used), and executes the secondary (macro) flow. The secondary flow may ask the user questions about the user's ability to stay on the low carb diet, and the responses may be used to determine whether to suggest a diet change. The secondary flow may also ask the user questions that are based on the information collected from the primary flow during the preceding week. For example, the user may be asked "Is it normal that you did not tag any measurements?"

The secondary flow may also ask the user about upcoming events, such as travel and exercise events, planned for the following week. In this example of Table 17, the user has indicated that they plan to take a hike on day 9, and will be traveling to Memphis on days 12 and 13, as shown in the "ahead knowledge" column. The system in this example uses this "ahead knowledge" information to provide an exercise tip (such as a hydration tip) on day 8; to provide packing suggestions on day 11, and to provide food choice information (e.g., suggested restaurants in Memphis for those on low carb diets) and airport navigation information on day 12.

Although no diet change is shown in this example, the system may, in some cases, recommend or make a diet change, or other health program change, based on the collected information, including the information collected from the primary and secondary flows. For example, the system may recommend a different food plan, accelerant, and/or target goal. Typically, the system will suggest or make any such health program change as part of, or immediately following, execution of the secondary flow. An appropriate algorithm may be used for this purpose, as described below. The task of modifying the health program may be an interactive task in which the user can accept or reject suggested modifications.

Figure 34:
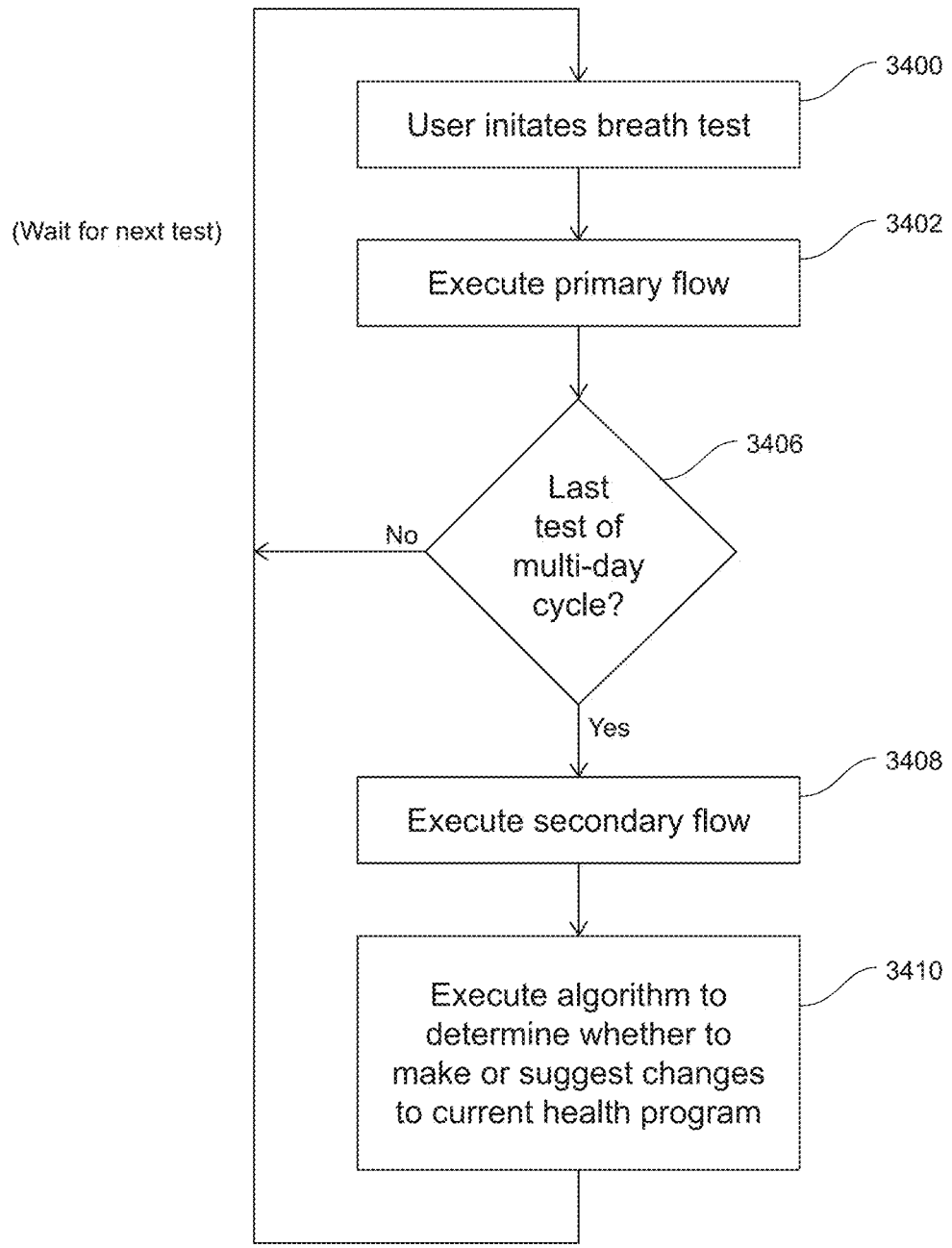
FIG. 34 illustrates a multi-flow process implemented by the system to collect information used to generate or select health program modifications.

FIG. 34 illustrates the overall process implemented by the system to use primary and secondary flows as described above. This process may be embodied in the mobile application 32, or in the mobile application in combination with a server-executed application that communicates with the mobile application. As shown in blocks 3400 and 3402, the system executes the primary flow each time the user initiates a breath test, which is typically a daily breath test performed in the morning. As shown in block 3406, this cycle continues until the end of the multi-day (e.g., 7-day) period, at which point the system executes the secondary flow as shown in block 3408. Following, or during, execution of the secondary flow, the system also executes an algorithm (block 3410) to determine whether to suggest or make any changes to the user's current health program. Any such changes are recorded by the system and communicated to the user.

Any of a variety of algorithms, including those described above, may be used to select health program changes to make or recommend. In one embodiment, each health program is in the form of a set of rules: Health program=[rule 1, rule 2, rule 3, . . . ]. Examples of rules include a rule that specifies a particular diet, a rule that specifies a level of daily exercise, and a rule that prohibits consumption of alcohol. As part of the secondary flow, the system may ask the user to rate each rule on a specified scale, such as a scale of 1 to 5 stars. To determine whether a change to the current health program should be made, the system in one embodiment generates a "program change" score based on three components, (1) user satisfaction with the current health program, as may be determined, e.g., from the user's ratings of the program's rules, (2) health program results, such as ketone measurements and/or weight measurements, and (3) user compliance with the current health program, as may be reported by the user during the primary flow and/or determined based on whether the user misses any breath tests. For example, the program score may be generated based on an average of: user satisfaction of 50%, results of 80% (as compared, e.g., to other users on the same or similar health programs), and compliance of 100%. These three components may, but need not, be weighted equally when averaged or combined. The methods described in the preceding sections for generating a program score may also be used to generate the program change score. The program change score may be compared to a selected threshold, such as 70% or 80%, to determine whether to make or suggest a modification to the current health program. If this results in a determination that a modification should be made, the user's ratings of the individual rules (if any) may be considered to determine which rule or rules of the health program should be modified or replaced.

Additional Implementation Details

All of the actions described herein as being performed by "the system" may be performed by (1) the AI-Based Health Coaching System 40, under the control of program instructions executed, e.g., by a server machine or group of machines, (2) a mobile device 34 of a user, under control of the mobile application 32, or (3) a combination of (1) and (2). All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on general purpose computer hardware, or combinations of both. To clearly illustrate this interchangeability of hardware and software, various illustrative components, blocks, modules, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A system for analyzing progress of a user on a health program, comprising:
   - a breath analysis device that is configured to generate breath ketone measurements based on breath samples provided by a user, wherein the breath analysis device comprises a processor and a wireless transceiver, and is configured to use the wireless transceiver to communicate with a mobile phone of the user; and
   - a mobile application configured to run on the mobile phone of the user and to receive and display ketone measurements generated by the breath analysis device, wherein the mobile application is configured to periodically execute a primarily user interface flow that prompts the user to supply information associated with specific ketone measurements, including information regarding whether the user has complied with the health program, wherein the mobile application includes a measurement tagging user interface that enables the user to tag individual ketone measurements with information regarding associated conditions or events that may have affected the respective measurements;
   - wherein the mobile application is configured to execute a secondary user interface flow less frequently than it executes the primary user interface flow such that multiple ketone measurements are generated between consecutive executions of the secondary user interface flow, wherein the secondary user interface flow prompts the user to supply information that is not specific to a particular measurement, including information regarding the user's level of satisfaction with the health program;
   - wherein the mobile application is configured to output, on a display of the mobile phone, recommended modifications to the health program, said recommended modifications based at least partly on the ketone measurements and information collected from the user through the primary and secondary user interface flows;
   - wherein the system operates under control of processor-executed program instructions stored in memory devices.

2. The system of claim 1, wherein the system is programmed to generate the recommended modifications based on at least (1) information collected from the user through the primary and secondary user interface flows, and (2) the breath ketone measurements.

3. The system of claim 1, wherein the system is programmed to determine whether to recommend a modification to the health program based on at least (1) a measure of the user's compliance with the health program as determined from the primary user interface flow, and (2) a measure of the user's satisfaction with the health program as determined from the secondary user interface flow.

4. The system of claim 1, wherein the information collected through the primary user interface flow includes symptoms experienced by the user.

5. The system of claim 1, wherein the information collected through the primary user interface flow includes health program compliance information.

6. The system of claim 1, wherein executing the secondary user interface flow comprises selecting questions to ask the user based on information collected from the user in the primary user interface flow.

7. A method for analyzing progress of a user on a health program, comprising, by execution of program instructions by one or more processors:
   - receiving, from a breath analysis device, ketone measurements reflective of breath ketone levels of the user;
   - executing, in association with at least some of the ketone measurements, a primary user interface flow that that prompts the user to supply information associated with the ketone measurements, including regarding whether the user has complied with the health program;
   - in response to a triggering event that occurs less frequently than a frequency with which the primary user interface flow is executed, executing a secondary user interface flow that prompts the user to supply additional information associated with the health program, including an indication of a level of satisfaction the user has with the health program;
   - generating a modification to the health program based at least partly on the ketone measurements and on information supplied by the user in the primary and secondary user interface flows; and
   - outputting a visual representation of said modification for display to the user;
   - said method performed programmatically by a computing system that comprises a mobile device that executes a mobile application.

8. The method of claim 7, wherein the triggering event is associated with completion of use by the user of a multi-test disposable cartridge used by the breath analysis device.

9. The method of claim 7, wherein the triggering event is an expiration of a multi-day period of time.

10. The method of claim 7, wherein the method comprises selecting questions to present to the user in the secondary user interface flow based at least partly on information collected from the user in the primary user interface flow.

11. The method of claim 7, wherein the information collected through the primary user interface flow includes symptoms experienced by the user.

12. The method of claim 7, wherein the information collected through the primary user interface flow includes health program compliance information.

13. The method of claim 7, further comprising generating, on the mobile device, a measurement tagging user interface that enables the user to tag individual ketone measurements with information regarding associated conditions or events that may have affected the respective measurements.

* * * * *